United States Patent
Alvaro et al.

(10) Patent No.: US 7,482,365 B2
(45) Date of Patent: Jan. 27, 2009

(54) PIPERIDYLCARBOXAMIDE DERIVATIVES AND THEIR USE IN THE TREATMENT OF TACHYKININ-MEDIATED DISEASES

(75) Inventors: Giuseppe Alvaro, Verona (IT); Alfredo Paio, Verona (IT); Alessandro Pontiroli, Verona (IT); Simone Spada, Verona (IT); Maria Elvira Tranquillini, Verona (IT)

(73) Assignee: Glaxo Group Limited, Middlesex (GB)

( * ) Notice: Subject to any disclaimer, the term of this patent is extended or adjusted under 35 U.S.C. 154(b) by 555 days.

(21) Appl. No.: 10/502,266

(22) PCT Filed: Feb. 5, 2003

(86) PCT No.: PCT/GB03/00499
§ 371 (c)(1), (2), (4) Date: Mar. 17, 2005

(87) PCT Pub. No.: WO03/066589
PCT Pub. Date: Aug. 14, 2003

(65) Prior Publication Data
US 2005/0171153 A1    Aug. 4, 2005

(30) Foreign Application Priority Data
Feb. 8, 2002 (GB) .................. 0203019.5
Feb. 8, 2002 (GB) .................. 0203021.1

(51) Int. Cl.
A61K 31/445 (2006.01)
C07D 211/60 (2006.01)

(52) U.S. Cl. ............. 514/317; 514/326; 546/200; 546/226

(58) Field of Classification Search ........... 514/317, 514/326; 546/200, 226
See application file for complete search history.

(56) References Cited

U.S. PATENT DOCUMENTS

| | | | |
|---|---|---|---|
| 4,087,424 A | 5/1978 | Saikawa et al. | |
| 4,110,327 A | 8/1978 | Saikawa et al. | |
| 4,112,090 A | 9/1978 | Saikawa et al. | |
| 4,219,554 A | 8/1980 | Saikawa et al. | |
| 4,308,387 A | 12/1981 | Bjork et al. | |
| 4,327,097 A | 4/1982 | Saikawa et al. | |
| 4,379,152 A | 4/1983 | Saikawa et al. | |
| 4,410,522 A | 10/1983 | Saikawa et al. | |
| 5,028,610 A | 7/1991 | Hirai et al. | |
| 5,109,014 A | 4/1992 | Jacobson et al. | |
| 5,334,606 A | 8/1994 | MacLeod et al. | |
| 5,348,955 A | 9/1994 | Greenlee et al. | |
| 5,360,820 A | 11/1994 | Hagan et al. | |
| 5,464,788 A | 11/1995 | Bock et al. | |
| 5,538,982 A | 7/1996 | Hagan et al. | |
| 5,563,127 A | 10/1996 | Amparo et al. | |
| 5,576,317 A | 11/1996 | Gonsalves et al. | |
| 5,654,316 A * | 8/1997 | Carruthers et al. | 514/307 |
| 5,696,123 A | 12/1997 | Dollinger et al. | |
| 5,698,538 A | 12/1997 | Amparo et al. | |
| 5,708,006 A | 1/1998 | Dollinger et al. | |
| 5,710,169 A | 1/1998 | Russell et al. | |
| 5,716,942 A | 2/1998 | Dorn et al. | |
| 5,756,504 A | 5/1998 | Bock et al. | |
| 5,814,636 A | 9/1998 | Katano et al. | |
| 5,859,015 A | 1/1999 | Graham et al. | |
| 5,883,096 A | 3/1999 | Lowe et al. | |
| 5,935,951 A | 8/1999 | Ofner et al. | |
| 5,952,315 A | 9/1999 | Baker et al. | |
| 5,977,104 A | 11/1999 | Baker et al. | |
| 5,985,881 A | 11/1999 | Dollinger et al. | |
| 5,998,444 A | 12/1999 | Russell et al. | |
| 6,037,352 A | 3/2000 | Lowe et al. | |
| 6,057,323 A | 5/2000 | Zhang et al. | |
| 6,090,807 A | 7/2000 | Hellendahl et al. | |
| 6,114,315 A | 9/2000 | Baker et al. | |
| 6,117,855 A | 9/2000 | Carlson et al. | |
| 6,147,083 A | 11/2000 | Russell et al. | |
| 6,191,135 B1 | 2/2001 | Dollinger et al. | |
| 6,191,139 B1 | 2/2001 | Hagan et al. | |
| 6,197,772 B1 | 3/2001 | Janssens et al. | |
| 6,235,732 B1 | 5/2001 | Dollinger et al. | |
| 6,288,068 B1 | 9/2001 | Lowe et al. | |
| 6,313,144 B1 * | 11/2001 | McCullough et al. | 514/327 |
| 6,319,953 B1 | 11/2001 | Carlson et al. | |

(Continued)

FOREIGN PATENT DOCUMENTS

DE    2519400    4/1978

(Continued)

OTHER PUBLICATIONS

Beattie et al. "The pharmacology of . . . " CA124:106458 (1996).*

(Continued)

*Primary Examiner*—Celia Chang
(74) *Attorney, Agent, or Firm*—R. Steve Thomas

(57) ABSTRACT

The present invention relates to piperidine derivatives of formula (I):

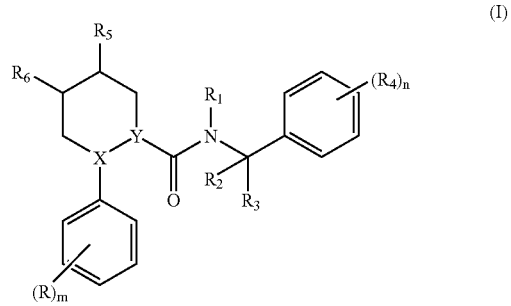

wherein R, $R_1$, $R_2$, $R_3$, $R_4$, $R_5$, $R_6$, X, Y, m and n are as defined herein; and pharmaceutically acceptable salts and solvates thereof; the process for their preparation and their use in the treatment of conditions mediated by tachykinins.

5 Claims, No Drawings

U.S. PATENT DOCUMENTS

| | | | |
|---|---|---|---|
| RE37,886 E | 10/2002 | Janssens et al. | |
| 6,479,518 B2* | 11/2002 | Finke et al. | 514/330 |
| 6,521,621 B1 | 2/2003 | Janssens et al. | |
| 6,642,240 B2 | 11/2003 | Alvaro et al. | |
| 2002/0103205 A1 | 8/2002 | Lowe et al. | |
| 2005/0090534 A1* | 4/2005 | Sakai et al. | 514/365 |
| 2005/0239829 A1* | 10/2005 | Takahashi et al. | 514/317 |

FOREIGN PATENT DOCUMENTS

| | | |
|---|---|---|
| EP | 287734 | 10/1987 |
| EP | 293532 | 10/1987 |
| EP | 0532456 | 3/1993 |
| EP | 0655442 | 5/1995 |
| EP | 718287 | 12/1995 |
| EP | 0721941 | 7/1996 |
| GB | 1508062 | 4/1975 |
| JP | 57/118587 | 7/1982 |
| WO | WO 92/16211 | 10/1992 |
| WO | WO 95/00498 | 1/1995 |
| WO | WO 95/25443 | 9/1995 |
| WO | WO 96/02503 | 2/1996 |
| WO | WO 96/03378 | 2/1996 |
| WO | WO 96/10562 | 4/1996 |
| WO | WO 96/14844 | 5/1996 |
| WO | WO 96/20173 | 7/1996 |
| WO | WO 97/16440 | 5/1997 |
| WO | WO 97/24324 | 7/1997 |
| WO | WO 97/32865 | 9/1997 |
| WO | WO 97/36592 | 10/1997 |
| WO | WO 97/36593 | 10/1997 |
| WO | WO 97/36888 | 10/1997 |
| WO | WO 97/36889 | 10/1997 |
| WO | WO 98/01133 | 1/1998 |
| WO | WO 98/20001 | 5/1998 |
| WO | WO 98/57954 | 12/1998 |
| WO | WO 99/09985 | 3/1999 |
| WO | WO 99/26921 | 6/1999 |
| WO | WO 99/37304 | 7/1999 |
| WO | WO 01/25219 | 4/2001 |
| WO | WO 02/00631 | 1/2002 |
| WO | WO 02/32867 | 4/2002 |
| WO | WO 02/032867 | 4/2002 |
| WO | WO 02/055518 | 7/2002 |
| WO | WO 02/057233 | 7/2002 |
| WO | WO-03 099787 A1 | 12/2003 |
| WO | WO 2004/033428 | 4/2004 |

OTHER PUBLICATIONS

Dionne "Clinical anlgesic . . . " CA 131 :75 (1999)Alvaro et al. "Preparation of piperidinyl . . . " CA 139:179976 (2003).*

Alvaro et al. "Preparation of piperidinylcarboximide . . . " CA139:633660 (2003).*

Takahashi et a. "Preparation of N-arylmethodycarbonyl . . . " CA 140:16648 (2003).*

Davis, David T., "Synthesis A. Biological Activity of a Series of Piperazin-2, 3-Biones," Journal of Antibiotics, vol. XLII, No. 3, 1989, pp. 367-373.

Rupniak et al. "Differential inhibition of foot tapping and chromodacyorrhoea in gerbils by CNS penetrant and non-penetrant tachykinin NK, receptor antagonists." European Journal of Pharmacology 265:179-183 (1994).

Megens, A., et al. J. Pharmacology and Experimental Therapeutics 302(2):696-709 (2002).

Challet, E., et al. Neuropharmacology 40(3):408-415 (2001).

Romerio, et al. Clinical Pharmacology and Therapeutics 66(5):522-527 (1999).

Pacher, P., et al. "Review of Cardiovascular Effects of Fluoxctine, A Selective Serotonine Reuptake Inhibitor, Compared to Tricyclic Antidepressants."Current Medicinal Chemistry, 5, 381-390, 1998.

* cited by examiner

PIPERIDYLCARBOXAMIDE DERIVATIVES AND THEIR USE IN THE TREATMENT OF TACHYKININ-MEDIATED DISEASES

CROSS REFERENCES TO RELATED APPLICATIONS

This application is a 371 Application of PCT/GB03/00499, filed 5 Feb. 2003, which claims priority to GB Application Serial Nos. 0203021.1 and 0203019.5, both filed 8 Feb. 2002.

The present invention relates to piperidine derivatives, to processes for their preparation, to pharmaceutical compositions containing them and to their medical use.

In particular the invention relates to novel compounds which are potent and specific antagonists of tachykinins, including substance P and other neurokinins.

WO 99/37304 discloses interalia some 2-aryl-1,4-disubstituted piperidine derivatives as factor Xa inhibitors. Such compounds are useful as inhibitors of blood coagulation in mammalian species.

WO 97/16440 and WO 02/32867 disclose certain 2-aryl-1,4-disubstituted piperidines as NK1 antagonists.

However, in the above cited documents there is neither disclosure nor suggestion of any compound as claimed herein.

Thus, the present invention provides compounds of formula (I)

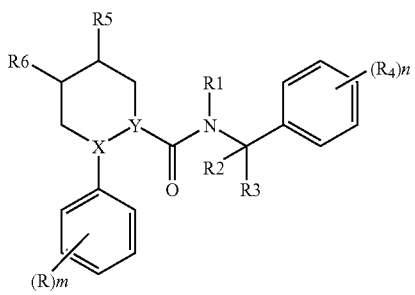

wherein
R represents halogen or $C_{1-4}$ alkyl;
$R_1$ represents hydrogen or $C_{1-4}$ alkyl;
$R_2$ represents hydrogen, $C_{1-4}$ alkyl or $R_2$ together with $R_3$ represents $C_{3-7}$ cycloalkyl;
$R_3$ represents hydrogen, $C_{1-4}$ alkyl, $C_{3-7}$ cycloalkyl or $C_{3-6}$ alkenyl; or $R_1$ and $R_3$ together with nitrogen and carbon atom to which they are attached respectively represent a 5 to 6 membered heterocyclic group;
$R_4$ represents trifluoromethyl, $C_{1-4}$ alkyl, $C_{1-4}$ alkoxy, trifluoromethoxy or halogen;
$R_5$ is hydrogen and $R_6$ is $NR_7R_8$ or $R_5$ is $NR_8R_9$ and $R_6$ is hydrogen;
$R_7$ represents hydrogen or $C_{1-4}$ alkyl or $R_7$ and $R_8$ together with nitrogen to which they are attached are a saturated 5 to 7 membered heterocyclic group containing oxygen;
$R_8$ represents hydrogen, phenyl, $C_{3-7}$ cycloalkyl, $(CH2)pC(O)NR_{10}R_{11}$, a saturated 5 to 7 membered heterocyclic group containing 1 to 3 heteroatoms selected from oxygen, sulphur and nitrogen and optionally substituted by $C_{1-4}$ alkyl, $S(O)_2C_{1-4}$ alkyl or $C(O)C_{1-4}$ alkyl, a 5 membered heteroaryl group containing 1 to 3 heteroatoms selected from oxygen, sulphur and nitrogen and optionally substituted by $C_{1-4}$ alkyl $S(O)_2C_{1-4}$ alkyl or $C(O)C_{1-4}$ alkyl or $R_8$ represents a 6 membered heteroaryl group containing 1 to 3 nitrogen atoms and optionally substituted by $C_{1-4}$ alkyl, $S(O)_2C_{1-4}$ alkyl or $C(O)C_{1-4}$ alkyl; or $R_8$ is a $C_{1-6}$ alkyl group optionally substituted by one or two groups selected from fluorine, phenyl(optionally substituted by $C_{1-4}$ alkyl, $C(O)C_{1-4}$ alkyl or halogen), =O, $C_{3-7}$ cycloalkyl, hydroxy, amino, dimethylamino, aminocarbonyl, $C_{1-4}$ alkoxy or trifluoromethyl;
$R_9$ is hydrogen, $C_{1-4}$ alkyl or $R_9$ and $R_8$ together with nitrogen to which they are attached are a 5 to 7 membered heterocyclic group optionally containing another heroatom selected from oxygen, sulphur and nitrogen and optionally substituted by one or two groups selected from $C_{1-4}$ alkyl, =O, $S(O)_2C_{1-4}$ alkyl, $C(O)C_{3-7}$ cycloalkyl or $C(O)C_{1-4}$ alkyl;
$R_{10}$ and $R_{11}$ are independently hydrogen or $C_{1-4}$ alkyl group;
X represents a nitrogen atom and Y is CH or X represents CH and Y is nitrogen;
m is zero or an integer from 1 to 3;
n is an integer from 1 to 3;
p is zero, 1 or 2;

and pharmaceutically acceptable salts and solvates thereof.

Suitable pharmaceutically acceptable salts of the compounds of general formula (I) include acid addition salts formed with pharmaceutically acceptable organic or inorganic acids, for example hydrochlorides, hydrobromides, sulphates, alkyl- or arylsulphonates (e.g. methanesulphonates or p-toluenesulphonates), phosphates, acetates, citrates, succinates, tartrates, trifluoroacetates, lactates, fumarates, malates and maleates.

The solvates may, for example, be hydrates.

References hereinafter to a compound according to the invention include both compounds of formula (I) and their pharmaceutically acceptable acid addition salts together with pharmaceutically acceptable solvates.

Suitable pharmaceutical acceptable salts of the compounds of general formula (I) may be obtained in a crystalline form and/or in an amorphous form or as a mixture thereof.

It will be appreciated by those skilled in the art that the compounds of formula (I) contain at least two chiral centres (namely the carbon atom shown as * in the formulae from 1a to 4h).

Thus, when X is CH, Y is nitrogen, $R_5$ is hydrogen and $R_6$ is $NR_7R_8$, the chiral centres may be represented by the formulae (1a, 1b, 1c e 1d).

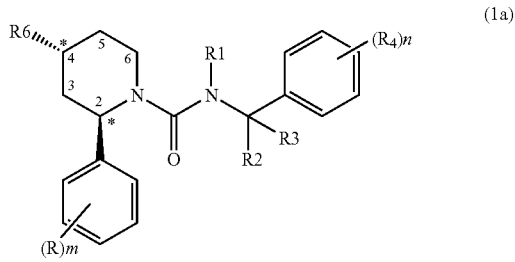

-continued
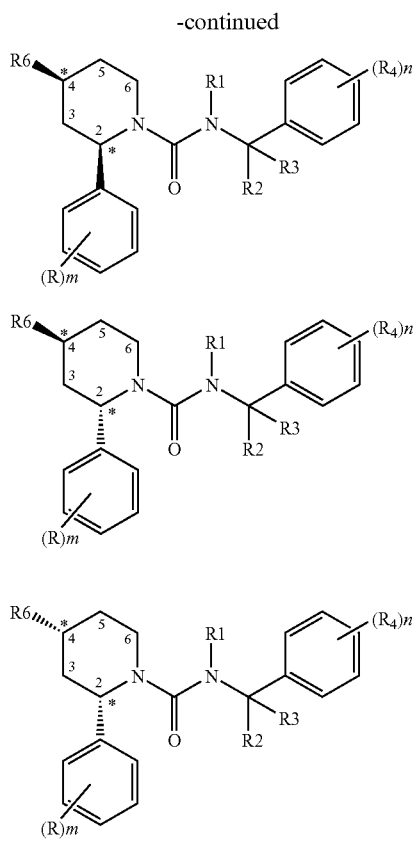
When Y is CH and X is nitrogen, $R_6$ is hydrogen and $R_5$ is $NR_7R_8$, the chiral centres may be represented by the formulae (2a, 2b, 2c and 2d).
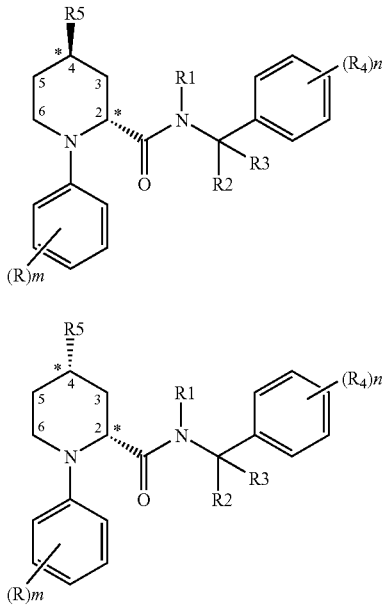
When Y is CH and X is nitrogen and $R_5$ is hydrogen and $R_6$ is $NR_7R_8$ the chiral centres may be represented by the formulae (3a, 3b, 3c and 3d).
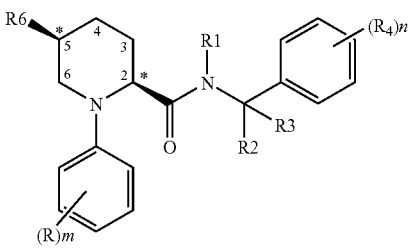
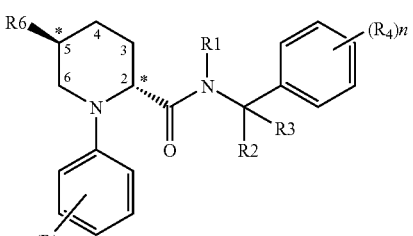
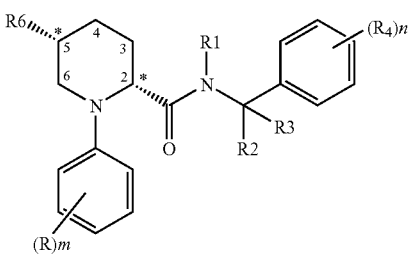

When Y is nitrogen and X is CH and $R_5$ is $NR_7R_8$ and $R_6$ is hydrogen the chiral centres may be represented by the formulae (4a, 4b, 4c and 4d).

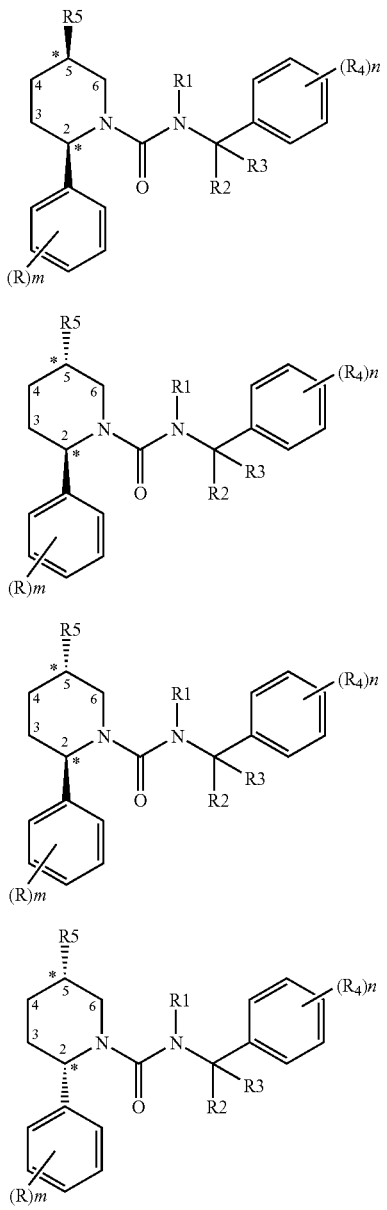

The wedge shaped bond indicates that the bond is above the plane of the paper and it corresponds to the β configuration. The broken bond indicates that the bond is below the plane of the paper and it corresponds to the α configuration.

In the specific compounds named below when Y is CH and X is nitrogen, the β configuration at the 2 position of the piperidine ring corresponds to the S configuration and the β configuration at the 4 position of the piperidine ring corresponds to the R configuration. The α configuration at the 2 position of the piperidine ring corresponds to the R configuration and the α configuration at the 4 position of the piperidine ring corresponds to the S configuration.

In the specific compounds named below when Y is nitrogen and X is CH, the β configuration at the 2 position of the piperidine ring corresponds to the R configuration and the β configuration at the 4 position of the piperidine ring corresponds to the S configuration. The α configuration at the 2 position of the piperidine ring corresponds to the S configuration and the α configuration at the 4 position of the piperidine ring corresponds to the R configuration.

The configuration of the chiral carbon atoms of the piperidine ring shown in 1a, 1c, 2b, 2c, 3b, 3c, 4b and 4c, is hereinafter referred to as anti configuration and in formulae 1b, 1d, 2a, 2d, 3a, 3d, 4a and 4d as the syn configuration.

The assignment of the R or S configuration at the 2 and the 4 positions has been made according to the rules of Cahn, Ingold and Prelog, Experientia 1956, 12, 81.

Further asymmetric carbon atoms are possible in the compounds of formula (I). Thus, when $R_2$ and $R_3$ are not the same group, the compounds of formula (I) possess at least 3 asymmetric carbon atoms.

It is to be understood that all stereoisomeric forms, including all enantiomers, diastereoisomers and all mixtures thereof, including racemates, are encompassed within the scope of the present invention and the reference to compounds of formula (I) includes all stereoisomeric forms unless otherwise stated.

Furthermore, some of the crystalline forms of the compounds of structure (I) may exist as polymorphs, which are included in the present invention.

The term $C_{1-4}$ alkyl as used herein as a group or a part of the group refers to a straight or branched alkyl group containing from 1 to 4 carbon atoms; examples of such groups include methyl, ethyl, propyl, isopropyl, n-butyl, isobutyl, tert-butyl, dimethylpropyl, 1-methylethyl or 2-methyl propyl.

The term $C_{1-6}$ alkyl is meant to include $C_{1-4}$ alkyl and the higher homologues thereof having 5 or 6 carbon atoms such as for example pentyl, 2-methylbutyl, hexyl, 2-methylpentyl or dimethylpropyl.

The term $C_{3-6}$ alkenyl group refers to a straight or branched alkenyl group containing from 3 to 6 carbon atoms; examples of such groups include 2-propenyl, 1-propenyl, isopropenyl, 2-butenyl, 2-pentenyl, 2-hexenyl and the like.

When $R_1$ and $R_3$ together with nitrogen and carbon atom to which they are attached respectively represent a 5 to 6 membered heterocyclic group, this group is saturated or contains a single double bond. This may be a 3,6-dihydro-2H-pyridin-1-yl, a piperidin-1-yl or a pyrrolidin-1-yl group.

When $R_5$ is a 5 or 6 membered heteroaryl group according to the invention it includes furanyl, thiophenyl, imidazolyl, thiazolyl, oxazolyl, pyridyl or pyrimidinyl.

When $R_7$ and $R_8$ together with nitrogen to which they are attached represent a 5 to 7 membered heterocyclic group containing oxygen this group may be a morpholinyl (e.g. morpholino), homomorpholinyl, 1,3-oxazolidinyl.

When $R_9$ and $R_8$ together with nitrogen to which they are attached is a 5 to 7 membered heterocyclic group optionally containing another heteroatom selected from oxygen, sulphur and nitrogen, this group includes piperidinyl, piperazinyl, morpholinyl, pyrazolidinyl, imidazolidinyl or pyrrolidinyl and the like.

When $R_8$ is saturated 5 to 7 membered heterocyclic group according to the invention it includes piperidinyl, piperazinyl, morpholinyl, pyrazolidinyl, imidazolidinyl or pyrrolidinyl, 1,3 dioxolan-yl and the like.

The term $C_{3-7}$ cycloalkyl group means a non aromatic monocyclic hydrocarbon ring of 3 to 7 carbon atoms such as, for example, cyclopropyl, cyclobutyl, cyclopentyl, cyclohexyl or cycloheptyl.

The term halogen refers to a fluorine, chlorine, bromine or iodine atom.

The term $C_{1-4}$ alkoxy group may be a straight chain or a branched chain alkoxy group, for example methoxy, ethoxy, propoxy, prop-2-oxy, butoxy, but-2-oxy or methylprop-2-oxy.

A group of preferred compounds of the invention is that in which $R_6$ is $NR_7R_8$ and $R_5$ is hydrogen, Y is nitrogen and X is CH or wherein $R_6$ is hydrogen and $R_5$ is $NR_8R_9$, Y is CH and X is nitrogen. These compounds are represented by the formulae (1) and (2) respectively, wherein R, $R_1$, $R_2$, $R_3$, $R_4$, $R_5$, $R_6$, m and n have the meanings defined for compounds of formula (I).

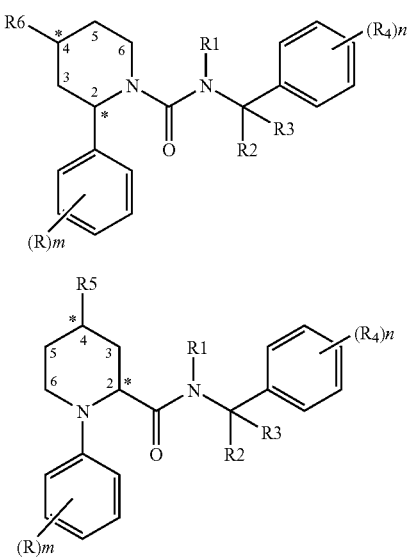

When Y is nitrogen and X is CH, a preferred group of compounds of formula (I) is that in which the carbon atom at the 2-position of the piperidine ring is in the β configuration.

A preferred group of compounds of formula (I) is that in which the substituents of the piperidine ring are in the syn configuration.

R is preferably a halogen (e.g. fluorine) and/or a $C_{1-4}$ alkyl (e.g. methyl) group and m is preferably zero or an integer from 1 to 2.

$R_1$ is preferably a methyl group.

$R_2$ is preferably a hydrogen atom or a methyl group.

$R_3$ is preferably a hydrogen atom or a methyl group.

$R_4$ is preferably a trifluoromethyl group and/or halogen (i.e. chlorine) and n is preferably 2.

$R_5$ is preferably hydrogen, $NH(C_{3-7}$ cycloalkyl), $NH(C_{1-4}$alkyl $C_{3-7}$ cycloalkyl), 1-piperazinyl(optionally substituted by one or two groups selected from $C_{1-4}$ alkyl, =O, $S(O)_2C_{1-4}$alkyl, $C(O)C_{3-7}$ cycloalkyl or $C(O)C_{1-4}$ alkyl); piperidyl (optionally substituted by one or two groups selected from $C_{1-4}$ alkyl, =O,) or morpholino.

$R_6$ is preferably hydrogen, $N(C_{1-6}$alkyl$)_2$, $NH(C_{1-6}$alkyl), $NH(CH_2)pC(O)NR_{10}R_{11}$ wherein p is 1 or 2 and $R_9$ and $R_{10}$ are independently hydrogen or methyl, $NH(C_{1-6}$ alkyltrifluoromethyl), $NH(C_{1-6}$alkyl$C_{1-4}$alkoxy), $NH(C_{1-6}$alkylfluorine), $N(C_{1-6}$ alkyl)($C_{1-6}$ alkylfluorine), $NH(C_{1-6}$ alkylphenyl), $NH(C_{3-7}$cycloalkyl), NH(piperidyl), $NH(C_{1-6}$ alkyl aminocarbonyl), $NH(C_{1-6}$ alkyl-1,3 dioxolan-yl) or morpholino.

$R_7$ is preferably a hydrogen atom or a methyl group.

$R_8$ is preferably hydrogen, $C_{1-6}$ alkyl, $C_{3-7}$ cycloalkyl, $CH2C(O)NH_2$, $C_{1-6}$ alkyl trifluoromethyl, $C_{1-6}$ alkyl$C_{1-4}$ alkoxy, $C_{1-6}$ alkylfluorine, $C_{1-6}$ alkylphenyl, piperidyl, $C_{1-6}$ alkyl aminocarbonyl, $C_{1-6}$ alkyl 1,3 dioxolanyl.

$R_9$ is preferably a hydrogen atom or a methyl group.

$R_{10}$ is preferably a hydrogen atom or a methyl group.

$R_{11}$ is preferably a hydrogen atom or a methyl group.

A preferred class of compounds of formula (I) is that wherein each R is independently a halogen (e.g. fluorine) or a $C_{1-4}$ alkyl (e.g. methyl) group, wherein m is 0, 1 or 2. More preferably m is 1 or 2. Within this class, those wherein R is at the 2 and/or 4 position in the phenyl ring are particularly preferred.

Compounds of formula (I), wherein n is 2, represent a preferred class of compounds and within this class the groups $R_4$ are preferably at the 3 and 5 position in the phenyl ring.

Further preferred compounds of formula (I) are those wherein $R_6$ is $NR_7R_8$ and $R_5$ is hydrogen, Y is nitrogen and X is CH or wherein $R_6$ is hydrogen and $R_5$ is $NR_8R_9$, Y is CH and X is nitrogen;

$R_7$ is hydrogen or methyl;

$R_8$ is methyl, ethyl, dimethylpropyl, cyclopropyl, cyclobutyl, $CH_2C(O)NH_2$, piperidinyl, 1-methyl-piperidinyl, methyl substituted by a group selected from phenyl, cyclopropyl, 4-acetyl-piperazino, fluorine, methoxy, trifluoromethyl and 1,3 dioxolanyl;

$R_9$ is hydrogen or methyl;

$R_9$ and $R_8$ together with nitrogen to which they are attached is 1-piperazinyl, acetyl-1-piperazinyl, morpholino;

$R_7$ and $R_8$ together with nitrogen to which they are attached is morpholino;

R is independently fluorine or methyl;

$R_4$ is trifluoromethyl and/or chloride;

m is 1 or 2;

n is 2.

Preferred compounds according to the invention are:

4-(2,2-Dimethyl-propylamino)-2-(4-fluoro-2-methyl-phenyl)-piperidine-1-carboxylic acid, [1-(R)-(3,5-bis-trifluoromethyl-phenyl)-ethyl]-methylamide;

Ethylamino-2-(4-fluoro-2-methyl-phenyl)-piperidine-1-carboxylic acid [1-(R)-(3,5-bis-trifluoromethyl-phenyl)-ethyl]-methylamide;

4-Dimethylamino-2-(4-fluoro-2-methyl-phenyl)-piperidine-1-carboxylic acid [1-(R)-(3,5-bis-trifluoromethyl-phenyl)-ethyl]-methylamide;

4-Dimethylamino-2-(R)-(4-fluoro-2-methyl-phenyl)-piperidine-1-carboxylic acid (3,5-bis-trifluoromethyl-benzyl)-methylamide;

4-(2-Fluoroethyl)-amino-2-(4-fluoro-2-methyl-phenyl)-piperidine-1-carboxylic acid [1-(R)-(3,5-bis)-trifluoromethyl-phenyl)-ethyl]-methylamide;

4-(2-Fluoro-ethylamino)-2-(4-fluoro-2-methyl-phenyl)-piperidine-1-carboxylic acid (3,5-bis-trifluoromethyl-benzyl)-methylamide;

4-(N-2-Fluoroethyl-N-methylamino)-2-(4-fluoro-2-methyl-phenyl)-piperidine-1-carboxylic acid, (3,5-bis-trifluoromethyl-benzyl)-methylamide;

2-(4-Fluoro-2-methyl-phenyl)-4-(2-methoxyethylamino)-piperidine-1-carboxylic acid [1-(R)-(3,5-bis-trifluoromethyl-phenyl)-ethyl]-methylamide;

2-(4-Fluoro-2-methyl-phenyl)-4-methylamino-piperidine-1-carboxylic acid [1-(R)-(3,5-bis-trifluoromethyl-phenyl)-ethyl]-methylamide;

2-(4-Fluoro-2-methyl-phenyl)-4-methylamino-piperidine-1-carboxylic acid (3,5-bis-trifluoromethyl-benzyl)-methylamide;

2-(4-Fluoro-2-methyl-phenyl)-4-methylamino-piperidine-1-carboxylic acid (3,5-bis-trifluoromethyl-benzyl)-methylamide;

4-Amino-2-(4-fluoro-2-methyl-phenyl)-piperidine-1-carboxylic acid (3,5-bis-trifluoromethyl-benzyl)-methylamide;

4-Cyclobutylamino-2-(4-fluoro-2-methyl-phenyl)-piperidine-1-carboxylic acid [1-(R)-(3,5-bis)-trifluoromethyl-phenyl)-ethyl]-methylamide;

4-Cyclopropylamino-2-(4-fluoro-2-methyl-phenyl)-piperidine-1-carboxylic acid [1-(R)-(3,5-bis-trifluoromethyl-phenyl)-ethyl]-methylamide;

2-(4-Fluoro-2-methyl-phenyl)-4-[methyl-(1-methyl-piperidin-4-yl)amino]-piperidine-1-carboxylic acid [1-(R)-(3,5-bis-trifluoromethyl-phenyl)-ethyl]-methyl-amide;

4-Benzylamino-2-(4-fluoro-2-methyl-phenyl)-piperidine-1-carboxylic acid (3,5-bis-trifluoromethyl-benzyl)-methylamide;

4-[(1,3-Dioxolan-2-yl)-methyl]-amino-2-(4-fluoro-2-methyl-phenyl)-piperidine-1-carboxylic acid, (3,5-bis-trifluoromethyl-benzyl)-methylamide;

4-(-N-2-Fluoroethyl-N-methylamino)-2-(R)-(4-fluoro-2-methyl-phenyl)-piperidine-1-carboxylic acid (3,5-bis-trifluoromethyl-benzyl)-methylamide;

4-(Carbamoylmethyl-amino)-2-(4-fluoro-2-methyl-phenyl)-piperidine-1-carboxylic acid (3,5-bis-trifluoromethyl-benzyl)-methylamide;

2-(4-Fluoro-2-methyl-phenyl)-4-morpholino-piperidine-1-carboxylic acid (3,5-bis-trifluoromethyl-benzyl)-methylamide;

2-(4-Fluoro-2-methyl-phenyl)-4-morpholino-piperidine-1-carboxylic acid 1-[(R)-(3,5-bis-trifluoromethyl-phenyl)-ethyl]-methylamide;

2-(4-Fluoro-2-methyl-phenyl)-4-morpholino-piperidine-1-carboxylic acid 1-[(S)-(3,5-bis-trifluoromethyl-phenyl)-ethyl]-methylamide;

4-Cyclopropylamino-1-(4-fluoro-2-methyl-phenyl)-piperidine-2-carboxylic acid (3,5-dichloro-benzyl)-methylamide;

4-(4-Acetyl-piperazin-1-yl)-1-(4-fluoro-2-methyl-phenyl)-piperidine-2-carboxylic acid (3,5-dichloro-benzyl)-methylamide;

4-Cyclopropylamino-1-(4-fluoro-2-methyl-phenyl)-piperidine-2-carboxylic acid [1-(R)-3,5-bis-trifluoromethyl-phenyl)-ethyl]-methylamide;

4-Cyclopropylmethylamino-1-(4-fluoro-2-methyl-phenyl)-piperidine-2-carboxylic acid (3,5-ditrifluoromethyl-benzyl)-methylamide;

1-(4-Fluoro-2-methyl-phenyl)-4-morpholino-piperidine-2-carboxylic acid (3,5-bis-trifluoromethyl-benzyl)-methylamide;

4-(4-Acetylpiperazinyl)-1-(4-fluoro-2-methyl-phenyl)-piperidine-2-carboxylic acid, (3,5-bis-trifluoromethyl-benzyl)-methylamide;

diastereoisomers and acceptable pharmaceutical salts thereof.

Particularly preferred compounds of the invention are:

4-(S)-Dimethylamino-2-(R)-(4-fluoro-2-methyl-phenyl)-piperidine-1-carboxylic acid [1-(R)-(3,5-bis-trifluoromethyl-phenyl)-ethyl]-methylamide hydrochloride;

4-(S)-Dimethylamino-2-(R)-(4-fluoro-2-methyl-phenyl)-piperidine-1-carboxylic acid (3,5-bis-trifluoromethyl-benzyl)-methylamide hydrochloride;

4-(S)-(2-Fluoroethyl)-amino-2-(R)-(4-fluoro-2-methyl-phenyl)-piperidine-1-carboxylic acid [1-(R)-(3,5-bis)-trifluoromethyl-phenyl)-ethyl]-methylamide hydrochloride;

4-(S)-(2-Fluoro-ethylamino)-2-(R)-(4-fluoro-2-methyl-phenyl)-piperidine-1-carboxylic acid (3,5-bis-trifluoromethyl-benzyl)-methylamide hydrochloride. 4-(S)-Dimethylamino-2-(R)-(4-fluoro-2-methyl-phenyl)-piperidine-1-carboxylic acid [1-(R)-(3,5-bis-trifluoromethyl-phenyl)-ethyl]-methylamide hydrochloride;

4-(S)-Dimethylamino-2-(R)-(4-fluoro-2-methyl-phenyl)-piperidine-1-carboxylic acid (3,5-bis-trifluoromethyl-benzyl)-methylamide hydrochloride;

4-(S)-(2-Fluoroethyl)amino)-2-(R)-(4-fluoro-2-methyl-phenyl)-piperidine-1-carboxylic acid [1-(R)-(3,5-bis)-trifluoromethyl-phenyl)-ethyl]-methylamide hydrochloride;

4-(S)-(2-Fluoro-ethylamino)-2-(R)-(4-fluoro-2-methyl-phenyl)-piperidine-1-carboxylic acid (3,5-bis-trifluoromethyl-benzyl)-methylamide hydrochloride.

The compounds of the invention are antagonists of tachykinins, including substance P and other neurokinins, both in vitro and in vivo and are thus of use in the treatment of conditions mediated by tachykinins, including substance P and other neurokinins.

The compounds of the present invention have also activity as serotonin re-uptake inhibitors.

Tachykinins are a family of peptides that share a common carboxyl-terminal sequence (Phe-X-Gly-Leu-Met-NH2). They are actively involved in the physiology of both lower and advanced lifeforms. In mammalian lifeforms, the main tachykinins are substance P (SP), Neurokinin A (NKA) and Neurokinin B (NKB) which act as neurotransmitters and neuromodulators. Mammalian tachykinins may contribute to the pathophysiology of a number of human diseases.

Three types of tachykinins receptors have been identified, namely NK1(SP-preferring), NK2 (NKA-preferring) and NK3 (NKB-preferring) which are widely distributed throughout the central nervous (CNS) and peripheral nervous system.

Particularly, the compounds of the invention are antagonists of the NK1 receptor.

By virtue of their efficacy as tachykinins receptor (expecially NK1 receptor) antagonists, the compounds of the present invention are particularly useful for the treatment of CNS disorders and psychotic disorders, in particular in the treatment or prevention of depressive states and/or in the treatment of anxiety.

$NK_1$-receptor binding affinity has been determined in vitro by measuring the compounds' ability to displace [3H]-substance P (SP) from recombinant human $NK_1$ receptor expressed in Chinese Hamster Ovary (CHO) cell membranes and from gerbil and marmoset brain cortex homogenates.

Membrane preparation from hNK1-CHO cells were performed essentially as described by Beattie et al. (Br. J. Pharmacol, 116:3149-3157, 1995).

hNK1-CHO cells were harvested in phosphate buffered saline (PBS) containing 5 mM EDTA and centrifuged at 913 g for 8 min at 4° C. Cells were then re-suspended in 10 volumes of membrane-preparation buffer (HEPES 50 mM, pH 7.4, containing 0.1 mM leupeptin, 40 µg/ml bacitracin, 1 mM EDTA, 1 mM Pefabloc and 2 µM pepstatin A) and homogenised. The suspension was centrifuged at 48,000 g for 20 minutes at 4° C. The final pellet was re-suspended in 10 volumes of membrane preparation buffer and re-homogenised. Suspensions of membrane were then frozen at −80° C. until required.

The assay volume of 200 µl consisted of 2 µl of DMSO or increasing concentrations of test compound dissolved in DMSO (1 pM-1 µM final concentration), 100 µl of [3H]—SP (0.5 nM final concentration), and 100 µl of membrane suspension (8 µg of protein per well) in incubation buffer (containing 50 mM HEPES, pH 7.4, 3 mM MnCl2, and 0.02% BSA). The incubation was carried out at room temperature for 40 min. Non-specific binding was defined by the addition of cold SP (1 µM). The reaction was stopped by rapid filtration. Filters were washed 5 times with 200 µl of ice-cold 0.9% w/v NaCl, and radioactivity was counted in a microplate scintillation counter. In each experiment, every concentration of displacer was tested in duplicate.

Mongolian gerbil (60 g, Charles River) and common marmoset (Callithrix jacchus, 300-400 g, GSK colony, Verona, Italy) brain cortex homogenates were prepared as follows: fresh tissues were weighed, crumbled and homogenised in 10 volumes of membrane-preparation buffer. The homogenate was then centrifuged at 48,000 g for 20 minutes, and the pellet was washed once more by resuspension in 10 volumes of membrane preparation buffer and centrifugation at 48,000 g for 20 minutes. The final pellet was re-suspended in 7-10 volumes of membrane preparation buffer and subdivided in aliquots frozen at −80° C. until use.

The assay volume of 400 µl consisted of 100 µl of incubation buffer (containing 50 mM HEPES, pH 7.4, 3 mM MnCl2, and 0.02% BSA), 4 µl of DMSO or increasing concentrations of test compound dissolved in DMSO (1 pM-1 µM final concentration), 100 µl of [3H]—SP (0.5 nM-0.8 nM final concentration) in incubation buffer and 200 µl of membrane suspension (0.6 mg protein for gerbil, and 0.8 mg protein for marmoset) in incubation buffer containing 2 µg/ml leupeptin, 20 µg/ml bacitracin and 0.5 µM phosphoramidon. The incubation proceeded at room temperature for 60 min. Non-specific binding was defined by the addition of cold SP (1 µM). The reaction was stopped by rapid filtration. Filters were washed 3 times with 1 ml ice cold wash buffer (containing 50 mM HEPES, pH 7.4, and 3 mM MnCl2), and radioactivity was counted in a liquid scintillation counter.

The potency of test compounds to inhibit SP or $GR_{73632}$-induced increase of [Ca2+]i in hNK1/CHO cells was determined in functional experiments by using FLIPR (fluorimetric imaging plate reader) technology. hNK1/CHO cells were seeded at a density of 60,000 cells per well and cultured overnight in Ham's F-12 medium supplemented with 10% (v/v) heat-inactivated foetal bovine serum and 2 mM glutamine. The cells were then incubated for the labelling in the culture medium containing the fluorescent calcium indicator Fluo-4 AM (2 µM), the organic anions transport blocker probenecid (5 mM), and HEPES (20 mM) for 30 min in a humidified atmosphere of 5% CO2. After washing with Hanks' Balanced Salts Solution (HBSS) containing 20 mM HEPES and 2.5 mM probenecid, the cells were incubated for 60 min at 37 C in wash buffer containing 0.02% BSA either in the absence (control) or in the presence of test compounds. The plates were then placed into a FLIPR to monitor cell fluorescence (ex488 nm, em=510-570 nm) before and after the addition of different concentrations of SP or $GR_{73632}$ in assay buffer. Experiments were carried out by using a laser setting of 1.0 W and a 0.4 sec charge coupled device (CCD) camera shutter speed.

Compounds of the invention have also been found to exhibit anxiolytic activity in conventional tests. For example in marmoset human threat test (Costall et al., 1988).

Human Serotonin Transporter (hSERT) binding affinity has been determined in vitro by the compounds' ability to displace [3C]—Imipramine from human serotonin transporter expressed in Human Embryonic Kidney HEK293 cell membranes (Receptor Biology Inc.). For the binding reaction, 4 nM of [3H]—Imipramine (703 GBq/mmol, Amersham) were incubated with 0.02 mg/ml of cell membrane and the compound to be tested at different concentrations (7 concentration points) in 50 mM Tris HCl, pH 7.5, 120 mM of NaCl and 5 mM KCl. The reaction was performed for 60 min at 4° C. and was terminated by filtration through GF/B Unifilters 96 wells/case (presoaked in 0.5% PEI) using a Cell Harvester (Packard). Scintillation fluid was added to each filtered spot and radioactivity was determined using a scintillation counter (TopCount (Packard)). Non-specific binding was determined using Imipramine (100 µM) and represents about 5% of the total binding.

Competition experiments were conducted with duplicate determination for each point. Msat601 software package was used to elaborate the competition binding data. $IC_{50}$ values were converted to $K_i$ values using Cheng-Prusoff equation.

The inhibitory activity of the compounds at the rat serotonin transporter has been determined in vitro using rSERT-LLCPK cells (LLCPK cells tranfected with the rat SERT). The cells have been plated onto 96-well plates (60000 cells/well). After 24 hr, cells have been washed in uptake buffer (Hank's balanced salt solution+20 mM Hepes) and pre-incubated for 10 min at RT with 50 µl of buffer containing the test compounds. 50 µl of 50 nM [3H] Serotonin (5HT) solution (final concentration: 25 nM [3H] 5HT) have been added and plates have been incubated for 7 min at RT, during which cells take up radiolabelled 5HT. Aspirating the solution and rapidly washing the cells with cold buffer has terminated the uptake.

The amount of radioactive 5HT incorporated in the cells has been then measured by adding the scintillation cocktail directly onto the cells and reading the plate in the Top Count. The data have been digitally processed to obtain the pIC50 values of the antagonists. The pKi values have been calculated using the Chen-Prusoff equation.

The action of the compounds of the invention at the $NK_1$ receptor may be determined by using conventional tests. Thus, the ability to penetrate the central nervous system and to bind at the $NK_1$ receptor was demonstrated in vivo by their inhibitory effect on the change in the behaviour induced by intracerebroventricular applied substance P in the gerbil, according to the gerbil foot tapping model as described by Rupniak & Williams, Eur. J. of Pharmacol., 265, 179-183, 1994.

Compounds of the invention are useful in the treatment of CNS disorders and psychotic disorders, in particular in the treatment or prevention of depressive states and/or in the treatment of anxiety as defined in, but not restricted to, Diagnostic Statistical of Mental Disorder (DSM) IV edition edit by American Psychiatric Association and International Classification Diseases 10th revision (ICD10).

Thus, for example, depressive states include Major Depressive Disorders (MDD), including bipolar depression, unipolar depression, single or recurrent major depressive episodes, recurrent brief depression, with or without psychotic features, catatonic features, melancholic features including anorexia, weight loss, atypical features, anxious depression, cyclothymic or postpartum onset.

Other mood disorders encompassed within the term major depressive disorders include dysthymic disorders with early or late onset and with or without atypical features, neurotic depression, post-traumatic stress disorders and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

The term anxiety includes anxiety disorders, such as panic disorders with or without agoraphobia, agoraphobia, phobias, for example, social phobias or agoraphobia, obsessive-compulsive disorder, stress disorders including post-traumatic stress disorders, generalised anxiety disorders, acute stress disorders and mixed anxiety-depression disorders.

Compounds of the invention are useful as analgesics. In particular, they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; bums; scar pain; itch and thalamic pain such as post stroke thalamic pain.

Compounds of the invention are also useful in the treatment of sleep disorders including dysomnia, insomnia, sleep apnea, narcolepsy, and circadian ritmic disorders.

Compounds of the invention are also useful in the treatment or prevention of the cognitive disorders. Cognitive disorders include dementia, amnestic disorders and cognitive disorders not otherwise specified.

Furthermore, compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds) or in the treatment of tolerance to and dependence on opiates (e.g. cannabis, heroin, morphine) or benzodiazepines; in the treatment of addiction to cocaine, sedative ipnotic, amphetamine or amphetamine-related drugs (e.g. dextroamphetamine, methylamphetamine) or a combination thereof.

Compounds of the invention are also useful as anti-inflammatory agents. In particular, they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment or prevention of schizophrenic disorders including paranoid schizophrenia, disorganised schizophrenia, catatonic schizophrenia, undifferentiated schizophrenia, residual schizophrenia.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease (GERD) such as erosive GERD and symptomatic GERD or non erosive GERD, acid indigestion, over-indulgence of food or drink, acid stomach, sour stomach, waterbrash/regurgitation, heartburn, such as episodic heartburn, nocturnal heartburn, and meal-induced heartburn, dyspepsia and functional dyspepsia.

Compounds of the invention are also useful in the treatment of gastrointestinal disorders such as irritable bowel syndrome, gastro-oesophageal reflux disease (GERD) such as erosive GERD and symptomatic GERD or non erosive GERD, acid indigestion, over-indulgence of food or drink, acid stomach, sour stomach, waterbrash/regurgitation, heartburn, such as episodic heartburn, nocturnal heartburn, and meal-induced heartburn, dyspepsia and functional dyspepsia (such as ulcer-like dyspepsia, dysmotility-like dyspepsia and unspecified dyspepsia) chronic constipation; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

The compounds of the invention are also useful in premenstrual dysphoric disorder (PMDD), in chronic fatigue syndrome and Multiple sclerosis.

Compounds of the invention have been found to exhibit anxiolytic and antidepressant activity in conventional tests. For example, in Guinea pig pups separation-induced vocalisations (Molewijk et al., 1996).

Compounds of the invention are also useful in the treatment of convulsions and epilepsy.

Compounds of the invention may be administered in combination with other active substances such as 5HT3 antagonists, serotonin agonists, selective serotonin reuptake inhibitors (SSRI), noradrenaline re-uptake inhibitors (SNRI), tricyclic antidepressants or dopaminergic antidepressants.

Suitable 5HT3 antagonists which may be used in combination with the compounds of the inventions include for example ondansetron, granisetron and metoclopramide.

Suitable serotonin agonists which may be used in combination with the compounds of the invention include sumatriptan, rauwolscine, yohimbine and metoclopramide.

Suitable SSRI which may be used in combination with the compounds of the invention include fluoxetine, citalopram, femoxetine, fluvoxamine, paroxetine, indalpine, sertraline and zimeldine.

Suitable SNRI which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

It will be appreciated that the compounds of the combination may be administered simultaneously (either in the same or different pharmaceutical formulations) or sequentially.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by tachykinins, including substance P and other neurokinins.

In an alternative or further aspect there is provided a method for the treatment of a mammal, including man, in particular in the treatment of conditions mediated by tachykinins, including substance P and other neurokinins, comprising administration of an effective amount of a compound of formula (I) or a pharmaceutically acceptable salt thereof.

It will be appreciated that reference to treatment is intended to include prophylaxis as well as the alleviation of established symptoms. Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus, compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in a conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Compounds of formula (I), and salts and solvates thereof, may be prepared by the general methods outlined hereinafter. In the following description, the groups R, $R_1$, $R_2$, $R_3$, $R_4$, $R_5$ $R_6 R_7 R_8 R_9$, $R_{10}$ or $R_{11}$ m, n and p have the meaning as previously defined for compounds of formula (I) unless otherwise stated.

Compounds of formula (I) may be prepared by reductive N-alkylation of a compound of formula (II), wherein $R_{12}$ is =O and $R_{13}$ is hydrogen or $R_{12}$ is hydrogen and $R_{13}$ is =O

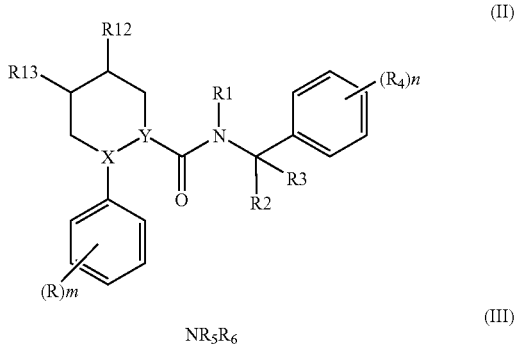

with an amine derivative (III) or salts thereof. The reaction is conveniently carried out in an aprotic solvent such as dichloroethane and in the presence of a suitable metal reducing agent such as sodium borohydride or sodium triacetoxyborohydride.

In a further embodiment of the invention, compounds of formula (I), wherein X is CH, Y is nitrogen may be prepared by reaction of a compound of formula (IV)

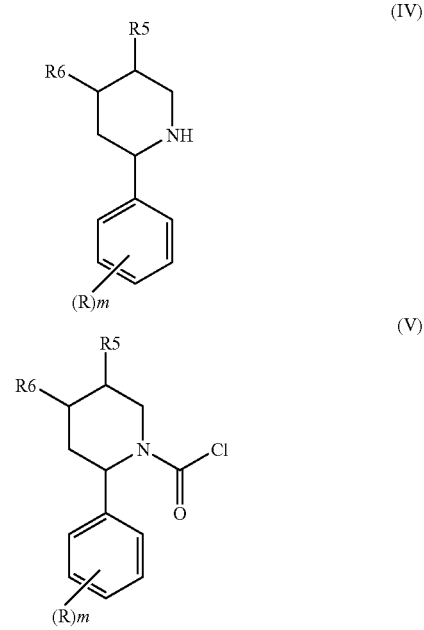

with triphosgene in an aprotic solvent such as dichloromethane and in the presence of an organic base such triethylamine to form the intermediate compound (V) which may be isolated if required, followed by reaction of compound (V) with the amine compound (VI).

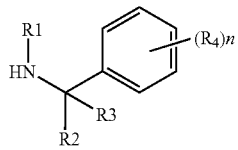

The reaction conveniently takes place in an aprotic solvent such as a hydrocarbon, a halohydrocarbon such as dichloromethane or an ether such as tetrahydrofuran optionally in the presence of a base such as a tertiary amine e.g. diisopropylethylamine.

In a further embodiment of the invention, compounds of formula (I) wherein X is nitrogen and Y is CH may be prepared by reaction of an activated derivative of the carboxylic acid of formula (VII), with amine (VI) or salts thereof, optionally in the presence of a suitable base.

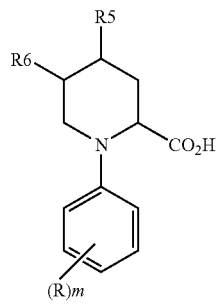

Suitable activated derivatives of the carboxyl group include the corresponding acyl halide, mixed anhydride, activated ester such as a thioester or a derivative formed between the carboxylic acid group and a coupling agent such as that used in peptide chemistry, for example O-(benzotriazol-1-yl)-N,N,N'N'-tetramethyluronium tetrafluoroborate.

The reaction is preferably carried out in an aprotic solvent such as an ether, e.g. tetrahydrofuran, a halohydrocarbon, e.g. dichloromethane, N,N-dimethylformamide or acetonitrile.

Suitable base for use in this reaction includes organic base such as triethylamine or N,N diisopropylethylamine.

The activated derivatives of the carboxylic acid (VI) may be prepared by conventional means. A particularly suitable activated derivative for use in this reaction is obtained by reaction of the carboxylic acid (II) with O-(benzotriazol-1-yl)-N,N,N'N'-tetramethyluronium tetrafluoroborate in a suitable aprotic solvent such as an ether e.g. tetrahydrofuran, a halohydrocarbon e.g. dichloromethane, an amide e.g. N,N-dimethylformamide or acetonitrile.

Compounds of formula (II), in which X is CH, Y is nitrogen may be prepared by treating compounds of formula (VIII), wherein $R_{12}$ and $R_{13}$ have the meanings defined for compounds of formula (II) wherein Ra is a nitrogen protective group,

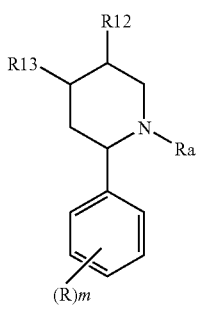

using the same procedures described above for the preparation of compounds of formula (I) from compounds of formula (IV) after removal of nitrogen protecting group Ra.

Compounds of formula (II), wherein $R_{12}$ and $R_{13}$ have the meanings defined for compounds of formula (II) and in which Y is nitrogen, X is CH, may be prepared by treating compounds of formula (IX)

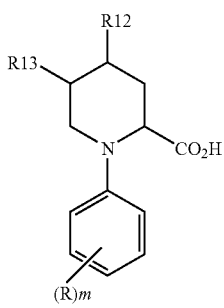

using the same procedures described above for the preparation of compounds of formula (II) from compounds of formula (VII).

Compounds of formulae (IV) and (VII) may be prepared by reductive N-alkylation of a piperidine of formula (VIII) and a carboxylic acid (IX) or esters thereof (such as methyl, ethyl and the like) respectively with an amine derivative (III) or salts thereof. The reaction is conveniently carried out in an aprotic solvent such as dichloroethane and in the presence of a suitable metal reducing agent such as sodium borohydride or sodium triacetoxyborohydride.

Compounds of formula (VIII) are either known compounds or may be prepared by analogous methods to those used for known compounds.

Thus, for example, compound (VIII) and enantiomers thereof may be prepared using Comins reaction as described in Journal American Chemical Society 1994,116, 4719-4728, followed by reduction of 2,3 dihydro-1H-pyridin-4-one derivative to piperidine-4-one derivative. The reduction may be effected using hydrogen and metal catalyst e.g. palladium on a suitable support e.g. carbon or alumina. The reaction is carried out in a solvent such as ester e.g. ethyl acetate.

Compounds of formula (IX) wherein $R_{13}$ is =O and $R_9$ is hydrogen are known compounds and they may be prepared according to the procedures as described in Bioorganic & Medicinal Chemistry Letters, Vol 2, N°11, pp 1357-1360, 1992.

Compounds of formula (IX) wherein $R_{12}$ is =O and $R_8$ is hydrogen are novel compounds and they may be prepared for example by reaction of an amine (XIV) with ethyl glyoxalate to obtain the intermediates (XIII) which may be converted into 4-oxo-tetrahydropyridine intermediates (XII) which in turn may be reduced to an intermediate of formula (XI). Said intermediate (XI) may be in turn hydrolysed, thus forming an intermediate of formula (IX).

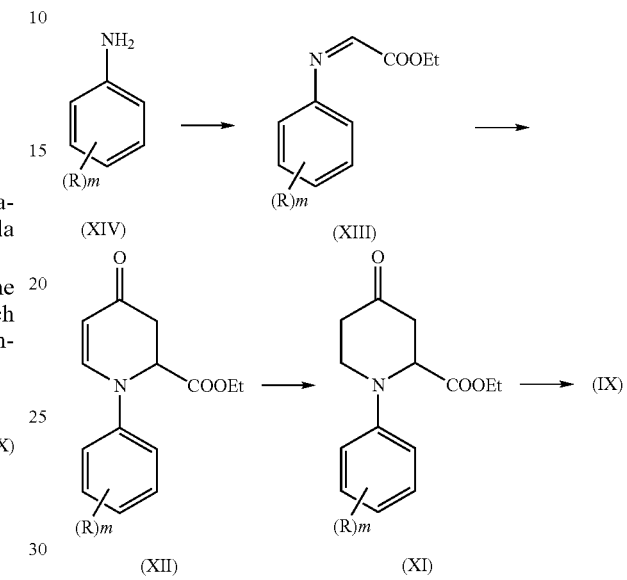

Compounds of formula (III) are known compounds or may be prepared by analogous methods to those used for known compounds.

Where it is desired to isolate a compound of formula (I) as a salt, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether or tetrahydrofuran).

Pharmaceutically acceptable salts may also be prepared from other salts, including other pharmaceutically acceptable salts of the compounds of formula (I) using conventional methods.

The compounds of formula (I) may readily be isolated in association with solvent molecules by crystallisation from or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods.

Thus, for example, specific enantiomers of the compounds of formula (I) may be obtained from the corresponding enantiomeric mixture of a compound of formula (I) using chiral HPLC procedure.

Alternatively, enantiomers of a compound of general formula (I) may be synthesised from the appropriate optically active intermediates using any of the general processes described herein.

Thus, for example the required enantiomer may be prepared by the corresponding chiral piperidin-4-one of formula (IV) using the process described above for preparing compounds of formula (I) from compounds (IV), followed by separation of the diastereomeric mixture of a compound of formula (I) using conventional procedure.

The chiral compounds (IV) may be prepared from the corresponding racemic compound (IV) using conventional procedures such as salt formation with a suitable optically active acid, separating the resultant diastereoisomeric salts by conventional means e.g. chromatography and crystallisation followed by hydrolysis of the diastereoisomeric salts.

A suitable optically active acid for use in the process is L(+)mandelic acid.

In a further embodiment of the invention the enantiomers of the compound of formula (I) may be prepared by reaction of a chiral amine (VI) using any of the processes described above for preparing compounds of formula (I) from amine (V).

The chiral amine (III) may be prepared from the corresponding racemic amine (III) using any conventional procedures such as salt formation with a suitable optically active acid.

The invention is further illustrated by the following Intermediates and Examples which are not intended as a limitation of the invention.

In the Intermediates and Examples unless otherwise stated:

Melting points (m.p.) were determined on a Buchi m.p. apparatus and are uncorrected. All temperatures refer to 0° C.

Infrared spectra (IR) were measures in chloroform or nujol solutions on a FT-IR instrument. Proton Magnetic Resonance (NMR) spectra were recorded on Varian instruments at 400 or 500 MHz, chemical shifts are reported in ppm (δ) using the residual solvent line as internal standard. Splitting patterns are designed as s, singlet; d, double; t, triple; q, quartet; m, multiplet; b, broad. Mass spectra (MS) were taken on a VG Quattro mass spectrometer. Optical rotations were determined at 20° C. with a Jasco DIP 360 Instrument (1=10 cm, cell volume=1 mL, λ=589 nm).

Flash silica gel chromatography was carried out over silica gel 230-400 mesh supplied by Merck AG Darmstadt, Germany. T.l.c. refers to thin layer chromatography on 0.25 mm silica gel plates (60F-254 Merck) and visualised with UV light.

Solutions were dried over anhydrous sodium sulphate.

Methylene chloride was redistilled over calcium hydride and tetrahydrofuran was redistilled over sodium.

The following abbreviation are used in the text: AcOEt=ethyl acetate, CH=cyclohexane; DCM=methylene chloride, DMF=N,N'-dimethylformamide, DIPEA=N,N-diisopropylethylamine, Et2O=diethyl ether, EtOH=ethanol, MeOH=methanol, TEA=triethylamine, THF=tetrahydrofuran.

Diastereoisomer A refers to a mixture of compounds having anti configuration as defined above.

Diastereoisomer B refers to a mixture of compounds having syn configuration as defined above.

Diastereoisomer 1 refers to a single diastereoisomer whose absolute configuration has not determinated.

Diastereoisomer 2 refers to a single diastereoisomer whose absolute configuration has not determinated.

Intermediate 1

1-(Benzyloxycarbonyl)-2-(4-fluoro-2-methyl-phenyl)-2,3-dihydro-4-pyridone

A small amount of iodine was added to a suspension of magnesium turnings (13.2 g) in dry THF (300 mL), at r.t., under a nitrogen atmosphere, then the mixture was vigorously refluxed for 20 minutes. To this suspension, a 15% of a solution of 2-bromo-5-fluoro-toluene (52.5 mL) in anhydrous THF (300 mL) was added. The suspension was heated under vigorous reflux until the brown colour disappeared. The remaining part of the bromide solution was added drop-wise over 1 hour to the refluxing suspension which was then stirred for a further 1 hour. This solution of Grignard reagent was then added drop-wise to the pyridinium salt obtained from benzyl chloroformate (48.7 mL) and 4-methoxypyridine (25 mL) in dry THF (900 mL) at −23° C.

The obtained solution was stirred 1 hour at −20° C. then it was warmed up to 20° C., a 10% hydrochloric acid solution (560 mL) was added and the aqueous layer was extracted with AcOEt (2×750 mL).

The combined organic extracts were washed with 5% sodium hydrogen carbonate solution (600 mL) and brine (600 mL) then partially concentrated in vacuo.

CH (400 mL) was added drop-wise over 1 hour at 20° C. and the resulting mixture was stirred 30 minutes and then filtered to give the title compound as a white solid (66 g).

IR (nujol): 1726 and 1655 (C=O), 1608(C=C) cm$^{-1}$.
NMR (d$_6$-DMSO): δ (ppm) 8.19 (d, 1H); 7.31-7.18 (m, 5H); 7.08 (m,2H); 6.94 (dt, 1H); 5.77 (d, 1H); 5.36 (d, 1H); 5.16 (2d, 2H); 3.26 (dd, 1H); 2.32 (d, 1H); 2.26 (s, 3H).

MS (ES/+): m/z=340 [MH]$^+$.

Intermediate 2

2-(4-Fluoro-2-methyl-phenyl)-piperidine-4-one

Method A:

2-Fluoro-4-methyl-benzaldehyde (4 g) was added to a solution of 4-aminobutan-2-one ethylene acetal (3.8 g) in dry benzene (50 mL) and the solution was stirred at r.t. under a nitrogen atmosphere. After 1 hour the mixture was heated at reflux for 16 hours and then allowed to cool to r.t. This solution was slowly added to a refluxing solution of p-toluenesulphonic acid (10.6 g) in dry benzene (50 mL) previously refluxed for 1 hour with a Dean-Stark apparatus. After 3.5 hours the crude solution was cooled and made basic with a saturated potassium carbonate solution and taken up with AcOEt (50 mL). The aqueous phase was extracted with AcOEt (3×50 mL) and Et2O (2×50 mL). The organic layer was dried and concentrated in vacuo to a yellow thick oil as residue (7.23 g). A portion of the crude mixture (3 g) was dissolved in a 6N hydrochloric acid solution (20 mL) and stirred at 60° C. for 16 hours. The solution was basified with solid potassium carbonate and extracted with DCM (5×50 mL). The combined organic phases were washed with brine (50 mL), dried and concentrated in vacuo to give the title compound (2.5 g) as a thick yellow oil.

Method B

L-selectride (1M solution in dry THF, 210 mL) was added drop-wise, over 80 minutes, to a solution of intermediate 1 (50 g) in dry THF (1065 mL) previously cooled to −72° C. under a nitrogen atmosphere. After 45 minutes, 2% sodium hydrogen carbonate solution (994 mL) was added drop-wise and the solution was extracted with AcOEt (3×994 mL). The combined organic phases were washed with water (284 mL) and brine (568 mL). The organic phase was dried and concentrated in vacuo to get 1-benzyloxycarbonyl-2-(4-fluoro-2-methyl-phenyl)-piperidine-4-one as a pale yellow thick oil (94 g) which was used as a crude.

This material (94 g) was dissolved in AcOEt (710 mL), then 10% Pd/C (30.5 g) was added under a nitrogen atmosphere. The slurry was hydrogenated at 1 atmosphere for 30 minutes. The mixture was filtered through Celite and the organic phase was concentrated in vacuo to give the crude 2-(4-fluoro-2-methyl-phenyl)-piperidine-4-one as a yellow oil. This material was dissolved in AcOEt (518 mL) at r.t. and racemic camphorsulphonic acid (48.3 g) was added. The mixture was stirred at r.t for 18 hours, then the solid was filtered off, washed with AcOEt (2×50 mL) and dried in vacuo for 18 hours to give 2-(4-fluoro-2-methyl-phenyl)-piperidine-4-one, 10-camphorsulfonic acid salt as a pale yellow solid (68.5 g). (M.p.: 167-169° C.-NMR ($d_6$-DMSO): δ (ppm) 9.43 (bs, 1H); 9.23 (bs, 1H); 7.66 (dd, 1H); 7.19 (m, 2H); 4.97 (bd, 1H); 3.6 (m, 2H); 2.87 (m, 3H); 2.66 (m, 1H); 2.53 (m, 2H); 2.37 (s+d, 4H); 2.22 (m, 1H); 1.93 (t, 1H); 1.8 (m, 2H); 1.26 (m, 2H); 1.03 (s, 3H); 0.73 (s, 3H).

This material (68.5 g) was suspended in AcOEt (480 mL) and stirred with a saturated sodium hydrogen carbonate (274 mL). The organic layer was separated and washed with further water (274 mL). The organic phase was dried and concentrated in vacuo to give the title compound (31 g) as a yellow-orange oil.

NMR ($d_6$-DMSO): δ (ppm) 7.49 (dd, 1H); 7.00 (m, 2H); 3.97 (dd, 1H); 3.27 (m, 1H); 2.82 (dt, 1H); 2.72 (bm, 1H); 2.47 (m, 1H); 2.40 (m, 1H); 2.29 (s, 3H); 2.25 (dt, 1H); 2.18 (m, 1H).

MS (ES/+): m/z=208 [MH]$^+$.

Intermediate 3

2-(4-Fluoro-2-methyl-phenyl)-4-oxo-piperidine-1-carboxylic acid (3,5-bis-trifluoromethyl-benzyl)-methylamide A solution of triphosgene (1.43 g) dissolved in dry DCM (10 mL) was added to a solution of intermediate 2 (2.5 g) and DIPEA (8.4 mL) in dry DCM (20 ML) previously cooled to 0° C. under a nitrogen atmosphere. The solution was stirred at 0° C. for 2 hours, then (3,5-bis-trifluoromethyl-benzyl)-methylamine hydrochloride (5.63 g) and DIPEA (3.34 mL) were added. The mixture was stirred under nitrogen at r.t. for 14 hours. The mixture was taken up with AcOEt (50 mL), washed with cold 1N hydrochloric acid solution (3×20 mL) and brine (10 mL). The organic layer was dried and concentrated in vacuo to a residue which was purified by flash chromatography (AcOEt/CH 3:7) to give the title compound as a white foam (3.85 g).

IR (nujol): 1721 and 1641 (C=O) cm$^{-1}$.

NMR ($d_6$-DMSO): δ (ppm) 7.96 (s, 1H); 7.76 (s, 2H); 7.25 (dd, 1H); 6.97 (dd, 1H); 6.90 (dt, 1H); 5.22 (t, 1H); 4.59 (d, 1H); 4.43 (d, 1H); 3.63-3.49 (m, 2H); 2.79 (s, 3H); 2.69 (m, 2H); 2.49 (m, 2H); 2.26 (s, 3H).

MS (ES/+): m/z=491 [MH]$^+$.

Intermediate 4

2-(R)-(4-Fluoro-2-methyl-phenyl)-4-oxo-piperidine-1-carboxylic acid [1-(R)-3,5-bis-trifluoromethyl-phenyl)-ethyl]-methylamide (4a) and 2-(S)-(4-Fluoro-2-methyl-phenyl)-4-oxo-piperidine-1-carboxylic acid [1-(R)-3,5-bis-trifluoromethyl-phenyl)-ethyl]-methylamide (4b)

Method A:

A solution of triphosgene (147 mg) dissolved in dry DCM (5 mL) was added drop-wise to a solution of intermediate 2 (250 mg) and DIPEA (860 μL) in dry DCM (15 mL) previously cooled to 0° C. under a nitrogen atmosphere. After 2 hours, [1-(R)-3,5-bis-trifluoromethyl-phenyl)-ethyl]-methylamine hydrochloride (503 mg) and DIPEA (320 μL) in dry-acetonitrile (20 mL) were added and the mixture was heated to 70° C. for 16 hours. Further [1-(R)-(3,5-bis-trifluoromethyl-phenyl)-ethyl]-methylamine hydrochloride (170 mg) and DIPEA (100 μL) were added and the mixture was stirred at 70° C. for further 4 hours. Next, the mixture was allowed to cool to r.t., taken up with AcOEt (30 mL), washed with a 1N hydrochloric acid cold solution (3×15 mL) and brine (2×10 mL). The organic layer was dried and concentrated in vacuo to a residue, which was purified by flash chromatography (CH/AcOEt 8:2) to give:

1. intermediate 4a (230 mg) as a white foam,
2. intermediate 4b (231 mg) as a white foam.

Intermediate 4a

NMR ($d_6$-DMSO): δ (ppm) 7.98 (bs, 1H); 7.77 (bs, 2H); 7.24 (dd, 1H); 6.97 (dd, 1H); 6.89 (m, 1H); 5.24 (t, 1H); 5.14 (q, 1H); 3.61 (m, 1H); 3.55 (m, 1H); 2.71 (m, 2H); 2.56 (s, 3H); 2.50 (m, 2H); 2.26 (s, 3H); 1.57 (d, 3H).

MS (ES/+): m/z=505 [MH]$^+$.

Intermediate 4b

NMR ($d_6$-DMSO): δ (ppm) 7.96 (bs, 1H); 7.75 (bs, 2H); 7.24 (dd, 1H); 6.98 (dd, 1H); 6.93 (dt, 1H); 5.29 (q, 1H); 5.24 (t, 1H); 3.56 (m, 1H); 3.48 (m, 1H); 2.70 (s, 3H); 2.50 (m, 4H); 2.26 (s, 3H); 1.54 (d, 3H).

MS (ES/+): m/z=505 [MH]$^+$.

Intermediate 4a

Method B

A saturated sodium hydrogen carbonate solution (324 mL) was added to a solution of intermediate 9 (21.6 g) in AcOEt (324 mL) and the resulting mixture was vigorously stirred for 15 minutes. The aqueous layer was back-extracted with further AcOEt (216 mL) and the combined organic extracts were dried and concentrated in vacuo to give intermediate 8 as a yellow oil, which was treated with TEA (19 mL) and AcOEt (114 mL). The solution obtained was added drop-wise over 40 minutes to a solution of triphosgene (8 g) in AcOEt (64 mL) previously cooled to 0° C. under a nitrogen atmosphere, maintaining the temperature between 0° C. and 8° C.

After stirring for 1 hours at 0° C. and for 3 hours at 20° C., [1-(R)-(3,5-bis-trifluoromethyl-phenyl)-ethyl]-methylamine hydrochloride (29.7 g), AcOEt (190 mL) and TEA (38 mL) were added to the reaction mixture which was then heated to reflux for 16 hours. The solution was washed with 10% sodium hydroxide solution (180 mL), 1% hydrochloric acid solution (4×150 mL), water (3×180 mL) and brine (180 mL). The organic layer was dried and concentrated in vacuo to a residue, which was purified through a silica pad (CH/AcOEt 9:1) to give the title compound (21.5 g) as a brown thick oil.

NMR ($d_6$-DMSO): δ (ppm) 7.97-7.77 (bs+bs, 3H); 7.24 (dd, 1H); 6.97 (dd, 1H); 6.88 (td, 1H); 5.24 (m, 1H); 5.14 (q, 1H); 3.58 (m, 2H); 2.7 (m, 1H); 2.56 (s, 3H); 2.49 (m, 2H); 2.26 (s, 3H); 1.57 (d, 3H).

Intermediate 5

2-(S)-(4-Fluoro-2-methyl-phenyl)-4-oxo-piperidine-1-carboxylic acid [1-(S)-(3,5-bis-trifluoromethyl-phenyl)-ethyl]-methylamide (5a) and 2-(R)-(4-Fluoro-2-methyl-phenyl)-4-oxo-piperidine-1-carboxylic acid [1-(S)-(3,5-bis-trifluoromethyl-phenyl)-ethyl]-methylamide (5b)

A solution of triphosgene (147 mg) dissolved in dry DCM (5 mL) was added to a solution of intermediate 2 (250 mg) and DIPEA (860 µL) in dry DCM (15 mL) previously cooled to 0° C. under a nitrogen atmosphere. After 2 hours, a solution of [1-(S)-(3,5-bis-trifluoromethyl-phenyl)-ethyl]-methylamine hydrochloride (510 mg) and DIPEA (320 µL) in dry acetonitrile (20 mL) was added and the mixture was heated to 70° C. for 16 hours. Then, further [1-(S)-(3,5-bis-trifluoromethyl-phenyl)-ethyl]-methylamine hydrochloride (170 mg) and DIPEA (105 µL) were added. After further 4 hours at 70° C., the mixture was allowed to cool to r.t., taken up with AcOEt (30 mL), washed with a 1N hydrochloric acid cold solution (3×15 mL) and brine (2×10 mL). The organic layer was dried and concentrated in vacuo to a residue, which was purified by flash chromatography (CH/AcOEt 8:2) to give:
1. intermediate 5a (234 mg) as a white foam,
2. intermediate 5b (244 mg) as a white foam.

Intermediate 5a

NMR ($d_6$-DMSO): δ (ppm) 7.98 (bs, 1H); 7.77 (bs, 2H); 7.24 (dd, 1H); 6.97 (dd, 1H); 6.89 (m, 1H); 5.24 (t, 1H); 5.14 (q, 1H); 3.61 (m, 1H); 3.55 (m, 1H); 2.71 (m, 2H); 2.56 (s, 3H); 2.50 (m, 2H); 2.26 (s, 3H); 1.57 (d, 3H).
MS (ES/+): m/z=505 [MH]$^+$.

Intermediate 5b

NMR ($d_6$-DMSO): δ (ppm) 7.96 (bs, 1H); 7.75 (bs, 2H); 7.24 (dd, 1H); 6.98 (dd, 1H); 6.93 (dt, 1H); 5.29 (q, 1H); 5.24 (t, 1H); 3.56 (m, 1H); 3.48 (m, 1H); 2.70 (s, 3H); 2.50 (m, 4H); 2.26 (s, 3H); 1.54 (d, 3H).
MS (ES/+): m/z=505 [MH]$^+$.

Intermediates 6

2-(S)-(4-Fluoro-2-methyl-phenyl)-4-oxo-3,4-dihydro-2H-pyridine-1-carboxylic acid (1R, 2S, 5R)-2-isopropyl-5-methyl-cyclohexyl ester (6a) and 2-(R)-(4-Fluoro-2-methyl-phenyl)-oxo-3,4-dihydro-2H-pyridine-1-carboxylic acid (1R, 2S, 5R)-2-isopropyl-5-methyl-cyclohexyl ester (6b)

A solution of 2-bromo-5-fluoro-toluene (3.68 g) in dry THF (10 mL) was dropped over 30 minutes, into a mixture of magnesium (525 mg) and iodine (1 crystal) in dry THF (5 mL) previously heated to 70° C. under a nitrogen atmosphere. The mixture was stirred at 70° C. for 1.5 hours, then allowed to cool to r.t.

A solution of (−)-mentyl chloroformate (3.53 mL) in dry THF (15 mL) was added to a solution of 4-methoxypyridine (1.52 mL) in dry THF (35 mL) previously cooled to −78° C. under a nitrogen atmosphere. After 15 minutes, the solution containing the 4-fluoro-2-methyl-phenyl magnesium bromide was added drop-wise, and the mixture was stirred at −78° C. for 1 hour. The reaction was quenched by the addition of 1M hydrochloric acid solution (20 mL), warmed to r.t. and stirred at 23° C. for 30 minutes. After extraction with AcOEt (2×150 mL), the combined organic extracts were washed with brine (50 mL), dried and concentrated in vacuo to a residue, which was purified by flash chromatography (CH/THF/toluene 8:1:1) to give:
1. intermediate 6a (3.44 g—yellow oil)
2. intermediate 6b (530 mg—white solid).

Intermediate 6a

T.l.c.: cyclohexane/THF/toluene 7:2:1, Rf=0.59.
IR (nujol): 1718 and 1675 (C=O) cm$^{-1}$.
NMR ($d_6$-DMSO): δ (ppm) 8.14 (d, 1H); 7.08 (dd, 1H); 7.02 (dd, 1H); 6.95 (m, 1H); 5.68 (d, 1H); 5.34 (d, 1H); 4.47 (m, 1H); 3.26 (dd, 1H); 2.30 (m, 4H); 1.7 (m, 4H); 1.33 (m, 2H); 0.8 (m, 11H).
MS (ES/+): m/z=388 [MH]$^+$.

Intermediate 6b

M.p.: 117-120° C.
T.l.c.: cyclohexane/THF/toluene 7:2:1, Rf=0.56.
IR (nujol): 1718 and 1669 (C=O) cm$^{-1}$.
NMR ($d_6$-DMSO): δ (ppm) 8.17 (d, 1H); 7.04-6.94 (m, 3H); 5.70 (d, 1H); 5.35 (d, 1H); 4.42 (m, 1H); 3.26 (dd, 1H); 2.30 (m, 4H); 1.58-1.40 (m, 3H); 1.2-0.7 (m, 8H); 0.51-0.34 (bs, 6H):
MS (ES/+): m/z=388 [MH]$^+$.

Intermediate 7

2-(R)-(4-Fluoro-2-methyl-phenyl)-2,3-dihydro-1H-pyridin-4-one

Sodium methoxide (100 mg) was added to a solution of intermediate 6b (170 mg) in MeOH (15 mL) under a nitrogen atmosphere. The mixture was refluxed for two hours, and the solvent was removed in vacuo. The residue was partitioned between water (10 mL) and AcOEt (15 mL). The layers were separated, and the aqueous phase was extracted with further AcOEt (4×10 mL). The combined organic extracts were washed with brine (10 mL), dried and concentrated in vacuo to give the title compound (145 mg) as a light yellow oil.
NMR ($d_6$-DMSO): δ (ppm) 7.71 (bd, 1H); 7.45 (dd, 1H); 7.38 (t, 1H); 7.03 (m, 2H; 4.86 (dd, 1H); 4.77 (d, 1H); 2.42 (dd, 1H); 2.31 (m, 4H)
MS (ES/+): m/z=206 [M+H]$^+$.

Intermediate 8

2-(R)-(4-Fluoro-2-methyl-phenyl)-piperidin-4-one

Palladium over charcoal (10%-74 mg) was added to a solution of intermediate 7 (145 mg) in MeOH (8 mL) and THF (2 mL). The mixture was allowed to react with hydrogen in a pressure reactor (2 atm) overnight. After flushing with nitrogen, the solution was filtered and the solvent removed in vacuo. The crude product was purified by flash chromatography (AcOEt/MeOH 9:1) to give the title compound (26 mg) as a yellow oil.

The enantiomeric excess (90-95%) was detected by chiral HPLC.

T.l.c.:AcOEt/MeOH 9:1, Rf=0.2.

NMR (d$_6$-DMSO): δ (ppm) 7.49 (dd, 1H); 7.00 (m, 2H); 3.97 (dd, 1H); 3.27 (m, 1H); 2.82 (dt, 1H); 2.72 (bm, 1H); 2.47 (m, 1H); 2.40 (m, 1H); 2.29 (s, 3H); 2.25 (dt, 1H); 2.18 (m, 1H).

MS (ES/+): m/z=208 [MH]$^+$.

Intermediate 9

2-(R)-(4-Fluoro-2-methyl-phenyl)-piperidin-4-one L-(+)-mandelate

A solution of L-(+)-mandelic acid (22.6 g) in AcOEt (308 mL) was added to a solution of intermediate 2 (31 g) in AcOEt (308 mL). Then isopropanol (616 mL) was added and the solution was concentrated in vacuo to 274 mL. The solution was then cooled to 0° C. and further cold isopropanol (96 mL) was added. The thick precipitate was stirred under nitrogen for 5 hours at 0° C., then filtered and washed with cold Et2O (250 mL) to give the title compound as a pale yellow solid (20.3 g).

M.p.: 82-85° C.

NMR (d$_6$-DMSO): δ (ppm) 7.51 (dd, 1H); 7.40 (m, 2H); 7.32 (m, 2H); 7.26 (m, 1H); 1H); 7.0 (m, 2H); 4.95 (s, 1H); 4.04 (dd, 1H); 3.31 (m, 1H); 2.88 (m, 1H); 2.49-2.2 (m, 4H); 2.29 (s, 3H).

Chiral HPLC: HP 1100 HPLC system; column Chiralcel OD-H, 25 cm×4.6 mm; mobile phase: n-hexane/isopropanol 95:5+1% diethylamine; flow=1.3 ml/min; λ=240/215 nm; retention time: 12.07 minutes.

Intermediate 10

2-(R)-4-Fluoro-2-methyl-phenyl)-4-oxo-piperidine-1carboxylic acid (3,5-bis-trifluoromethyl-benzyl)-methylamide Method A A solution of triphosgene (17 mg) in dry DCM (2 mL) was added to a solution of intermediate 8 (26 mg) and DIPEA (65 mg) in dry DCM (3 mL) previously cooled to 0° C. under a nitrogen atmosphere. After two hours acetonitrile (10 mL) was added, the temperature was allowed to reach r.t. and the DCM evaporated under a nitrogen flush. Then, a solution of 3,5-(bis-trifluoromethyl-benzyl)-methylamine hydrochloride (74 mg) and DIPEA (130 mg) in acetonitrile (3 mL) was added and the mixture was stirred at 23° C. overnight. The solvent was concentrated in vacuo. The residue was dissolved in AcOEt (10 mL) and washed with 1N hydrochloric acid solution (3×5 mL), 5% sodium hydrogen carbonate (5 mL) and brine (10 mL). The organic layer was dried and concentrated in vacuo to a residue, which was purified by flash chromatography (CH/AcOEt 1:1) to give the title compound (50 mg) as a white solid.

Method B

A saturated sodium hydrogen carbonate solution (348 mL) was added to a solution of intermediate 9 (23.2 g) in AcOEt (348 mL) and the resulting mixture was vigorously stirred for 15 minutes. The aqueous layer was back-extracted with further AcOEt (230 mL) and the combined organic extracts were dried and concentrated in vacuo to give intermediate 8 (12.31 g) as a yellow oil, which was treated with TEA (20.5 mL) and AcOEt (123 mL). The solution obtained was added drop-wise over 40 minutes to a solution of triphosgene (8 g) in AcOEt (61 mL) previously cooled to 0° C. under a nitrogen atmosphere, maintaining the temperature between 0° C. and 8° C.

After stirring for 2 hours at 20° C., 3,5-(bis-trifluoromethyl-benzyl)-methylamine hydrochloride (28.1 g), AcOEt (184 mL) and TEA (33 mL) were added to the reaction mixture which was then further stirred for 2 hours at 20° C.

The solution was washed with 10% sodium hydroxide solution (3×185 mL) and 1% hydrochloric acid solution (3×185 mL). The organic layer was dried and concentrated in vacuo to a crude (38 g), which was purified through a silica pad (CH/AcOEt from 9:1 to 1:1) to give the title compound (24.7 g) as a colourless oil.

NMR (d$_6$-DMSO): δ (ppm) 7.96 (s, 1H); 7.76 (s, 2H); 7.26 (dd, 1H); 6.98 (dd, 1H); 6.90 (td, 1H); 5.23 (t, 1H); 4.61 (d, 1H); 4.41 (d, 1H); 3.60 (m, 2H); 2.69 (m,2H); 2.79 (s, 3H); 2.50 (m, 2H); 2.27 (s,3H).

MS (ES/+): m/z=491 [MH]$^+$.

Intermediate 11

2-(4-Fluoro-2-methyl-phenyl)-4-hydroxy-piperidine-1-carboxylic acid (3,5-bis-trifluoromethyl-benzyl)-methylamide A solution of intermediate 3 (150 mg) and sodium borohydride (13 mg) in dry MeOH (5 mL) was stirred at 0° C. for 2 hours under a nitrogen atmosphere. The crude solution was washed with a saturated ammonium chloride solution (4 mL) and taken up with AcOEt (5 mL). The aqueous phase was extracted with AcOEt (3×5 mL) and the combined organic phases were washed with brine (5 mL). The organic layer was dried and concentrated in vacuo to a residue which was purified by flash chromatography (AcOEt/CH 7:3) to give:

1. intermediate 11a (4 mg)
2. intermediate 11b (30 mg).

Intermediate 11a (diastereoisomer A)

NMR (d$_6$-DMSO): δ (ppm) 7.94 (bs, 1H); 7.63 (bs, 2H); 7.22 (bs, 1H); 6.88 (dd, 1H); 6.77 (dt, 1H); 4.69 (d, 1H); 4.60 (d, 1H); 4.36 (d, 1H); 4.13 (dd, 1H); 3.94 (m, 1H); 3.57 (m, 1H); 2.88 (s, 3H); 2.65 (m, 1H); 2.48 (s, 3H); 1.83 (m, 1H); 1.62 (m, 2H); 1.22 (m, 1H).

MS (ES/+): m/z=493 [MH]$^+$, 475 [M-OH]$^+$.

Intermediate 11b (diastereoisomer B)

NMR (d$_6$-DMSO): δ (ppm) 7.93 (bs, 1H); 7.58 (bs, 2H); 7.21 (dd, 1H); 6.88 (dd, 1H); 6.77 (dt, 1H); 4.78 (d, 1H); 4.62 (d, 1H); 4.33 (d, 1H); 4.13 (dd, 1H); 3.58 (m, 1H); 3.37 (m, 1H); 2.90 (s, 3H); 2.67 (m, 1H); 2.32 (s, 3H); 1.89 (m, 1H); 1.83 (m, 1H); 1.52 (dq, 1H); 1.29 (q, 1H).

MS (ES/+): m/z=493 [MH]$^+$, 475 [M-OH]$^+$.

Intermediate 12

(4-Fluoro-2-methyl-phenylamino)-acetic acid ethyl ester

A solution of ethyl glyoxalate (50% solution in toluene—40.8 mL) in toluene (180 mL) was heated to reflux for 1.5 hours under a Nitrogen atmosphere, in a flask equipped with a Dean Stark apparatus. Then, a solution of 4-fluoro-2-methyl-aniline (10 g) in dry toluene (20 mL) was slowly added. The mixture was heated to reflux for 3 hours, then it was concentrated in vacuo. The residue was purified by flash chromatography (toluene/CH/AcOEt 4:4:2) to give the title compound (13.06 g) as a yellow oil.

T.l.c.: toluene/CH/AcOEt 4:4:2, Rf=0.67.

NMR (CDCl3): δ (ppm) 7.8 (s, 1H); 6.95 (d, 1H); 6.85 (d, 2H); 4.4 (q, 2H); 2.35 (s, 3H); 3.3 (t 3H).

MS (ES/+): m/z=210 [M+H]$^+$.

Intermediate 13

1-(4-(Fluoro-2-methyl-phenyl)-4-oxo-1,2,3,4-tetrahydro-pyridine-2-carboxylic acid ethyl ester Boron trifluoride etherate (1.22 mL) was added to a solution of intermediate 12 (2 g) in anhydrous DCM (20 mL) previously cooled to −78° C. under a Nitrogen atmosphere. After stirring for 15 minutes at −78° C., the 1-methoxy-3-trimethylsiloxy-1,3-butadiene (2.67 mL) was dropped over 45 minutes. The resulting solution was stirred at −78° C. for 2 hours, then TFA (0.74 mL) was added. The mixture was stirred at 0° C. for 15 minutes, then a saturated sodium hydrogen carbonate solution was added and the mixture was extracted with AcOEt (3×50 mL). The combined organic extracts were dried and concentrated in vacuo to give a residue, which was purified by flash chromatography (CH/AcOEt from 8:3 to 7:3) to give the title compound (1.5 g) as a pale yellow solid.

T.l.c.: CH/AcOEt 6:4, Rf=0.2.

NMR (CDCl3): δ (ppm) 7.4 (dd, 1H); 7.1 (d, 1H); 7.0-6.8 (m, 2H); 5.15 (d, 1H); 4.4 (m, 1H); 4.1 (m, 2H); 3.1-2.85 (m, 2H); 2.4 (s, 3H); 1.15 (t, 3H).

Intermediate 14

1-(4-Fluoro-2-methyl-phenyl)-4-oxo-piperidine-2-carboxylic acid ethyl ester

L-selectride (1M solution in dry THF, 3.96 mL) was added drop-wise, over 1 hour, to a solution of intermediate 13 (1 g) in dry THF (30 mL) previously cooled to −78° C. under a Nitrogen atmosphere. After 1 hour, a saturated sodium hydrogen carbonate solution (20 mL) was added drop-wise and the solution was extracted with AcOEt (3×50 mL). The combined organic extracts were dried and concentrated in vacuo to a residue, which was purified by flash chromatography (CH/AcOEt 8:2) to give the title compound (810 mg) as a white solid.

T.l.c.: CH/AcOEt 6:4, Rf=0.6.

NMR (CDCl3): δ (ppm) 7.4 (dd, 1H); 7.1 (dd, 1H); 6.9 (dd, 1H); 6.8 (dt, 1H); 4.2 (q, 2H); 4.15 (m, 1H); 3.6 (m, 1H); 3.2 (m, 1H); 2.8-2.7 (dd, 2H); 2.6 (m, 2H); 2.4 (s, 3H); 1.2 (t, 3H).

Intermediate 15

1-(4-Fluoro-2-methyl-phenyl)-4-oxo-piperidine-2carboxylic acid

Lithium hydroxide monohydrate (241 mg) was added to a solution of intermediate 14 (300 mg) in MeOH (15 mL) and water (3 mL) and the resulting solution was stirred at 80° C. for 1 hour. The solution was allowed to cool to r.t. and extracted with Et2O. The aqueous layer was acidified until pH=6 with acetic acid and extracted with AcOEt (3×15 mL). The combined organic extracts were dried and concentrated in vacuo to give the title compound (230 mg) as yellow solid, which was used without any further purification in the next step.

MS (ES/+): m/z=252 [M+H]$^+$.

Intermediate 16

1-(4-Fluoro-2-methyl-phenyl)-4-oxo-piperidine-2-carboxylic acid (3,5-dichloro-benzyl)-methylamide DIPEA (0.47 mL) and O-(benzotriazol-1-yl)-N,N,N'N'-tetramethyluronium tetrafluoroborate (385.3 mg) were added to a solution of intermediate 16 (230 mg) in anhydrous DMF (20 mL) under a Nitrogen atmosphere. After stirring for 15 minutes, (3,5-dichlorobenzyl)-methylamine hydrochloride (225 mg) was added and the mixture was stirred at r.t. for 4 hours. The solution was diluted with water (30 mL) and extracted with AcOEt (3×60 mL). The combined organic extracts were washed with cold water (50 mL) and brine (3×80 mL), then concentrated in vacuo. The residue was purified by flash chromatography (CH/AcOEt 1:1) to give the title compound (176 mg) as a pale yellow solid.

T.l.c.: CH/AcOEt 3:7, Rf=0.52.

NMR (d$_6$-DMSO): δ (ppm) 7.5-7.45 (2t, 1H); 7.14-6.88 (2d, 2H); 7.05 (dd, 1H); 6.92 (dd, 1H); 6.82 (dt, 1H); 4.66-4.51 (2m, 1H); 4.59 (d, 1H); 4.15-4.1 (d+m, 1H); 3.83-3.57 (2m, 1H); 3.05 (m, 1H); 2.73 (m, 1H); 2.51 (m, 1H); 2.4-2.25 (m, 2H); 2.66-2.37 (2s, 3H); 2.37-2.24 (2s, 3H).

MS (ES/+): m/z=423 [M+H]$^+$.

Intermediate 17

1-(4-Fluoro-2-methyl-phenyl)-4-oxo-piperidine-2-carboxylic acid [1-(R)-3,5-bis-trifluoromethyl-phenyl)-ethyl]-methylamide (17a—diastereoisomer 1) and 1-(4-Fluoro-2-methyl-phenyl)-4-oxo-piperidine-2-carboxylic acid [1-(R)-3,5-bis-trifluoromethyl-phenyl)-ethyl]-methylamide (17b—diastereoisomer 2)

DIPEA (0.531 mL) and O-(benzotriazol-1-yl)-N,N,N'N'-tetramethyluronium tetrafluoroborate (423 mg) were added to a solution of intermediate 15 (298 mg) in anhydrous DMF (15 mL) under a Nitrogen atmosphere and the resulting solution was stirred at r.t for 15 minutes.

At the same time, [1-(R)-3,5-bis-trifluoromethyl-phenyl)-ethyl]-methylamine maleate (500 mg) was treated with a saturated sodium hydrogen carbonate solution (10 ML) and extraction with AcOEt (2×30 mL); the organic layer was dried and concentrated in vacuo to give [1-(R)-3,5-bis-trifluoromethyl-phenyl)-ethyl]-methylamine (303 mg). This intermediate was added to the previous solution and the mixture was stirred at 23° C. for 36 hours.

The solution was diluted with water (30 mL) and extracted with AcOEt (3×60 mL). The combined organic extracts were washed with cold water (2×50 mL) and brine (2×50 mL), dried and concentrated in vacuo. The residue was purified by flash chromatography (CH/AcOEt 1:1) to give:

1. intermediate 17a (56 mg) as yellow oil.
2. intermediate 17b (36 mg) as yellow oil.

Intermediate 17a

T.l.c.: CH/AcOEt 1:1, Rf=0.6.

NMR (d$_6$-DMSO): δ (ppm) 7.95 (s, 1H); 7.72 (s, 2H); 7.02 (m, 2H); 6.94 (m, 1H); 5.71 (q, 1H); 4.62 (m, 1H); 3.55 (m, 1H); 3.01 (m, 1H); 2.67 (m, 1H); 2.34-2.17 (m, 4H); 2.04 (s, 3H); 1.33 (d, 3H).

Intermediate 17b

T.l.c.: CH/AcOEt 1:1, Rf=0.4.
NMR (d$_6$-DMSO): δ (ppm) 8.02 (bs, 1H); 7.76 (bs, 2H); 6.95 (dd, 1H); 6.69 (dt, 1H); 6.46 (dt, 1H); 5.76 (q, 1H); 4.56 (m, 1H); 3.52 (m, 1H); 3.0 (m, 1H); 2.68 (m, 1H); 2.44 (m, 1H); 2.26 (m, 5H); 2.15 (s, 3H); 1.4 (d, 3H).

Intermediate 18

1-(4-Fluoro-2-methyl-phenyl)-4-oxo-piperidine-2-carboxylic acid (3,5-bis-trifluoromethyl-benzyl)-methylamide DIPEA (2.6 mL) and O-(benzotriazol-1-yl)-N,N,N'N'-tetramethyluronium hexafluorophosphate (2.48 g) were added to a solution of intermediate 15 (1.259 g) in anhydrous DMF (25 mL) under a Nitrogen atmosphere. After stirring 30 minutes, (3,5-bis-trifluoromethyl-benzyl)-methylamine hydrochloride (1.62 g) was added and the mixture was stirred at r.t. for 16 hours. The reaction mixture was diluted with AcOEt (50 mL) and washed with a saturated ammonium chloride solution (30 mL), a saturated sodium hydrogen carbonate solution (30 mL) and brine (3×50 mL). The organic extracts were dried and concentrated in vacuo. The residue was purified by flash chromatography (CH/AcOEt 9:1) to give the title compound (1.59 g) as a dark yellow oil.

T.l.c.: CH/AcOEt 1:1, Rf=0.25.
NMR (d$_6$-DMSO): δ (ppm) 8.03 (bs, 1H); 7.84 (bs, 2H); 7.03 (dd, 1H); 6.79 (dd, 1H); 6.64 (td, 1H); 4.80 (d, 1H); 4.67 (m, 1H); 4.29 (d, 1H); 3.55 (m, 1H); 3.04 (m, 1H); 2.74 (m, 1H); 2.5 (m, 1H); 2.4-2.2 (m, 2H); 2.40 (s, 3H); 2.38 (s, 3H).
MS (ES/+): m/z=491 [M+H]$^+$.

EXAMPLE 1

4-(R,S)-(2,2,2-Trifluoroethyl)-amino-2-(R)-(4-fluoro-2-methyl-phenyl)-piperidine-1-carboxylic acid [1-(R)-(3,5-bis-trifluoromethyl-phenyl)-ethyl]-methylamide hydrochloride A solution of intermediate 4a (120 mg), 2,2,2-trifluoroethylamine (190 μL) in dry 1,2-dichloroethane (10 mL) was stirred at 23° C. for 1 hours under a nitrogen atmosphere, then sodium triacetoxyborohydride (75.7 mg) was added. The mixture was stirred at 23° C. for 18 hours, then further 2,2,2-trifluoroethylamine (190 μL) and few drops of acetic acid were added and the solution was stirred for further 24 hours. The solution was washed with a 5% sodium hydrogen carbonate solution (10 mL) and brine (10 mL). The organic layer was dried and concentrated in vacuo to a residue that was purified by flash chromatography (CH/AcOEt 6:4) to give the 4-(2,2,2-trifluoroethyl)amino-2-(R)-(4-fluoro-2-methyl-phenyl)-piperidine-1-carboxylic acid [1-(R)-(3,5-bis-trifluoromethyl-phenyl)-ethyl]-methylamide (27 mg—T.l.c.: CH/AcOEt 1:1 Rf=0.77) as an enantiomeric mixture in ratio C-2 and C-4 anti/syn 4:6.

This material (25 mg) was dissolved in dry Et2O (5 mL) and treated with hydrochloric acid (1M in Et2O—1 mL). The resulting mixture was stirred at 23° C. for 30 minutes, then concentrated in vacuo to give the title compound as a whitish solid (25 mg).

M.p.: 116-7° C.
IR (nujol): 1659 and 1651 (C=O) cm$^{-1}$.
NMR (d$_6$-DMSO): δ (ppm) 7.91 (s, 1H); 7.73 (s, 1H); 7.68 (s, 1H); 7.23 and 7.17 (2dd, 1H); 6.74-6.76 (m, 2H); 5.3 and 5.18 (2q, 1H); 4.9 and 4.18 (m and dd, 1H); 3.5-3.1 (m, 3H); 2.74 and 2.65 (2s, 3H); 2.35 and 2.28 (2s, 3H); 2.1-1.5 (m, 4H); 1.5 and 1.46 (2d, 3H).
MS (ES/+): m/z=588 [MH—HCl]$^+$.

EXAMPLE 2

4-(R)-(2,2-Dimethyl-propylamino)-2-(R)-(4-fluoro-2-methyl-phenyl)-piperidine-1-carboxylic acid, [1-(R)-(3,5-bis-trifluoromethyl-phenyl)-ethyl]-methylamide hydrochloride (2a)

4-(S)-(2,2-Dimethyl-propylamino)-2-(R)-(4-fluoro-2-methyl-phenyl)-piperidine-1-carboxylic acid, [1-(R)-(3,5-bis-trifluoromethyl-phenyl)-ethyl]-methylamide hydrochloride (2b)

A solution of intermediate 4a (120 mg), 2,2-dimethyl-propylamine (20.9 mg) and sodium triacetoxyborohydride (78.2 mg) in dry 1,2-dichloroethane (5 mL) was stirred at 23° C. for 2 hours under a nitrogen atmosphere. The solution was washed with a 5% sodium hydrogen carbonate solution (10 mL) and brine (10 mL). The organic layer was dried and concentrated in vacuo to a residue that was purified by flash chromatography (AcOEt/MeOH 85:15) to give three fractions:
1. diastereoisomer 1 (65.4 mg—T.l.c.: AcOEt/MeOH 7:3 Rf=0.41),
2. a mixture of the two diastereoisomers (15.0 mg)
3. diastereoisomer 2 (22.0 mg—T.l.c.: AcOEt/MeOH 7:3 Rf=0.39).

EXAMPLE 2a

A solution of diastereoisomer 1 (64.0 mg) in Et2O (5 mL) was treated with hydrochloric acid (1M in Et2O—1 mL). The resulting solution was stirred at 23° C. for 30 minutes, then it was concentrated in vacuo to give the title compound as a white solid (67.4 mg).

IR (nujol): 3376 (NH$_2^+$), 1627 (C=O) cm$^{-1}$.
NMR (d$_6$-DMSO): δ (ppm) 8.16,8.10 (2bm, 2H); 7.99 (s, 1H); 7.78 (s, 2H); 7.39 (dd, 1H); 7.00 (dd, 1H); 6.93 (dt, 1H); 5.24 (t, 1H); 5.09 (q, 1H); 3.54 (m, 2H); 3.05 (t, 1H); 2.81 (m, 2H); 2.60 (s, 3H); 2.31 (m, 1H); 2.20 (s, 3H); 2.13 (m, 2H); 1.57 (d, 3H); 1.62 (m, 1H); 0.98 (s, 9H).
MS (ES/+): m/z=576 [MH—HCl]$^+$.

EXAMPLE 2b

A solution of diastereoisomer 2 (21.0 mg) in dry Et2O (5 mL) was treated with hydrochloric acid (1M in Et2O—1 mL). The resulting mixture was stirred at 23° C. for 15 minutes, then filtered and further treated with dry Et2O to give the title compound as a whitish solid (11 mg).

NMR (d$_6$-DMSO): δ (ppm) 7.99 (bs, 3H); 7.67 (bs, 1H); 7.16 (m, 1H); 6.96 (m, 1H); 6.95 (m, 1H); 5.29 (m, 1H); 4.20 (m, 1H); 3.5-2.7 (m, 5H); 2.62 (s, 3H); 2.35 (s, 3H); 2.7-2.0 (m, 4H); 1.45 (d, 3H); 0.95 (s, 9H).
MS (ES/+): m/z=576 [MH—HCl]$^+$.

EXAMPLE 3

4-(R)-Ethylamino-2-(R)-(4-fluoro-2-methyl-phenyl)-piperidine-1-carboxylic acid [1-(R)-(3,5-bis-trifluoromethyl-phenyl)-ethyl]-methylamide hydrochloride (3a) and 4-(S)-Ethylamino-2-(R)-(4-fluoro-2-methyl-phenyl)-piperidine-1-carboxylic acid [1-(R)-(3,5-bis-trifluoromethyl-phenyl)-ethyl]-methylamide hydrochloride (3b)

A suspension of intermediate 4a (100 mg), ethylamine hydrochloride (326 mg), TEA (613 μL) and sodium triacetoxyborohydride (63 mg) in dry 1,2-dichloroethane (2.5 mL) was stirred at 23° C. for 6 hours under a nitrogen atmosphere. The solution was diluted with DCM (10 ml) washed with 5% sodium hydrogen carbonate solution (10 mL) and brine (10 mL). The organic layer was dried and concentrated in vacuo to a residue which was purified by flash chromatography (AcOEt/MeOH 9:1) to give two fractions:
1. diastereoisomer 1 (50 mg—T.l.c. AcOEt/MeOH 8:2 Rf=0.2)
2. diastereoisomer 2 (10 mg—T.l.c. AcOEt/MeOH 8:2 Rf=0.13)

EXAMPLE 3a

A solution of diastereoisomer 1 (50 mg) in dry Et2O (5 mL) was treated with hydrochloric acid (1M in Et2O—2 mL) and the resulting solution was stirred at 23° C. for 30 minutes, then it was concentrated in vacuo. The residue was triturated with Et2O to give the title compound as a white solid (24 mg).
NMR (d$_6$-DMSO): δ (ppm) 8.56 (bs, 2H); 7.99 (s, 1H); 7.75 (s, 2H); 7.32 (dd, 1H); 6.98 (dd, 1H); 6.90 (m, 1H); 5.12 (q, 1H); 5.04 (t, 1H); 3.6-3.4 (m, 2H); 3.13 (t, 1H); 2.97 (m, 2H); 2.61 (s, 3H); 2.25 (s, 3H); 2.10 (m, 2H); 1.98 (m, 1H); 1.65 (m, 1H); 1.55 (d, 3H); 1.19 (t, 3H).
MS (ES/+): m/z=534 [MH—HCl]$^+$.

EXAMPLE 3b

A solution of diastereoisomer 2 (10 mg) in dry Et2O (2 mL) was treated with hydrochloric acid (1M in Et2O—0.5 mL). The resulting mixture was stirred at 23° C. for 30 minutes, then it was concentrated in vacuo. The residue was triturated with Et2O to give the title compound as a white solid (7 mg).
NMR (d$_6$-DMSO): δ (ppm) 8.60 (bs, 2H); 7.99 (s, 1H); 7.67 (s, 2H); 7.15 (dd, 1H); 6.94 (dd, 1H); 6.83 (dt, 1H); 5.29 (q, 1H); 4.19 (dd, 1H); 3.43 (bd, 1H); 3.30 (m, 1H); 2.97 (bm, 2H); 2.80 (t, 1H); 2.74 (s, 3H); 2.35 (s, 3H); 2.11 (bd, 1H); 2.06 (bd, 1H); 1.68 (m, 1H); 1.57 (m, 1H); 1.45 (d, 3H); 1.17 (t, 3H).
MS (ES/+): m/z=534 [MH—HCl]$^+$.

EXAMPLE 4

4-(R)-Dimethylamino-2-(R)-(4-fluoro-2-methyl-phenyl)-piperidine-1-carboxylic acid [1-(R)-(3,5-bis-trifluoromethyl-phenyl)-ethyl]-methylamide hydrochloride (4a) and 4-(S)-Dimethylamino-2-(R)-(4-fluoro-2-methyl-phenyl)-piperidine-1-carboxylic acid [1-(R)-(3,5-bis-trifluoromethyl-phenyl)-ethyl]-methylamide hydrochloride (4b)

A solution of intermediate 4a (93 mg), dimethylamine (2 M in THF—40 μL) and sodium triacetoxyborohydride (57 mg) in dry 1,2-dichloroethane (10 mL) was stirred at 23° C. for 6 hours under a nitrogen atmosphere. The solution was washed with a 5% sodium hydrogen carbonate solution (10 mL) and brine (10 mL). The organic layer was dried and concentrated in vacuo to a residue which was purified by flash chromatography (AcOEt/MeOH 95:5 to 80:20) to give two fractions:
1. diastereoisomer 1 (39 mg—T.l.c.: AcOEt/MeOH 8:2 Rf=0.2),
2. diastereoisomer 2 (26 mg—T.l.c.: AcOEt/MeOH 8:2 Rf=0.15).

EXAMPLE 4a

A solution of diastereoisomer 1 (39 mg) in dry Et2O (5 mL) was treated with hydrochloric acid (1M in Et2O—2 mL) and the resulting solution was stirred at 23° C. for 5 minutes. The solution was concentrated in vacuo to give a white solid that was triturated in Et2O (2 mL), then filtered to give the title compound as a white solid (16 mg).
IR (nujol): 3443 (NH$_2^+$), 1640 (C=O) cm$^{-1}$.
NMR (d$_6$-DMSO): δ (ppm) 9.64 (bs, 1H); 7.99 (s, 1H); 7.76 (s, 2H); 7.35 (dd, 1H); 7.00 (dd, 1H); 6.92 (bt, 1H); 5.19 (bt, 1H); 5.07 (q, 1H); 3.58 (m, 1H); 3.17 (t, 1H); 2.77 (bs, 3H); 2.73 (bs, 3H); 2.55 (s, 3H); 2.21 (s+m, 3H+1H); 2.07 (bm, 2H); 1.63 (dq, 1H); 1.55 (d, 3H).
MS (ES/+): m/z=534 [MH—HCl]$^+$.

EXAMPLE 4b

A solution of diastereoisomer 2 (26 mg) in dry Et2O (5 mL) was treated with hydrochloric acid (1M in Et2O—2 mL) and the resulting solution was stirred at 23° C. for 5 minutes. The solution was concentrated in vacuo to give a white solid that was triturated in Et2O (2 mL), then filtered to give the title compound as a white solid (24 mg).
IR (nujol): 3399 (NH$_2^+$), 1665 (C=O) cm$^{-1}$.
NMR (d$_6$-DMSO): δ (ppm) 9.75 (bs, 1H); 7.99 (s, 1H); 7.67 (s, 2H); 7.22 (dd, 1H); 6.93 (dd, 1H); 6.81 (dt, 1H); 5.31 (q, 1H); 4.17 (dd, 1H); 3.44 (m, 2H); 2.76 (t, 1H); 2.73 (s, 3H); 2.72 (s, 3H+3H); 2.35 (s, 3H); 2.08 (d, 1H); 2.01 (d, 1H); 1.85 (dq, 1H); 1.64 (q, 1H); 1.46 (d, 3H)

EXAMPLE 5

4-(R)-Dimethylamino-2-(R)-(4-fluoro-2-methyl-phenyl)-piperidine-1-carboxylic acid (3,5-bis-trifluoromethyl-benzyl)-methylamide hydrochloride (5a) and 4-(S)-Dimethylamino-2-(R)-(4-fluoro-2-methyl-phenyl)-piperidine-1-carboxylic acid (3,5-bis-trifluoromethyl-benzyl)-methylamide hydrochloride (5b)

A solution of intermediate 10 (1.0 g) and dimethylamine (2 M in THF) (50 mL) in MeOH (40 mL) was stirred at 23° C. for 5 hours, then a solution of sodium borohydride (85 mg) in dry MeOH (10 mL) was added. The resulting mixture was stirred at 23° C. for 30 minutes, then a 5% solution of sodium hydrogen carbonate (20 mL) was added. The mixture was concentrated in vacuo to eliminate the alcohol, then the aqueous phase was extracted with AcOEt (3×50 mL). The combined organic extracts were dried and concentrated in vacuo to a residue which was purified by flash chromatography (AcOEt/MeOH 7:3) to give three fractions:
1. diastereoisomer 1 (61 mg as a white solid T.l.c.: AcOEt/MeOH 8:2, Rf=0.23)
2. mixture of the two diastereoisomers (190 mg)
3. diastereoisomer 2 (436 mg as a white solid—T.l.c.: AcOEt/MeOH 8:2, Rf=0.2).

EXAMPLE 5a

A solution of diastereoisomer 1 (61 mg) in dry Et2O (5 mL) was treated with hydrochloric acid (1M in Et2O—0.12 mL). The resulting mixture was stirred at 0° C. for 15 minutes, then filtered to give the title compound as a white solid (55 mg).
M.p.: 180-3° C.

NMR (d$_6$-DMSO): δ (ppm) 9.78 (bs, 1H); 7.97 (s, 1H); 7.79 (s, 2H); 7.35 (dd, 1H); 7.0 (dd, 1H); 6.92 (dt, 1H); 5.17 (bt, 1H); 4.56 (d, 1H); 4.41 (d, 1H); 3.56 (bm, 2H); 3.1 (t, 1H); 2.75 (m+s, 9H); 2.23 (s, 4H); 2.09 (bm, 2H); 1.66 (m, 1H).
MS (ES/+): m/z=520 [M-Cl]$^+$.

EXAMPLE 5b

A solution of diastereoisomer 2 (436 mg) in dry Et2O (25 mL) was treated with hydrochloric acid (1M in Et2O—0.85 mL). The resulting mixture was stirred at 0° C. for 15 minutes, then filtered to give the title compound (380 mg) as a white solid.

M.p.: 147-150° C.
IR (nujol): 3406 (NH$_2^+$), 1656 (C=O) cm$^{-1}$.
NMR (d$_6$-DMSO): δ (ppm) 9.87 (bs, 1H); 7.95 (s, 1H); 7.59 (s, 2H); 7.27 (dd, 1H); 6.94 (dd, 1H); 6.82 (m, 1H); 4.63 (d, 1H); 4.37 (d, 1H); 4.2 (dd, 1H); 3.54 (m, 1H); 3.3 (m, 1H); 2.92 (s, 3H); 2.70 (m, 6H); 2.70 (m, 1H); 2.36 (s, 3H); 2.1-2.00 (m, 2H); 1.85 (m, 1H); 1.6 (m, 1H).
MS (ES/+): m/z=520 [M-Cl]$^+$.
[α]$_D$=−82.77 (1.07% in DMSO).

EXAMPLE 6

4-(R)-(2-Fluoroethyl)-amino-2-(R)-(4-fluoro-2-methyl-phenyl)-piperidine-1-carboxylic acid [1-(R)-(3,5-bis)-trifluoromethyl-phenyl)-ethyl]-methylamide hydrochloride (6a) and 4-(S)-(2-Fluoroethyl)-amino-2-(R)-(4-fluoro-2-methyl-phenyl)-piperidine-1-carboxylic acid [1-(R)-(3,5-bis)trifluoromethyl-phenyl)-ethyl]-methylamide hydrochloride (6b)

A suspension of intermediate 4a (100 mg), 2-fluoroethylamine hydrochloride (98 mg), TEA (100 μL) and sodium triacetoxyborohydride (65 mg) in dry 1,2-dichloroethane (8 mL) was stirred at 23° C. for 2 hours under a nitrogen atmosphere. A further amount of 2-fluoroethylamine hydrochloride (98 mg) and TEA (100 μL) were added and the mixture stirred for 2 hours at 23° C. A further amount of sodium triacetoxyborohydride (65.0 mg) was added and the mixture stirred at 23° C. for 1.5 hours under a nitrogen atmosphere.

The solution was washed with a saturated sodium hydrogen carbonate solution (8 mL) and brine (8 mL). The organic layer was dried and concentrated in vacuo to a residue that was purified by flash chromatography (AcOEt/MeOH 95:5) to give two fractions:
1. diastereoisomer 1 (26.0 mg—T.l.c.: AcOEt/MeOH 8:2 Rf=0.44)
2. diastereoisomer 2 (17.0 mg—T.l.c.: AcOEt/MeOH 8:2 Rf=0.3).

EXAMPLE 6a

A solution of diastereoisomer 1 (26.0 mg) in dry Et2O (1 mL) was treated with hydrochloric acid (1M in Et2O—20 μL), and the resulting solution was stirred at 0° C. for 15 minutes. The solution was concentrated in vacuo and the residue was triturated with n-pentane (1 mL) to give the title compound as a white solid (21 mg).
NMR (d$_6$-DMSO): δ (ppm) 8.96 (bs, 2H); 7.99 (s, 1H); 7.75 (s, 2H); 7.34 (dd, 1H); 7.00 (dd, 1H); 6.91 (m, 1H); 5.16-5.06 (m, 2H); 4.84-4.6 (m, 2H); 3.64-3.10 (m, 5H); 2.3-1.65 (m, 4H); 2.60 (s, 3H); 2.24 (s, 3H); 1.55 (d, 3H).
MS (ES/+): m/z=552 [MH—HCl]$^+$.

EXAMPLE 6b

A solution of diastereoisomer 2 (17.0 mg) in dry Et2O (1 mL) was treated with hydrochloric acid (1M in Et2O—20 μL), and the resulting solution was stirred at 0° C. for 15 minutes. The solution was concentrated in vacuo and the residue was triturated with n-pentane (1 mL) to give the title compound as a white solid (15 mg).
NMR (d$_6$-DMSO): δ (ppm) 8.93 (s, 2H); 7.99 (s, 1H); 7.67 (s, 2H); 7.15 (dd, 1H); 6.94 (dd, 1H); 6.83 (m, 1H); 5.28 (q, 1H); 4.8-4.6 (m, 2H); 4.18 (dd, 1H); 3.4 (m, 3H); 2.8-2.7 (m, 2H); 2.2-2.0 (m, 2H); 1.8-1.5 (m, 2H); 2.73 (s, 3H); 2.34 (s, 3H); 1.45 (d, 3H).
MS (ES/+): m/z=552 [MH—HCl]$^+$.

EXAMPLE 7

4-(R)-(2-Fluoro-ethylamino)-2-(R)-(4-fluoro-2-methyl-phenyl)-piperidine-1-carboxylic acid (3,5-bis-trifluoromethyl-benzyl)-methylamide hydrochloride (7a) and 4-(S)-(2-Fluoro-ethylamino)-2-(R)-(4-fluoro-2-methyl-phenyl)-piperidine-1-carboxylic acid (3,5-bis-trifluoromethyl-benzyl)-methylamide hydrochloride (7b)

A mixture of intermediate 10 (65 mg), 2-fluoroethylamine hydrochloride (132 mg), TEA (184 μL) and sodium triacetoxyborohydride (42 mg) in dry acetonitrile (5 mL) was stirred at r.t. under a nitrogen atmosphere. After 6 hours further 2-fluoroethylamine hydrochloride (264 mg), TEA (368 μL) and sodium triacetoxyborohydride (15 mg) were added. After stirring at r.t. for 20 hours, the crude solution was quenched with a 5% sodium hydrogen carbonate solution (4 mL) and taken up with AcOEt (5 mL). The aqueous phase was extracted with AcOEt (3×5 mL) and the combined organic phases were washed with brine (5 mL). The organic layer was dried and concentrated in vacuo to a residue which was purified by flash chromatography (AcOEt/MeOH 95:5) to give two fractions:
1. diastereoisomer 1 (35 mg—T.l.c. AcOEt/MeOH 9:1 Rf=0.4)
2. diastereoisomer 2 (32 mg—T.l.c. AcOEt/MeOH 9:1 Rf=0.27).

EXAMPLE 7a

A solution of diastereoisomer 1 (30 mg) in dry Et2O (5 mL) was treated with hydrochloric acid (1M in Et2O—0.5 mL) at 0° C. and the resulting solution was stirred under a nitrogen atmosphere for 30 minutes. The solution was concentrated in vacuo and the residue was triturated with Et2O to give the title compound as a whitish solid (26 mg).
M.p.: 145-6° C.
IR (nujol): 3404 (NH$_2^+$), 1629 (C=O) cm$^{-1}$.
NMR (d$_6$-DMSO): δ (ppm) 9.04 (bs, 2H); 7.99 (s, 1H); 7.77 (s, 2H); 7.35 (dd, 1H); 6.99 (dd, 1H); 6.91 (dt, 1H); 5.09 (bt, 1H); 4.75 (bd, 2H); 4.58 (d, 1H); 4.43 (d, 1H);. 3.64 (bm, 1H); 3.45-3.3 (m, 3H); 3.11 (dd, 1H); 2.81 (s, 3H); 2.27 (s, 3H); 2.17 (bm, 1H); 2.1 (bm, 2H); 1.69 (m, 1H).
MS (ES/+): m/z=538 [MH—HCl]$^+$.

EXAMPLE 7b

A solution of diastereoisomer 2 (32 mg) in dry Et2O (2 mL) was treated with hydrochloric acid (1M in Et2O—70 μL) at 0°

C. and the resulting solution was stirred under a nitrogen atmosphere for 15 minutes. The solution was concentrated in vacuo and the residue was triturated from Et2O/n-pentane to give the title compound as a white solid (27 mg).

IR (nujol): 3410 (NH$^+$), 1660 (C=O) cm$^{-1}$.

NMR (d$_6$-DMSO): δ (ppm) 9.0-8.8 (bm, 2H); 7.95 (bs, 1H); 7.59 (bs, 2H); 7.20 (dd, 1H); 6.94 (dd, 1H); 6.84 (m 1H); 4.70 (bd, 2H); 4.63 (d, 1H); 4.33 (d, 1H); 4.20 (dd, 1H); 3.51 (m, 1H); 3.37 (bm, 3H); 2.93 (s, 3H); 2.75 (m, 1H); 2.35 (s, 3H); 2.16 (m, 1H); 2.11 (m, 1H); 1.73 (m, 1H); 1.54 (m, 1H).

MS (ES/+): m/z=538 [MH—HCl]$^+$.

EXAMPLE 8

4-(S)—(N-2-Fluoroethyl-N-methylamino)-2-(R)-(4-fluoro-2-methyl-phenyl)-piperidine-1-carboxylic acid, (3,5-bis-trifluoromethyl-benzyl)-methylamide hydrochloride Formaldehyde (37% in water—43 μL), 10% palladium over charcoal (10 mg) and 1 drop of acetic acid were added to a solution of example 7b (28 mg) in MeOH (1.5 mL). The mixture was stirred at r.t. under a hydrogen atmosphere for 1 hour, then it was filtered though celite and concentrated in vacuo. The residue was purified by flash chromatography (AcOEt/MeOH 9:1) to give the desired 4-(S)—(N-2-fluoroethyl-N-methylamino)-2-(R)-(4-fluoro-2-methyl-phenyl)-piperidine-1-carboxylic acid (3,5-bis-trifluoromethyl-benzyl)-methylamide (13 mg) as yellow gum. This material was dissolved in dry Et2O (2 mL), treated with hydrochloric acid (1M in Et2O—0.5 mL) and the resulting solution was stirred under a nitrogen atmosphere for 15 minutes. The solution was concentrated in vacuo and the residue was triturated from Et2O/n-pentane to give the title compound as a white solid (11.6 mg).

M.p.: 80-81° C. (dec)

T.l.c.: AcOEt/MeOH 8:2, Rf=0.37 (free base).

IR (nujol): 3387 (NH$^+$), 1653 (C=O) cm$^{-1}$.

NMR (d$_6$-DMSO): δ (ppm) 10.04 (bm, 1H); 7.96 (s, 1H); 7.6 (s, 2H); 7.28 (dd, 1H); 6.94 (dd, 1H); 6.83 (dt 1H); 4.84 (bd, 2H); 4.64 (d, 1H); 4.37 (d, 1H); 4.22 (bdd, 1H); 3.6 (bm, 2H); 3.54 (bd, 1H); 3.43 (m, 1H); 2.93 (s, 3H); 2.78 (m, 4H); 2.37 (s, 3H); 2.15-2.0 (m, 2H); 1.94 (dt, 1H); 1.65 (dq, 1H).

MS (ES/+): m/z=552 [MH—HCl]$^+$.

EXAMPLE 9

2-(R)-(4-Fluoro-2-methyl-phenyl)-4-(R)-(2-methoxyethylamino)-piperidine-1-carboxylic acid [1-(R)-(3,5-bis-trifluoromethyl-phenyl)-ethyl]-methylamide hydrochloride (9a) and 2-(R)-(4-Fluoro-2-methyl-phenyl)-4-(S)-(2-methoxyethylamino)-piperidine-1-carboxylic acid [1-(R)-(3,5-bis-trifluoromethyl-phenyl)-ethyl]-methylamide hydrochloride (9b)

A solution of intermediate 4a (100 mg), 2-methoxyethylamine (17 μL) and sodium triacetoxyborohydride (65 mg) in dry 1,2-dichloroethane (5 mL) was stirred at 23° C. for 2 hours under a nitrogen atmosphere. The solution was washed with a 5% sodium hydrogen carbonate solution (10 mL) and brine (10 mL). The organic layer was dried and concentrated in vacuo to a residue which was purified by flash chromatography (AcOEt/MeOH 8:2) to give two fractions:

1. diastereoisomer 1 (C-2 and C-4 anti configuration—40 mg)
2. diastereoisomer 2 (C-2 and C-4 syn configuration—20 mg)

EXAMPLE 9a

A solution of diastereoisomer 1 (40 mg) in dry Et2O (3 mL) was treated with hydrochloric acid (1M in Et2O—0.5 mL) and the resulting solution was stirred at 0 C° for 5 minutes. The solution was concentrated in vacuo and the residue was triturated with n-pentane (2 mL) to give the title compound as a white solid (40 mg).

IR (nujol): 3396 (NH$_2^+$), 1640 (C=O) cm$^{-1}$.

NMR (d$_6$-DMSO): δ (ppm) 8.67-8.62 (bs, 2H); 7.99 (s, 1H); 7.76 (s, 2H); 7.34 (dd, 1H); 6.99 (dd, 1H); 6.91 (m, 1H); 5.12 (m, 1H); 5.09 (m, 1H); 3.6-3.4 (m, 4H); 3.16 (m, 3H); 2.25-1.60 (m, 4H); 3.3 (m, 3H); 2.59 (s, 3H); 2.23 (s, 3H); 1.55 (d, 3H);

MS (ES/+): m/z=564 [M-Cl]$^+$.

EXAMPLE 9b

A solution of diastereoisomer 2 (20 mg) in dry Et2O (3 mL) was treated with hydrochloric acid (1M in Et2O—0.5 mL). The resulting solution was stirred at 23 C° for 30 minutes, then it was concentrated in vacuo. The residue was triturated with n-pentane (2 mL) to give the title compound as a white solid (20 mg).

IR (nujol): 3421 (NH$_2^+$), 1656-1650 (C=O) cm$^{-1}$.

NMR (d$_6$-DMSO): δ (ppm) 8.64 (bs, 2H); 7.99 (s, 1H); 7.67 (s, 2H); 7.14 (dd, 1H); 6.94 (dd, 1H); 6.83 (m, 1H); 5.28 (q, 1H); 4.17 (dd, 1H); 3.55 (t, 2H); 3.42 (m, 3H); 3.13 (m, 2H); 2.8-2.7 (m, 2H); 2.2-1.5 (m, 4H); 3.3 (m, 3H); 2.73 (s, 3H); 2.34 (s, 3H); 1.45 (d, 3H);

MS (ES/+): m/z=564 [M-Cl]$^+$.

EXAMPLE 10

2-(R)-(4-Fluoro-2-methyl-phenyl)-4-(R)-methylamino-piperidine-1-carboxylic acid [1-(R)-(3,5-bis-trifluoromethyl-phenyl)-ethyl]-methylamide hydrochloride (10a) and 2-(R)-(4-Fluoro-2-methyl-phenyl)-4-(S)-methylamino-piperidine-1-carboxylic acid [1-(R)-(3,5-bis-trifluoromethyl-phenyl)-ethyl]-methylamide hydrochloride (10b)

Intermediate 4a (120 mg), methylamine (1M solution in THF—2.5 mL) and sodium triacetoxyborohydride (65 mg) in dry 1,2-dichloroethane (5 mL) was stirred at 23° C. for 2 hours under a nitrogen atmosphere. The solution was washed with a 5% sodium hydrogen carbonate solution (10 mL) and brine (10 mL). The organic layer was dried and concentrated in vacuo to a residue which was purified by flash chromatography (AcOEt/MeOH 75:25) to give two fractions:

1. diastereoisomer 1 (40 mg—T.l.c. AcOEt/MeOH 7:3 Rf=0.3)
2. diastereoisomer 2 (20 mg)—T.l.c. AcOEt/MeOH 7:3 Rf=0.21)

EXAMPLE 10a

A solution of diastereoisomer 1 (40 mg) in dry Et2O (3 mL) was treated with hydrochloric acid (1M in Et2O—0.5 mL) and the resulting solution was stirred at 0 C° for 5 minutes. The solution was concentrated in vacuo and the residue was triturated with n-pentane (2 mL) to give the title compound as a white solid (40 mg).

IR (nujol): 3398 (NH$_2^+$), 1627 (C=O) cm$^-$.

NMR (d$_6$-DMSO): δ (ppm) 8.60 (bs, 2H); 7.99 (s, 1H); 7.75 (s, 2H); 7.32 (dd, 1H); 6.99 (dd, 1H); 6.90 (m, 1H); 5.13 (q, 1H); 5.016 (t, 1H); 3.42 (m, 2H); 3.14 (m, 1H); 2.61 (s, 3H); 2.57 (s, 3H); 2.24 (s, 3H); 2.12 (m, 2H); 1.95 (m, 1H); 1.62 (m, 1H); 1.54 (d, 3H).

MS (ES/+): m/z=520 [MH—HCl]

EXAMPLE 10b

A solution of diastereoisomer B (20 mg) in dry Et2O (3 mL) was treated with hydrochloric acid (1M in Et2O—0.5 mL). The solution was concentrated in vacuo and the residue was triturated with n-pentane (2 mL) to give the title compound as a white solid (20 mg).

IR (nujol): 3398 (NH$_2^+$), 1658-1650 (C=O) cm$^{-1}$.

NMR (d$_6$-DMSO): δ (ppm) 8.60 (bs, 2H); 7.99 (s, 1H); 7.67 (s, 2H); 7.15 (dd, 1H); 6.94 (dd, 1H); 6.83 (m, 1H); 5.30 (q, 1H); 4.18 (dd, 1H); 3.42 (m, 1H); 3.26 (m, 1H); 1H); 2.76 (t, 1H); 2.73 (s, 3H); 2.55 (s, 3H); 2.35 (s, 3H); 2.10-2.00 (m, 1H); 1.68 (m, 1H); 1.53 (m, 1H) 1.45 (d, 3H);

MS (ES/+): m/z=520 [MH—HCl]$^+$.

EXAMPLE 11

2-(4-Fluoro-2-methyl-phenyl)-4methylamino-piperidine-1-carboxylic acid (3,5-bis-trifluoromethyl-benzyl)-methylamide (11a—diastereoisomer A) and 2-(4-Fluoro-2-methyl-phenyl)-4-methylamino-piperidine-1-carboxylic acid (3,5-bis-trifluoromethyl-benzyl)-methylamide (11b—diastereoisomer B)

A solution of intermediate 3 (150 mg), methylamine (2M in THF—300 µL) and sodium triacetoxyborohydride (100 mg) in dry THF (6 mL) was stirred at r. t. under a nitrogen atmosphere. After 5 hours further methylamine (2M in THF—300 µL) and sodium triacetoxyborohydride (35 mg) were added. After 3 hours the crude solution was quenched with a 5% sodium hydrogen carbonate solution (5 mL) and taken up with AcOEt (5 mL). The aqueous phase was extracted with AcOEt (3×15 mL) and the combined organic phases were washed with brine (5 mL). The organic layer was dried and concentrated in vacuo to a residue which was purified by flash chromatography (AcOEt/MeOH 85:15) to give 2-(4-fluoro-2-methyl-phenyl)-4-methylamino-piperidine-1-carboxylic acid (3,5-bis-trifluoromethyl-benzyl)-methylamide in two fractions:
1. example 11a (100 mg);
2. example 11b (13 mg).

EXAMPLE 11a

NMR (d$_6$-DMSO): δ (ppm) 7.94 (bs, 1H); 7.65 (bs, 2H); 7.24 (dd, 1H); 6.89 (dd, 1H); 6.79 (dt, 1H); 4.64 (dd, 1H); 4.57 (d, 1H); 4.37 (d, 1H); 3.19 (m, 1H); 3.07 (m, 1H); 2.86 (s, 3H); 2.75 (m, 1H); 2.28 (s, 3H); 2.26 (s, 3H); 1.84 (m, 3H); 1.7-1.5 (m, 1H).

MS (ES/+): m/z=506 [MH]$^+$.

EXAMPLE 11b

NMR (d$_6$-DMSO): δ (ppm) 7.93 (bs, 1H); 7.58 (bs, 2H); 7.19 (dd, 1H); 6.89 (dd, 1H); 6.77 (dt, 1H); 4.62 (d, 1H); 4.33 (d, 1H); 4.13 (dd, 1H); 3.42 (m, 1H); 2.9 (s,3H); 2.69 (m, 1H); 2.55 (bm, 1H); 2.33 (s, 3H); 2.29 (s, 3H); 1.96 (m, 1H); 1.89 (m, 1H); 1.39 (m, 1H); 1.16 (m, 1H).

MS (ES/+): m/z=506 [MH]$^+$.

EXAMPLE 12

2-(4-Fluoro-2-methyl-phenyl)-4-methylamino-piperidine-1-carboxylic acid (3,5-bis-trifluoromethyl-benzyl)-methylamide hydrochloride (diastereoisomer A)

A solution of example 11a (100 mg) in dry Et2O (3 mL) was treated with hydrochloric acid (1M in Et2O—220 µL) at 0° C. The resulting solution was stirred under a nitrogen atmosphere for 15 minutes, then it was concentrated in vacuo. The residue was triturated with Et2O/n-pentane to give the title compound (81 mg) as a white solid.

NMR (d$_6$-DMSO): δ (ppm) 8.66 (bm, 2H); 7.94 (bs, 1H); 7.65 (bs, 2H); 7.24 (dd, 1H); 6.89 (dd, 1H); 6.79 (dt, 1H); 4.64 (dd, 1H); 4.57 (d, 1H); 4.37 (d, 1H); 3.19 (m, 1H); 3.07 (m, 1H); 2.86 (s, 3H); 2.75 (m, 1H); 2.28 (s, 3H); 2.26 (s, 3H); 1.84 (m, 3H); 1.7-1.5 (m, 1H).

MS (ES/+): m/z=506 [MH]$^+$, 370.

EXAMPLE 13

2-(4-Fluoro-2-methyl-phenyl)-4-methylamino-piperidine-1-carboxylic acid (3.5-bis-trifluoromethyl-benzyl)-methylamide hydrochloride (diastereoisomer B)

A solution of example 11b (13 mg) in dry Et2O (2 mL) was treated with hydrochloric acid (1M in Et2O—30 µL) at 0° C. and the resulting solution was stirred under a nitrogen atmosphere for 15 minutes. The solution was concentrated in vacuo and the residue was triturated with Et2O/n-pentane to give the title compound (10 mg) as a white solid.

NMR (d$_6$-DMSO): δ (ppm) 8.65 (bm, 2H); 7.94 (bs, 1H); 7.58 (bs, 2H); 7.19 (dd, 1H); 6.93 (dd, 1H); 6.82 (dt 1H); 4.62 (d, 1H); 4.33 (d, 1H); 4.18 (dd, 1H); 3.49 (m, 1H); 3.25 (bm, 1H); 2.92 (s, 3H); 2.74 (m, 1H); 2.55 (s, 3H); 2.35 (s, 3H); 2.12-2.06(m, 2H); 1.68 (m, 1H); 1.48 (q, 1H).

MS (ES/+): m/z=506 [MH]$^+$, 370.

EXAMPLE 14

4-Amino-2-(4-fluoro-2-methyl-phenyl)-piperidine-1-carboxylic acid (3,5-bis-trifluoromethyl-benzyl)-methylamide hydrochloride (14a—diastereoisomer A) and 4-Amino-2-(4-fluoro-2-methyl-phenyl)-piperidine-1-carboxylic acid (3,5-bis-trifluoromethyl-benzyl)-methylamide hydrochloride (14b—diastereoisomer B)

Methanesulphonyl chloride (20 µL) was added to a solution of 2-(4-fluoro-2-methyl-phenyl)-4-hydroxy-piperidine-1-carboxylic acid (3,5-bis-trifluoromethyl-benzyl)-methylamide (intermediate 11a and 11b—mixture of syn and anti diastereoisomers—85 mg) and TEA (50 µL) in dry THF (5 mL) previously cooled to 0° C. under a nitrogen atmosphere. After 1.5 hours, the solution was quenched with brine (4 mL) and extracted with AcOEt (3×5 mL). The organic layer was dried and concentrated in vacuo to a residue which was purified by flash chromatography (CH/AcOEt 7:3) to give methanesulfonic acid, 1-[(3,5-bis-trifluoromethyl-benzyl)-methyl-carbamoyl]-2-(4-fluoro-2-methyl-phenyl)-piperidin-4-yl ester in two fractions:
1. diastereoisomer 1 (11 mg);
2. diastereoisomer 2 (76 mg).

EXAMPLE 14a

Diastereoisomer A

A solution of diastereoisomer 2 (11 mg) and sodium azide (2 mg) in dry DMF (2 mL) was stirred at 80° C. for 4 hours under a nitrogen atmosphere. The crude solution was diluted with AcOEt (5 mL) and washed with cold brine (3×5 mL). The organic layer was dried and concentrated in vacuo to give the crude 4-azido-2-(4-fluoro-2-methyl-phenyl)-piperidine-1-carboxylic acid (3,5-bis-trifluoromethyl-benzyl)-methylamide as a semisolid white residue (20 mg) which was treated with triphenylphosphine (10 mg) in dry THF (3 mL) was stirred at r. t. for 48 hours under a nitrogen atmosphere. Then water (3 µL) was added and the mixture was stirred for further 48 hours. The crude solution was taken up with AcOEt (5 mL) and washed with brine (5 mL). The organic layer was dried and concentrated in vacuo to give the crude 4-amino-2-(4-fluoro-2-methyl-phenyl)-piperidine-1-carboxylic acid (3,5-bis-trifluoromethyl-benzyl)-methylamide. This residue was dissolved in dry Et2O (2 mL), treated with hydrochloric acid (1M in Et2O—100 µL) at 0° C. and the resulting solution was stirred under a nitrogen atmosphere for 15 minutes. The solution was concentrated in vacuo and the residue was triturated with Et2O/n-pentane to give the title compound (9 mg) as a pale yellow solid.

NMR ($d_6$-DMSO): δ (ppm) 9.92 (bs, 1H); 7.9-7.7 (b, 3H); 7.58 (s, 2H); 7.29 (m, 1H); 6.94 (m, 1H); 6.82 (m, 1H); 4.39 (m, 1H); 4.34 (d, 1H); 4.16 (d, 1H); 3.50 (m, 1H); 3.31 (m, 1H); 2.93 (m, 1H); 2.92 (s, 3H); 2.33 (s, 3H); 2.05-1.65 (m, 4H).

MS (ES/+): m/z=492 [M-Cl]$^+$.

EXAMPLE 14b

Diastereoisomer B

A solution of diastereoisomer 1 (75 mg) and sodium azide (13 mg) in dry DMF (5 mL) was stirred at 80° C. for 4 hours under a nitrogen atmosphere. The solution was diluted with AcOEt (5 mL) and washed with cold brine (3×5 mL). The organic layer was dried and concentrated in vacuo to give the crude 4-azido-2-(4-fluoro-2-methyl-phenyl)-piperidine-1-carboxylic acid (3,5-bis-trifluoromethyl-benzyl)-methylamide as a semisolid white residue (80 mg). This residue (60 mg) treated with—triphenylphosphine (30 mg) in dry THF (6 mL) was stirred at r. t. for 48 hours under a nitrogen atmosphere. Then, water (3 µL) was added and the mixture was stirred for further 48 hours. The crude solution was taken up with AcOEt (5 mL) and washed with brine (5 mL). The organic layer was dried and concentrated in vacuo to give the crude 4-amino-2-(4-fluoro-2-methyl-phenyl)-piperidine-1-carboxylic acid (3,5-bis-trifluoromethyl-benzyl)-methylamide. This residue was dissolved in dry Et2O (2 mL), treated with hydrochloric acid (1M in Et2O—300 µL) at 0° C. and the resulting solution was stirred under a nitrogen atmosphere for 15 minutes. The solution was concentrated in vacuo and the residue was triturated with Et2O/n-pentane to give the title compound (10 mg) as a white solid.

NMR ($d_6$-DMSO): δ (ppm) 7.98 (s, 1H); 7.9-7.7 (b, 3H); 7.74 (s, 2H); 7.31 (m, 1H); 6.98 (m, 1H); 6.90 (m, 1H); 4.93 (t, 1H); 4.57 (d, 1H); 4.42 (d, 1H); 3.56 (m, 1H); 3.30 (m, 1H); 3.13 (m, 1H); 2.83 (s, 3H); 2.26 (s, 3H); 2.02-1.62 (m, 4H).

MS (ES/+): m/z=492 [M-Cl]$^+$, 475 [M-HCl—NH$_3$]$^+$.

EXAMPLE 15

4-(R)-Cyclobutylamino-2-(R)-(fluoro-2-methyl-phenyl)-piperidine-1-carboxylic acid [1-(R)-(3,5-bis)-trifluoromethyl-phenyl)-ethyl]-methylamide hydrochloride (15a) and 4-(S)-Cyclobutylamino-2-(R)-(4-fluoro-2-methyl-phenyl)-piperidine-1-carboxylic acid [1-(R)-(3,5-bis)-trifluoromethyl-phenyl)-ethyl]-methylamide hydrochloride (15b)

A solution of intermediate 4a (120 mg), cyclobutylamine (20.4 µL) and sodium triacetoxyborohydride (75.5 mg) in dry 1,2-dichloroethane (10 mL) was stirred at 23° C. for 4 hours under a nitrogen atmosphere. The solution was washed with a 5% sodium hydrogen carbonate solution (10 mL) and brine (10 mL). The organic layer was dried and concentrated in vacuo to a residue that was purified by flash chromatography (AcOEt/MeOH 9:1) to give:
1. diastereoisomer 1 (55.9 mg—T.l.c.: AcOEt/MeOH 8:2 Rf=0.44),
2. a mixture of the two diastereoisomer (33.3 mg)
3. diastereoisomer 2 (22.9 mg—T.l.c.: AcOEt/MeOH 8:2 Rf=0.3).

EXAMPLE 15a

A solution of diastereoisomer 1 (53.5 mg) in dry Et2O (10 mL) was treated with hydrochloric acid (1M in Et2O—2 mL) and the resulting solution was stirred at 23° C. for 30 minutes. The solution was concentrated in vacuo to give the title compound as a white solid (54 mg).

M.p.: 68-70° C. (dec).

IR (nujol): 3400, 3000-2400 (NH$_2^+$), 1637 (C=O) cm$^{-1}$.

NMR ($d_6$-DMSO): δ (ppm) 8.79 (bs, 2H); 7.99 (s, 1H); 7.74 (s, 2H); 7.28 (dd, 1H); 6.97 (dd, 1H); 6.89 (dd, 1H); 5.13 (q, 1H); 4.98 (bt, 1H); 3.83 (m, 1H); 3.45-3.35 (m, 2H); 3.11 (m, 1H); 2.62 (s, 3H); 2.25 (s, 3H); 2.18 (2m, 4H); 1.92-1.76 (2m, 2H); 1.61 (m, 2H); 1.53 (d, 3H); 1.24 (m, 1H); 0.84 (m, 1H).

MS (ES/+): m/z=560 [MH—HCl]$^+$.

EXAMPLE 15b

A solution of diastereoisomer 2 (21.2 mg) in dry Et2O (5 mL) was treated with hydrochloric acid (1M in Et2O—2 mL). The resulting mixture was stirred at 23° C. for 15 minutes, then filtered to give the title compound as a whitish solid (22 mg).

M.p.: 211-213° C. (dec).

IR (nujol): 3400-2500 (NH$_2^+$), 1664 (C=O) cm$^{-1}$.

NMR ($d_6$-DMSO): δ (ppm) 9.07 (bs, 2H); 7.98 (bs, 1H); 7.65 (bs, 2H); 7.13 (m, 1H); 6.93 (m, 1H); 6.81 (m, 1H); 5.27 (m, 1H); 4.17 (m, 1H); 3.80 (bm, 1H); 3.4-3.3 (m, 2H); 2.77 (m, 1H); 2.72 (m, 3H); 2.33 (s, 3H); 2.17 (m, 4H); 2.07-1.99 (m, 2H); 1.8-1.4 (m, 2H); 1.44 (d, 3H); 1.24 (m, 1H); 0.84 (m, 1H)

MS (ES/+): m/z=560 .

EXAMPLE 16

4-(R)-Cyclopropylamino-2-(R)-(4-fluoro-2-methyl-phenyl)-piperidine-1-carboxylic acid [1-(R)-(3,5-bis-trifluoromethyl-phenyl)-ethyl]-methylamide hydrochloride (16a) and 4-(S)-Cyclopropylamino-2-(R)-(4-fluoro-2-methyl-phenyl)-piperidine-1-carboxylic acid [1-(R)-(3,5-bis-trifluoromethyl-phenyl)-ethyl]-methylamide hydrochloride (16b)

A solution of intermediate 4a (120 mg), cyclopropylamine (16.6 µL) and sodium triacetoxyborohydride (78.2 mg) in dry 1,2-dichloroethane (5 mL) was stirred at 23° C. for 2 hours under a nitrogen atmosphere. The solution was washed with a 5% sodium hydrogen carbonate solution (10 mL) and brine (10 mL). The organic layer was dried and concentrated in vacuo to a residue that was purified by flash chromatography (AcOEt/MeOH 85:15) to give three fractions:
1. diastereoisomer 1 (59.5 mg—T.l.c.: AcOEt/MeOH 7:3 Rf=0.40),
2. a mixture of the two diastereoisomer (20.0 mg)
3. diastereoisomer 2 (32.0 mg—T.l.c.: AcOEt/MeOH 7:3 Rf=0.37).

EXAMPLE 16a

A solution of diastereoisomer 1 (59.5 mg) in dry Et2O (5 mL) was treated with hydrochloric acid (1M in Et2O—1 mL) and the resulting solution was stirred at 23° C. for 30 minutes. The solution was concentrated in vacuo to give the title compound as a white solid (59.5 mg).

IR (nujol): 3404, ($NH_2^+$), 1639 (C=O) $cm^{-1}$.

NMR ($d_6$-DMSO): δ (ppm) 8.86 (bs, 2H); 8.77 (bs, 1H); 8.00 (s, 1H); 7.76 (s, 2H); 7.34 (dd, 1H); 6.99 (dd, 1H); 6.92 (dt, 1H); 5.15 (q, 1H); 5.04 (bt, 1H); 3.66 (bm, 1H); 3.42 (bm, 1H); 3.14 (dt, 1H); 2.74 (bm, 1H); 2.63 (s, 3H); 2.25 (s, 3H); 2.19 (bm, 2H); 2.02 (bm, 1H); 1.68 (m, 1H); 1.55 (d, 3H); 0.84 (bm, 2H); 0.79 (bm, 2H).

MS (ES/+): m/z=546 [MH—HCl]$^+$.

EXAMPLE 16b

A solution of diastereoisomer 2 (32.0 mg) in dry Et2O (5 mL) was treated with hydrochloric acid (1M in Et2O—1 mL). The resulting mixture was stirred at 23° C. for 15 minutes, then filtered and treated with further diethyl ether to give the title compound as a whitish solid (20 mg).

IR (nujol): 3383 ($NH_2^+$), 1650 (C=O) $cm^{-1}$.

NMR ($d_6$-DMSO): δ (ppm) 9.00 (sa, 2H); 7.99 (s, 1H); 7.67 (s, 2H); 7.15 (dd, 1H); 6.94 (dd, 1H); 6.83 (m, 1H); 5.29 (q, 1H); 4.21 (dd, 1H); 2.73 (s, 3H); 2.45 (m, 2H); 2.35 (s, 3H); 2.9-2.2 (m, 2H); 1.8-0.7 (m, 8H); 1.45 (d, 3H).

MS (ES/+): m/z=546 [MH—HCl]$^+$.

EXAMPLE 17

2-(R)-(4-Fluoro-2-methyl-phenyl)-4-(R,S)-[methyl-(1-methyl-piperidin-4-yl)-amino]-piperidine-1-carboxylic acid [1-(R)-(3,5-bis-trifluoromethyl-phenyl)-ethyl]-methylamide hydrochloride A solution of intermediate 4a (120 mg), 1-methyl-4-(methylamino)-piperidine (34.6 µL) and sodium triacetoxyborohydride (75.5 mg) in dry 1,2-dichloroethane (2.5 mL) was stirred at 23° C. overnight under a nitrogen atmosphere. The solution was washed with a 5% sodium hydrogen carbonate solution (10 mL) and brine (10 mL). The organic layer was dried and concentrated in vacuo to a residue which was purified by flash chromatography (AcOEt/MeOH from 10:0 to 1:1) to give the 2-(4-fluoro-2-methyl-phenyl)-4-[methyl-(1-methyl-piperidin-4-yl)-amino]-piperidine-1-carboxylic acid [1-(R)-(3,5-bis-trifluoromethyl-phenyl)-ethyl]-methylamide (43 mg as a mixture of diastereoisomer A and diastereoisomer B) which was dissolved in dry Et2O (5 mL) and treated with hydrochloric acid (1M in Et2O—1 mL). The resulting mixture was stirred at 23° C. for 30 minutes, then it was concentrated in vacuo. The residue was triturated with Et2O to give the title compound (25 mg) as a white solid and as a mixture of anti/syn 60:40.

NMR ($d_6$-DMSO): δ (ppm) 10.40 and 9.50 (2bs, 2H); 7.90 (d, 1H); 7.73 and 7.67 (2s, 2H); 7.30 and 7.22 (2bt, 1H); 6.94-6.75 (2m, 2H); 5.31 and 5.11 (2q, 1H); 5.00 and 4.24 (2bd, 1H); 2.36 and 2.27 (2s, 3H); 1.53 and 1.46 (2d, 3H); 2.74-2.61 (6s, 9H); 3.40-1.75 (14m, 16H).

MS (ES/+): m/z=617 [MH—HCl]$^+$.

EXAMPLE 18

4-Benzylamino-2-(4-fluoro-2-methyl-phenyl)-piperidine-1-carboxylic acid (3,5-bis-trifluoromethyl-benzyl)-methylamide (18a—diastereoisomer A) and 4-Benzylamino-2-(4-fluoro-2-methyl-phenyl)-piperidine-1-carboxylic acid (3,5-bis-trifluoromethyl-benzyl)-methylamide (18 b—diastereoisomer B)

A solution of intermediate 3 (30 mg), benzylamine (7.5 µL), acetic acid (6 µL) and sodium triacetoxyborohydride (22 mg) in dry 1,2-dichloroethane (2 mL) was stirred at r.t. under a nitrogen atmosphere. After 0.5 hours further benzylamine (7.5 µL) and sodium triacetoxyborohydride (22 mg) were added. After 1.5 hours the crude solution was quenched with a 1N potassium hydroxide solution (2 mL) and taken up with AcOEt (5 mL). The aqueous phase was extracted with AcOEt (3×5 mL) and the combined organic phases were washed with brine (5 mL). The organic layer was dried and concentrated in vacuo to a residue which was purified by flash chromatography (AcOEt/MeOH 9:1) to give two fractions:
1. diastereoisomer A (24 mg—T.l.c.: AcOEt/MeOH 9:1 Rf=0.45),
2. diastereoisomer B (10 mg—T.l.c.: AcOEt/MeOH 9:1 Rf=0.3).

EXAMPLE 18a (diastereoisomer A)

NMR ($d_6$-DMSO): δ (ppm) 7.95 (bs, 1H); 7.60 (bs, 2H); 7.20 (m, 6H); 6.90 (m, 1H); 6.79 (m, 1H); 4.64 (d, 1H); 4.30 (d, 1H); 4.10 (m, 1H); 3.65 (bs, 2H); 3.15 (m, 1H); 2.90 (s, 3H); 2.65 (m, 1H); 2.35 (m, 1H); 2.25 (s, 3H); 1.90 (m, 2H); 1.6-1.5 (m, 2H).

MS (ES/+): m/z=582 [MH]$^+$, 446.

EXAMPLE 18b

Diastereoisomer B

NMR ($d_6$-DMSO): δ (ppm) 7.93 (bs, 1H); 7.58 (bs, 2H); 7.25 (m, 6H); 6.88 (dd, 1H); 6.77 (dt, 1H); 4.62 (d, 1H); 4.32 (d, 1H); 4.09 (dd, 1H); 3.71 (s, 2H); 3.40 (m, 1H); 2.90 (s, 3H); 2.65 (m, 1H); 2.59 (m, 1H); 2.31 (s, 3H); 1.95(m, 2H); 1.43 (m, 1H); 1.20 (m, 1H).

MS (ES/+): m/z=582 [MH]$^+$, 446.

EXAMPLE 19

4-[(1,3-Dioxolan-2-yl)-methyl]-amino-2-(4-fluoro-2-methyl-phenyl)-piperidine-1-carboxylic acid, (3,5-bis-trifluoromethyl-benzyl)-methylamide A solution of intermediate 3 (10 mg), 2-(aminomethyl)-1,3-dioxolane (2.09 mg), sodium triacetoxyborohydride (6.45 mg) and acetic acid (1,7 µl) in dry 1,2-dichloroethane (400 µl) was stirred at 23° C. for 18 hours. The solution was diluted with DCM (1 mL) and washed with a 0.5N solution of sodium hydroxide (1 mL). The two phases were separated using a Whatman filter tube with polypropylene filter and the organic solution was then passed through a SCX cartridge (Varian, 100 mg). The cartridge was washed with MeOH (3 mL) and the product was then released by adding a 0.25M solution of ammonia in MeOH (1 mL) and washing with MeOH (1 mL). The solution was concentrated in vacuo to give the title compound (7 mg) as a mixture of diastereoisomers A and B in ratio 70:30.

Diastereoisomer A:
NMR (CDCl$_3$): δ (ppm) 7.75 (bs, 1H); 7.53 (s, 2H); 7.25 (dd, 1H); 6.85-6.78 (m, 2H); 4.96 (dd, 1H); 4.57 (d, 1H); 4.43 (d, 1H); 5.01 (t, 1H); 3.99 (m, 2H); 3.90 (m, 2H); 2.88 (s, 3H); 2.34 (s, 3H); 2.84 (d, 2H); 3.48-3.38 and 3.18-3.08 and 2.14-1.50(m, 7H).
MS (ES/+): m/z=577.

Diastereoisomer B:
NMR (CDCl$_3$): δ (ppm) 7.75 (bs, 1H); 7.67 (bs, 1H); 7.42 (s, 2H); 7.17 (dd, 1H); 6.85-6.78 (m, 2H); 4.28 (dd, 1H); 4.65 (d, 1H); 4.37 (d, 1H); 4.99 (t, 1H); 3.99 (m, 2H); 3.90 (m, 2H); 2.96 (s, 3H); 2.43 (s, 3H); 2.86 (d, 2H); 3.48-3.38 and 3.18-3.08 and 2.14-1.50(m, 7H).
MS (ES/+): m/z=577.

EXAMPLE 20

4-(R)-N-2-Fluoroethyl-N-methylamino)-2-(R)-(4-fluoro-2-methyl-phenyl)-piperidine-1-carboxylic acid (3,5-bis-trifluoromethyl-benzyl)-methylamide hydrochloride Formaldehyde (37% in water—208 µL), 10% palladium over charcoal (34 mg) and 2 drops of acetic acid were added to a solution of Example 7a (98 mg) in MeOH (5 mL). The mixture was stirred at r.t. under a hydrogen atmosphere for 1 hour, then it was filtered though celite and concentrated in vacuo. The residue was purified by flash chromatography (AcOEt/MeOH 9:1) to give the 4-(R)-(N-2-fluoroethyl-N-methylamino)-2-(R)-(4-fluoro-2-methyl-phenyl)-piperidine-1-carboxylic acid (3,5-bis-trifluoromethyl-benzyl)-methylamide (85 mg—T.l.c.: AcOEt/MeOH 8:2, Rf=0.37). This material was dissolved in dry Et2O (5 mL), treated with hydrochloric acid (1M in Et2O—0.5 mL) and the resulting solution was stirred under a nitrogen atmosphere for 15 minutes. The solution was concentrated in vacuo and the residue was triturated from Et2O/n-pentane to give the title compound as a white solid (85 mg).
IR (nujol): 3348 (NH$^+$), 1628 (C=O) cm$^{-1}$.
NMR (d$_6$-DMSO): δ (ppm) 8.9 (bs, 1H); 7.99 (s, 1H); 7.78 (s, 2H); 7.35 (dd, 1H); 7.0 (dd, 1H); 6.92 (dt 1H); 5.08 (bt, 1H); 4.73 (d, 2H); 4.58 (d, 1H); 4.43 (d, 1H); 3.65 (bm, 1H); 3.42-3.3 (m, 3H); 3.11 (dt, 1H); 2.81 (s, 3H); 2.5 (m, 3H); 2.27 (s, 3H); 2.17 (m, 1H); 2.11 (m, 1H); 2.06 (m, 1H); 1.69 (m, 1H).
MS (ES/+): m/z=552 [MH—HCl]$^+$.

EXAMPLE 21

4-(R)-(Carbamoylmethyl-amino)-2-(R)-(4-fluoro-2-methyl-phenyl)-piperidine-1-carboxylic acid (3,5-bis-trifluoromethyl-benzyl)-methylamide hydrochloride (21a) and

4-(S)-(Carbamoylmethyl-amino)-2-(R)-(4-fluoro-2-methyl-phenyl)-piperidine-1-carboxylic acid (3,5-bis-trifluoromethyl-benzyl)-methylamide hydrochloride (21b)

A solution of intermediate 10 (120 mg), glycinamide hydrochloride (81 mg) and TEA (102 µL) in dry 1,2-dichloroethane (2 mL) and acetonitrile (2 mL) was stirred at r.t. for 1 hour under a nitrogen atmosphere. Then sodium triacetoxyborohydride (78 mg) was added and the mixture was stirred at 23° C. for 18 hours. The solution was washed with a 5% sodium hydrogen carbonate solution (10 mL) and extracted with DCM (2×10 mL). The combined organic extracts were washed with brine (10 mL), dried and concentrated in vacuo to a residue, which was purified by flash chromatography (AcOEt/MeOH 8:2) to give two fractions:
1. diastereoisomer 1 (47 mg—T.l.c.: AcOEt/MeOH 8:2, Rf=0.22);
2. diastereoisomer 2 (35 mg—T.l.c.: AcOEt/MeOH 8:2 Rf=0.13).

EXAMPLE 21a

A solution of diastereoisomer 1 (47 mg) in dry Et2O (5 mL) was treated with hydrochloric acid (1M in Et2O—0.1 mL). The resulting mixture was stirred at 0° C. for 15 minutes, then filtered to give the title compound as a yellow solid (41.5 mg).
M.p.: 130-1° C.
IR (nujol): 3325 (NH$_2^+$), 1697 (C=O) cm$^{-1}$.
NMR (d$_6$-DMSO): δ (ppm) 8.97 (bs, 1H); 8.92 (bs, 1H); 7.98 (s, 1H); 7.85 (s, 1H); 7.78 (s, 2H); 7.62 (s, 1H); 7.34 (td, 1H); 7.0 (dd, 1H); 6.91 (td, 1H); 5.1 (t, 1H); 4.57 (d, 1H); 4.41 (d, 1H); 3.74 (bs, 2H); 3.59 (bs, 1H); 3.46 (bd, 1H); 3.09 (t, 1H); 2.78 (s, 3H); 2.26 (s, 3H); 2.19 (m, 1H); 2.03 (m, 2H); 1.66 (m, 1H).
MS (ES/+): m/z=549 [M+H]$^+$.

EXAMPLE 21b

A solution of diastereoisomer 2 (35 mg) in dry Et2O (5 mL) was treated with hydrochloric acid (1M in Et2O—0.1 mL). The resulting mixture was stirred at 0° C. for 15 minutes, then filtered to give the title compound as a yellow solid (27 mg).
M.p.: 100-1° C.
IR (nujol): 3300-3100 (NH$_2^+$), 1695 (C=O) cm$^{-1}$.
NMR (d$_6$-DMSO): δ (ppm) 8.97 (bd, 2H); 7.94 (s, 1H); 7.81 (s, 1H); 7.59 (s, 3H); 7.18 (t, 1H); 6.94 (d, 1H); 6.83 (t, 1H); 4.64 (d, 1H); 4.33 (d, 1H); 4.17 (dd, 1H); 3.71 (bm, 2H); 3.51 (d, 1H); 3.41 (m, 1H); 2.92 (s, 3H); 2.72 (t, 1H); 2.34 (s, 3H); 2.11 (d, 1H); 2.05 (d, 1H); 1.77 (m, 1H); 1.59 (m, 1H).
MS (ES/+): m/z=549 [M+H]$^+$.

EXAMPLE 22

2-(R)-(4-Fluoro-2-methyl-phenyl)-4-(R)-morpholino-piperidine-1-carboxylic acid (3,5-bis-trifluoromethyl-benzyl)-methylamide (22a)

2-(R)-(4-Fluoro-2-methyl-phenyl)-4-(S)-morpholino-piperidine-1-carboxylic acid (3,5-bis-trifluoromethyl-benzyl)-methylamide (22b)

A solution of intermediate 10 (500 mg) and morpholine (230 µL) in dry acetonitrile (5 mL) was stirred at r.t. for 1 hour under a nitrogen atmosphere. Then sodium triacetoxyborohydride (390 mg) was added and the mixture was stirred at 23° C. for 18 hours. The solution was washed with a saturated sodium hydrogen carbonate solution and extracted with AcOEt. The organic extract was washed with brine, dried and concentrated in vacuo to a residue, which was purified by flash chromatography (AcOEt/MeOH 97:3) to give two fractions:

1. example 22a (187 mg);
2. example 22b (209 mg).

EXAMPLE 22a

NMR (CDCl$_3$): δ (ppm) 7.77 (bs, 1H); 7.55 (bs, 2H); 7.27 (m, 1H); 6.83 (m, 2H); 5.06 (dd, 1H); 4.51 (m, 2H); 3.75 (m, 4H); 3.52 (m, 1H); 3.15 (m, 1H); 2.88 (s, 3H); 2.6 (m, 1H); 2.55 (m, 4H); 2.34 (s, 3H); 2.04-1.88 (2m, 4H).

EXAMPLE 22b

NMR (CDCl$_3$): δ (ppm) 7.76 (bs, 1H); 7.44 (bs, 2H); 7.18 (dd, 1H); 6.83 (m, 2H); 4.67-4.4 (2d, 2H); 4.3 (dd, 1H); 3.71 (m, 4H); 3.48 (m, 1H); 2.98 (s, 3H); 2.86 (m, 1H); 2.58 (m, 4H); 2.5 (m, 1H); 2.45 (s, 3H); 2.04-1.98 (2m, 4H); 1.67 (dq, 1H); 1.48 (q, 1H).

EXAMPLE 23

2-(R)-(4-Fluoro-2-methyl-phenyl)-4-(R)-morpholino-piperidine-1-carboxylic acid (3,5-bis-trifluoromethyl-benzyl)-methylamide A solution of example 22a (175 mg) in dry Et2O (3 mL) previously cooled to 0° C. was treated with hydrochloric acid (1M in Et2O—343 μL). The resulting mixture was stirred at 0° C. for 30 minutes, then pentane (5 mL) was added and the solid was filtered off to give the title compound as a white solid (102 mg).

NMR (d$_6$-DMSO): δ (ppm) 10.31 (bd, 1H); 7.99(s, 1H); 7.82(s, 2H); 7.3 (dd, 1H); 7.02 (dd, 1H); 6.94 (dd, 1H); 5.25 (s, 1H); 4.59 (d, 1H); 4.42 (d, 1H); 3.99 (dd, 2H); 3.73 (d, 1H); 3.59 (dd, 1H); 3.53 (d, 1H); 3.44 (d, 1H); 3.08 (dd, 3H); 2.75 (s, 3H); 2.24 (s, 3H); 2.17 (m, 3H); 1.68 (dd, 1H).

EXAMPLE 24

2-(R)-(4-Fluoro-2-methyl-phenyl)-4-(S)-morpholino-piperidine-1-carboxylic acid (3,5-bis-trifluoromethyl-benzyl)-methylamide A solution of example 22b (202 mg) in dry Et2O (7 mL) and THF (0.5 mL) previously cooled to 0° C. was treated with hydrochloric acid (1M in Et2O—396 μL). The resulting mixture was stirred at 0° C. for 30 minutes, then concentrated in vacuo to give the title compound as a white solid (199 mg).

NMR (d$_6$-DMSO): δ (ppm) 10.97 (bd, 1H); 7.95 (s, 1H); 7.6 (s, 2H); 7.25 (dd, 1H); 6.94 (dd, 1H); 6.93 (dd, 1H); 4.63 (d, 1H); 4.36 (d, 1H); 4.19 (d, 1H); 3.94 (dd, 2H); 3.8 (m, 2H); 3.55 (d, 1H); 3.45 (dd, 1H); 3.42 (d, 2H); 3.07 (dd, 2H); 2.93 (s, 3H); 2.73 (dd, 1H); 2.37 (dd, 2H); 2.21 (dd, 2H); 1.91 (dd, 1H); 1.7 (dd, 1H).

EXAMPLE 25

2-(R)-(4-Fluoro-2-methyl-phenyl)-4-(R)-morpholino-piperidine-1-carboxylic acid 1-[(R)-(3.5-bis-trifluoromethyl-phenyl)-ethyl]-methylamide (25a)

2-(R)-(4-Fluoro-2-methyl-phenyl)-4-(S)-morpholino-piperidine-1-carboxylic acid 1-[(R)-(3,5-bis-trifluoromethyl-phenyl)-ethyl]-methylamide (25b)

A solution of intermediate 4a (238 mg) and morpholine (106 μL) in dry acetonitrile (5 mL) was stirred at r.t. for 1 hour under a nitrogen atmosphere. Then sodium triacetoxyborohydride (179 mg) was added and the mixture was stirred at 23° C. for 18 hours. The solution was washed with a saturated sodium hydrogen carbonate solution and extracted with AcOEt. The organic extract was washed with brine, dried and concentrated in vacuo to a residue, which was purified by HPLC (Column Chiralcel OD 25 cm×20 mm, n-hexane/EtOH 97:3, flow 7.5 mL/min, λ=225 nm) to give three fractions:

1. example 25b (119 mg);
2. mixture of example 25a and 25b (30 mg);
3. example 25a (76 mg).

EXAMPLE 25a

NMR (d$_6$-DMSO): δ (ppm) 7.97 (s, 1H); 7.71 (s, 2H); 7.26 (dd, 1H); 6.91 (dd, 1H); 6.82 (m, 1H); 5.16 (q, 1H); 4.83 (m, 1H); 3.59 (m, 4H); 3.3 (m, 1H); 3.15 (m, 1H; 2.61 (s, 3H); 2.41 (m, 4H); 2.4 (m, 1H); 2.24 (s, 3H); 1.9-1.65 (m, 4H); 1.49 (d, 3H).

HPLC: column Chiralcel OD 25 cm×4.6 mm; mobile phase: n-hexane/EtOH 97:3, flow 1 mL/min, λ=225 nm; retention time 7.54 minutes.

EXAMPLE 25b

NMR (d$_6$-DMSO): δ (ppm) 7.98 (s, 1H); 7.67 (s, 2H); 7.16 (dd, 1H); 6.9 (dd, 1H); 6.74 (m, 1H); 5.32 (q, 1H); 4.12 (dd, 1H); 3.51 (m, 4H); 3.4 (m, 1H); 2.7 (m, 4H); 2.44 (m, 4H); 2.4 (m, 1H); 2.33 (s, 3H); 1.9 (m, 2H); 1.6 (m, 1H); 1.45 (d, 3H); 1.37 (m, 1H).

HPLC: column Chiralcel OD 25 cm×4.6 mm; mobile phase: n-hexane/EtOH 97:3, flow 1 mL/min, λ=225 nm; retention time 6.61 minutes.

EXAMPLE 26

2-(R)-(4-Fluoro-2-methyl-phenyl)-4-(R)-morpholino-piperidine-1-carboxylic acid 1-[(R)-(3,5-bis-trifluoromethyl-phenyl)-ethyl]-methylamide hydrochloride A solution of example 25a (62 mg) in dry Et2O (1.5 mL) previously cooled to 0° C. was treated with hydrochloric acid (1M in Et2O—119 μL). The resulting mixture was stirred at 0° C. for 30 minutes, then pentane (4 mL) was added and the solid was filtered off to give the title compound as a white solid (56 mg).

NMR (d$_6$-DMSO): δ (ppm) 10.27 (bs, 1H); 8.0 (bs, 1H); 7.78 (bs, 2H); 7.38 (dd, 1H); 7.01 (dd, 1H); 6.93 (dt, 1H); 5.25 (t, 1H); 5.07 (q, 1H); 3.98-3.74 (2t, 4H); 3.63, 3.5, 3.42 (3m, 4H); 3.13 (m, 3H); 2.56 (s, 3H); 2.34 (m, 1H); 2.22 (s, 3H); 2.15 (m, 1H); 1.68 (m, 1H); 1.57 (d, 3H).

EXAMPLE 27

2-(R)-(4-Fluoro-2-methyl-phenyl)-4-(S)-morpholino-piperidine-1-carboxylic acid 1-[(R)-(3,5-bis-trifluoromethyl-phenyl)-ethyl]-methylamide hydrochloride A solution of example 25b (101 mg) in dry Et2O (2 mL) previously cooled to 0° C. was treated with hydrochloric acid (1M in Et2O—190 μL). The resulting mixture was stirred at 0° C. for 1 hour, then pentane (5 mL) was added and the solid was filtered off to give the title compound as a white solid (93 mg).

NMR ($d_6$-DMSO): δ (ppm) 10.62 (bs, 1H); 7.99 (bs, 1H); 7.68 (bs, 1H); 7.21 (dd, 1H); 6.95 (dd, 1H); 6.83 (dt, 1H); 5.31 (q, 1H); 4.18 (dd, 1H); 3.95 (t, 2H); 3.76 (t, 2H); 3.45 (m, 4H); 3.08 (m, 2H); 2.77 (t, 1H); 2.74 (s, 3H); 2.36 (s, 3H); 2.18 (m, 2H); 1.87 (m, 1H); 1.74 (q, 1H); 1.46 (d, 3H).

EXAMPLE 28

2-(R)-(4-Fluoro-2-methyl-phenyl)-4-(R)-morpholino-piperidine-1-carboxylic acid 1-[(S)-(3,5-bis-trifluoromethyl-phenyl)-ethyl]-methylamide (28a)

2-(R)-(4-Fluoro-2-methyl-phenyl)-4-(S)-morpholino-piperidine-1-carboxylic acid 1-[(S)-(3,5-bis-trifluoromethyl-phenyl)-ethyl]-methylamide (28b)

A solution of intermediate 5b (290 mg) and morpholine (130 μL) in dry acetonitrile (5 mL) was stirred at r.t. for 1 hour under a nitrogen atmosphere. Then sodium triacetoxyborohydride (217 mg) was added and the mixture was stirred at 23° C. for 18 hours. The solution was washed with a saturated sodium hydrogen carbonate solution and extracted with AcOEt. The organic extract was washed with brine, dried and concentrated in vacuo to a residue, which was purified by flash chromatography (AcOEt/MeOH 97:3) to give:
1. example 28a (87 mg);
2. example 28b (100 mg).

EXAMPLE 28a

NMR (CDCl$_3$): δ (ppm) 7.75 (bs, 1H); 7.6 (bs, 2H); 7.24 (dd, 1H); 6.83 (m, 2H); 5.54 (q, 1H); 5.03 (dd, 1H); 3.76 (m, 4H); 3.44 (m, 1H); 3.09 (m, 1H); 2.72 (s, 3H); 2.59 (m, 1H); 2.56 (m, 4H); 2.35(s, 3H); 2.05 (m, 2H); 1.85 (m, 2H); 1.54 (d, 3H).

EXAMPLE 28b

NMR (CDCl$_3$): δ (ppm) 7.73 (bs, 1H); 7.44 (bs, 2H); 7.14 (dd, 1H); 6.84 (dd, 1H); 6.79 (dt, 1H); 5.62 (q, 1H); 4.3 (dd, 1H); 3.71 (m, 4H); 3.44 (m, 1H); 2.83 (m, 1H); 2.82 (s, 3H); 2.57 (m, 4H); 2.45 (m+s, 4H); 2.01 (m, 2H); 1.64 (m, 1H); 1.52 (d, 3H); 1.45 (q, 1H).

EXAMPLE 29

2-(R)-(4-Fluoro-2-methyl-phenyl)-4-(R)-morpholino-piperidine-1-carboxylic acid 1-[(S)-(3,5-bis-trifluoromethyl-phenyl)-ethyl]-methylamide hydrochloride A solution of example 28a (80 mg) in dry Et2O (1.5 mL) previously cooled to 0° C. was treated with hydrochloric acid (1M in Et2O—150 μL). The resulting mixture was stirred at 0° C. for 1 hour, then it was filtered to give the title compound as a pale yellow solid (71 mg).

NMR ($d_6$-DMSO): δ (ppm) 10.17 (bs, 1H); 7.99 (s, 1H); 7.84 (s, 2H); 7.41 (dd, 1H); 7.04 (dd, 1H); 6.94 (dt, 1H); 5.29 (q, 1H); 5.25 (m, 1H); 4.01 (m, 2H); 3.76 (m, 2H); 3.73 (m, 1H); 3.5 (m, 2H); 3.48 (m, 1H); 3.13 (m, 2H); 2.97 (t, 3H); 2.63 (s, 1H); 2.34 (m, 2H); 2.23 (s, 3H); 2.16 (m, 1H); 1.66 (m, 1H); 1.54 (d, 3H).

EXAMPLE 30

2-(R)-(4-Fluoro-2-methyl-phenyl)-4-(S)-morpholino-piperidine-1-carboxylic acid 1-[(S)-(3,5-bis-trifluoromethyl-phenyl)-ethyl]-methylamide hydrochloride A solution of example 28b (90 mg) in dry Et2O (1.5 ML) previously cooled to 0° C. was treated with hydrochloric acid (1M in Et2O—172 μL). The resulting mixture was stirred at 0° C. for 1 hour, then pentane (5 mL) was added and the mixture was filtered to give the title compound as a white solid (89 mg).

NMR ($d_6$-DMSO): δ (ppm) 10.55 (bs, 1H); 7.94 (s, 1H); 7.54 (s, 2H); 7.21 (dd, 1H); 6.93 (dd, 1H); 6.8 (dt, 1H); 5.33 (q, 1H); 4.18 (dd, 1H); 3.95-3.75 (2m, 4H); 3.54 (m, 1H); 3.47 (m, 1H); 3.43-3.07 (2m, 4H); 2.84 (s, 3H); 2.68 (t, 1H); 2.36 (s, 3H); 2.2 (m, 2H); 1.88 (dq, 1H); 1.64 (q, 1H); 1.5 (d, 3H).

EXAMPLE 31

4-Cyclopropylamino-1-(4-fluoro-2-methyl-phenyl)-piperidine-2-carboxylic acid (3,5-dichloro-benzyl)-methylamide (31a—diastereoisomer A) and 4-Cyclopropylamino-1-(4-fluoro-2-methyl-phenyl)-piperidine-2-carboxylic acid (3,5-dichloro-benzyl)-methylamide (31b—diastereoisomer B)

Cyclopropylamine (0.012 mL) and sodium triacetoxyborohydride (38.1 mg) were added to a solution of intermediate 5 (50 mg) in anhydrous acetonitrile (3 mL) under a Nitrogen atmosphere. The solution was stirred at r.t. for 2 hours, then further cyclopropylamine (0.006 mL) and sodium triacetoxyborohydride (25.4 mg) were added. The mixture was stirred at 23° C. for 2 days. The solution was diluted with AcOEt (15 mL) and washed with a 5% sodium hydrogen carbonate solution (15 mL) and brine (10 mL). The organic layer was dried and concentrated in vacuo to a residue which was purified by flash chromatography (AcOEt/MeOH 85:15) to give two fractions:
1. example 31a (8.5 mg) as colourless oil
2. example 31b (10.1 mg) as colourless oil.

EXAMPLE 31a

T.l.c.:AcOEt/MeOH 85:15, Rf=0.23.

NMR ($d_6$-DMSO): δ (ppm) 7.36 (bs, 1H); 7.12 (dd, 1H); 6.95 (bs, 2H); 6.89 (bd, 1H); 6.82 (bt, 1H); 4.48 (d, 1H); 4.32 (bm, 1H); 4.31 (bm, 1H); 3.48 (bm, 1H); 3.1 (bm, 1H); 2.83 (m, 3H); 2.78 (bm, 1H); 2.24 (s, 3H); 2.12 (m, 1H); 1.94 (m, 2H); 1.77 (m, 1H); 1.53 (m, 1H); 0.4 (m, 2H); 0.26 (m, 2H).

MS (ES/+) m/z=464 [M+H]$^+$.

EXAMPLE 31b

T.l.c.:AcOEt/MeOH 85:15, Rf=0.18.
NMR (d$_6$-DMSO): δ (ppm) 7.33 (bs, 1H); 7.11 (bm, 1H); 6.91 (bd, 2H); 6.85 (bs, 1H); 6.82 (bm, 1H); 4.4 (bm, 1H); 4.2 (bm, 1H); 4.15 (bd, 1H); 3.03 (bm, 1H); 2.96 (bs, 3H); 2.75 (bt, 1H); 2.5 (bm, 1H); 2.28 (bs, 3H); 2.11 (bm, 2H); 1.91 (bm, 1H); 1.53 (bq, 1H); 1.47 (bq, 1H); 0.39 (m, 2H); 0.23 (m, 2H).
MS (ES/+) m/z=464 [M+H]$^+$.

EXAMPLE 32

4-Cyclopropylamino-1-(4-fluoro-2-methyl-phenyl)-piperidine-2-carboxylic acid (3,5-dichloro-benzyl)-methylamide hydrochloride (diastereoisomer A)

A solution of example 31a (8 mg) in dry Et2O (1 mL) was treated with hydrochloric acid (1M in Et2O—0.019 mL) at 0° C. under a Nitrogen atmosphere. The resulting solution was stirred at 0° C. for 30 minutes, then it was concentrated in vacuo and the residue was triturated with pentane (2×3 mL) to give the title compound as a white solid (6.6 mg).
NMR (d$_6$-DMSO—70° C.): δ (ppm) 8.93 (bs, 2H); 7.42 (s, 1H); 7.2-6.8 (bm, 5H); 4.7-3.4 (m, 5H); 3.0-2.6 (m, 5H); 2.3-2.0 (m, 6H); 1.76 (m, 1H); 1.0-0.8 (m, 4H).
MS (ES/+) m/z=464 [M+H—HCl]$^+$.

EXAMPLE 33

4-Cyclopropylamino-1-(4-fluoro-2-methyl-phenyl)-piperidine-2-carboxylic acid (3,5-dichloro-benzyl)-methylamide hydrochloride (diastereoisomer B)

A solution of example 31b (9 mg) in dry Et2O (1 mL) was treated with hydrochloric acid (1M in Et2O—0.021 mL) at 0° C. under a Nitrogen atmosphere. The resulting solution was stirred at 0° C. for 30 minutes, then it was concentrated in vacuo and the residue was triturated with pentane (2×3 mL) to give the title compound as a white solid (9.3 mg).
NMR (d$_6$-DMSO—70° C.): δ (ppm) 9.0 (bs, 2H); 7.36 (s, 1H); 7.15 (bt, 1H); 6.95 (dd, 1H); 6.85 (m, 1H); 6.83 (s, 2H); 4.3 (bd, 1H); 4.8-4.0 (bm, 2H); 3.45 (bm, 1H); 3.0 (m, 1H); 2.8-2.5 (m, 2H); 3.04 (s, 3H); 2.31 (s, 3H); 2.3 (bm, 1H); 2.13 (bd, 1H); 1.92 (q, 1H; 1.82 (dq, 1H); 0.92-0.8 (m, 4H).
MS (ES/+) m/z=464 [M+H—HCl]$^+$.

EXAMPLE 34

4-(4-Acetyl-piperazin-1-yl)-1-(4-fluoro-2-methyl-phenyl)-piperidine-2-carboxylic acid (3,5-dichlorobenzyl)-methylamide (34a—diastereoisomer A) and

4-(4-Acetyl-piperazin-1-yl)-1-(4-fluoro-2-methyl-phenyl)-piperidine-2-carboxylic acid (3,5-dichloro-benzyl)-methylamide (34b—diastereoisomer B)

N-Acetyl-piperazine (35.8 mg) and sodium triacetoxyborohydride (58.1 mg) were added to a solution of intermediate 16 (58 mg) in anhydrous acetonitrile (3 mL) under a Nitrogen atmosphere. The solution was stirred at r.t. for 24 hours, then it was diluted with AcOEt (15 mL) and washed with a 5% sodium hydrogen carbonate solution (15 mL) and brine (10 mL). The organic layer was dried and concentrated in vacuo to a residue which was purified by flash chromatography (AcOEt/MeOH 85:15) to give two fractions:

1. example 34a (2 mg) as colourless oil
2. example 34b (9 mg) as colourless oil.

EXAMPLE 34a

T.l.c.:AcOEt/MeOH 8:2, Rf=0.33.

EXAMPLE 34b

T.l.c.:AcOEt/MeOH 8:2, Rf=0.23.
NMR (d$_6$-DMSO): δ (ppm) 7.33 (s, 1H); 7.09 (m, 1H); 6.92-6.79 (m, 4H); 4.5-4.2 (bm, 2H); 4.16 (d, 1H); 3.43 (m, 4H); 3.04 (m, 2H); 2.9 (bs, 3H); 2.5 (m, 5H); 2.29 (bs, 3H); 2.11-1.6 (m, 4H); 1.26 (s, 3H).
MS (ES/+) m/z=535 [M+H]$^+$.

EXAMPLE 35

4-(4-Acetyl-piperazin-1-yl)-1-(4-fluoro-2-methyl-phenyl)-piperidine-2-carboxylic acid (3,5-dichloro-benzyl)-methylamide hydrochloride (diastereoisomer B)

A solution of example 34b (5.3 mg) in dry Et2O (1 mL) was treated with hydrochloric acid (1M in Et2O—0.011 mL) at 0° C. under a Nitrogen atmosphere. The resulting solution was stirred at 0° C. for 30 minutes, then it was concentrated in vacuo and the residue was triturated with pentane (2×3 mL) to give the title compound as a white solid (4.5 mg).
MS (ES/+) m/z=535 [M+H—HCl]$^+$.

EXAMPLE 36

4-Cyclopropylamino-1-(4-fluoro-2-methyl-phenyl)-piperidine-2-carboxylic acid [1-(R)-3,5-bis-trifluoromethyl-phenyl)-ethyl]-methylamide (36a—diastereoisomer A) and

4-Cyclopropylamino-1-(4-fluoro-2-methyl-phenyl)-piperidine-2-carboxylic acid [1-(R)-3,5-bis-trifluoromethyl-phenyl)-ethyl]-methylamide (36b—diastereoisomer B)

Cyclopropylamine (0.015 mL) was added to a solution of intermediate 17a (56 mg) in anhydrous acetonitrile (1 mL) under a Nitrogen atmosphere. The solution was stirred at r.t. for 10 minutes, then sodium triacetoxyborohydride (34 mg) was added. The mixture was stirred at 23° C. for 18 hours, then it was diluted with DCM (15 mL) and washed with a 5% sodium hydrogen carbonate solution (15 mL) and brine (10 mL). The organic layer was dried and concentrated in vacuo to a residue which was purified by flash chromatography (AcOEt/MeOH 9:1) to give two fractions:

1. example 36a (12 mg) as yellow oil
2. example 36b (23 mg) as yellow oil.

EXAMPLE 36a

T.l.c.: AcOEt/MeOH 9:1, Rf=0.32.
HPLC: column: Supelcosil ABZ Plus 15 cm×46 mm×5μ; mobile phase: acetonitrile/10 mM ammonium acetate solution from 40:60 to 90:10 in 5 minutes, then 90:10 for 10 minutes; flux=0.8 mL/min; λ=360 nm; retention time 10.2 minutes.

EXAMPLE 36b

T.l.c.: AcOEt/MeOH 9:1, Rf=0.22.
HPLC: column: Supelcosil ABZ Plus 15 cm×46mm×5ll; mobile phase: acetonitrile/10 mM ammonium acetate solution from 40:60 to 90:10 in 5 minutes, then 90:10 for 10 minutes; flux=0.8 mL/min; λ=360 nm; retention time 9.4 minutes.

EXAMPLE 37

4-Cyclopropylamino-1-(4-fluoro-2-methyl-phenyl)-piperidine-2-carboxylic acid [1-(R)-3,5-bis-trifluoromethyl-phenyl)-ethyl]-methylamide hydrochloride (diastereoisomer A)

A solution of example 36a (12 mg) in dry Et2O (0.5 mL) was treated with hydrochloric acid (1M in Et2O—0.024 mL) at 0° C. under a Nitrogen atmosphere. The resulting solution was stirred at 0° C. for 30 minutes, then it was concentrated in vacuo and the residue was triturated with pentane (2×1 mL) to give the title compound as a yellow solid (7.7 mg).

NMR ($d_6$-DMSO): δ (ppm) 8.9 (bm, 1H); 8.0-7.96 (2s, 1H); 7.78-7.41 (2s, 2H); 7.4-6.65 (m, 3H); 5.73-5.32 (2q, 1H); 4.5-4.46 (2m, 1H); 4.2-4.16 (2bm, 1H); 3.5-2.4 bm+m, 3H); 2.53-2.29 (2s, 3H); 2.29-2.03 (2s, 3H); 2.17 (m, 2H); 2.0 (m, 1H); 1.7 (m, 1H); 1.57-1.33 (2dd, 3H); 0.87 (m, 2H); 0.78 (m, 2H).
MS (ES/+) m/z=547[M+H—HCl]$^+$.

EXAMPLE 38

4-Cyclopropylamino-1-(4-fluoro-2-methyl-phenyl)-piperidine-2-carboxylic acid [1-(R)-3,5-bis-trifluoromethyl-phenyl)-ethyl]-methylamide hydrochloride (diastereoisomer B)

A solution of example 36b (22 mg) in dry Et2O (0.5 mL) was treated with hydrochloric acid (1M in Et2O—0.044 mL) at 0° C. under a Nitrogen atmosphere. The resulting solution was stirred at 0° C. for 30 minutes, then it was concentrated in vacuo and the residue was triturated with pentane (2×1 mL) to give the title compound as a yellow solid (18 mg).

NMR ($d_6$-DMSO): δ (ppm) 9.0 (bm, 2H); 7.9 (bs, 1H); 7.63 (bs, 2H); 7.13 (m, 1H); 6.94 (m, 1H); 6.86 (bm, 1H); 5.56 (bq, 1H); 4.25 (bd, 1H); 3.7-2.4 (bm+bm+bm, 4H); 2.85 (bs, 3H); 2.28 (bs, 3H); 2.27 (bm, 1H); 2.14 (bm, 1H); 1.96 (m, 1H); 1.84 (m, 1H); 1.28 (bs, 3H); 0.91 (m, 2H); 0.82 (m, 2H).
MS (ES/+) m/z=547[M+H—HCl]$^+$.

EXAMPLE 39

4-Cyclopropylamino-1-(4-fluoro-2-methyl-phenyl)-piperidine-2-carboxylic acid [1-(R)-3,5-bis-trifluoromethyl-phenyl)-ethyl]-methylamide (39a—diastereoisomer A) and 4-Cyclopropylamino-1-(4-fluoro-2-methyl-phenyl)-piperidine-2-carboxylic acid [1-(R)-3,5-bis-trifluoromethyl-phenyl)-ethyl]-methylamide (39b—diastereoisomer B)

Cyclopropylamine (0.010 mL) was added to a solution of intermediate 36b (36 mg) in anhydrous acetonitrile (1 mL) under a Nitrogen atmosphere. The solution was stirred at r.t. for 10 minutes, then sodium triacetoxyborohydride (22 mg) was added. The mixture was stirred at 23° C. for 18 hours, then it was diluted with DCM (15 mL) and washed with a 5% sodium hydrogen carbonate solution (15 mL) and brine (10 mL). The organic layer was dried and concentrated in vacuo to a residue which was purified by flash chromatography (AcOEt/MeOH 9:1) to give:
1. example 39a (3.7 mg) as yellow oil
2. example 39b (2.7 mg) as yellow oil.

EXAMPLE 39a

T.l.c.: AcOEt/MeOH 9:1, Rf=0.43.
HPLC: column: Supelcosil ABZ Plus 15 cm×46mm×5μ; mobile phase: acetonitrile/10 mM ammonium acetate solution from 40:60 to 90:10 in 5 minutes, then 90:10 for 10 minutes; flux=0.8 mL/min; λ=360 nm; retention time 10.2 minutes.

EXAMPLE 39b

T.l.c.: AcOEt/MeOH 9:1, Rf=0.31.
HPLC: column: Supelcosil ABZ Plus 15 cm×46 mm×5μ; mobile phase: acetonitrile/10 mM ammonium acetate solution from 40:60 to 90:10 in 5 minutes, then 90:10 for 10 minutes; flux=0.8 mL/min; λ=360 nm; retention time 8.99 minutes.

EXAMPLE 40

4-Cyclopropylamino-1-(4-fluoro-2-methyl-phenyl)-piperidine-2-carboxylic acid [1-(R)-3,5-bis-trifluoromethyl-phenyl)-ethyl]-methylamide hydrochloride (diastereoisomer A)

A solution of example 39a (3.7 mg) in dry Et2O (0.5 mL) was treated with hydrochloric acid (1M in Et2O—0.0074 mL) at 0° C. under a Nitrogen atmosphere. The resulting solution was stirred at 0° C. for 30 minutes, then it was concentrated in vacuo and the residue was triturated with pentane (2×1 mL) to give the title compound as a yellow solid (2.1 mg).

NMR ($d_6$-DMSO): δ (ppm) 8.8 (bm, 1H); 8.71 (bm, 1H); 8.04 (bs, 1H); 7.73 (bs, 2H); 6.95 (m, 2H); 6.65 (dt, 1H); 5.84 (q, 1H); 4.45 (m, 1H); 3.98 (bm, 1H); 3.59 (m, 1H); 2.91 (m, 1H); 2.78 (m, 1H); 2.39 (s, 3H); 2.18 (s, 3H); 2.2 (bm, 1H); 2.09 (m, 1H); 2.0 (m, 1H); 1.63 (m, 1H); 1.47 (d, 3H); 0.83 (m, 4H).
MS (ES/+) m/z=547[M+H—HCl]$^+$.

EXAMPLE 41

4-Cyclopropylamino-1-(4-fluoro-2-methyl-phenyl)-piperidine-2-carboxylic acid [1-(R)-3,5-bis-trifluoromethyl-phenyl)-ethyl]-methylamide hydrochloride (diastereoisomer B)

A solution of example 39b (2.7 mg) in dry Et2O (0.5 mL) was treated with hydrochloric acid (1M in Et2O—0.0054 mL) at 0° C. under a Nitrogen atmosphere. The resulting solution was stirred at 0° C. for 30 minutes, then it was concentrated in vacuo and the residue was triturated with pentane (2×1 mL) to give the title compound as a yellow solid (2.0 mg).

NMR ($d_6$-DMSO): δ (ppm) 8.81 (bs, 2H); 7.89 (bs, 1H); 7.52 (bs, 2H); 7.09 (m, 1H); 6.89 (bd, 1H); 6.71 (bm, 1H); 5.62 (bq, 1H); 4.29 (bd, 1H); 3.45 (bm 1H); 3.0 (bd, 1H);

2.9-2.4 (bm, 2H); 2.85 (s, 3H); 2.29 (s, 3H); 2.29 (bm, 1H); 2.13 (m, 1H); 1.88 (bq, 1H); 1.79 (m, 1H); 1.38 (bd, 3H); 0.85 (m, 4H).

MS (ES/+) m/z=547[M+H—HCl]$^+$.

EXAMPLE 42

4-Cyproylmethylamino-1-(4-fluoro-2-methyl-phenyl)-piperidine2-carboxylic acid (3,5-ditrifluoromethyl-benzyl)-methylamide (diastereoisomer B)

Cyclopropylmethylamine (70 mg) and sodium cyanoborohydride polymer bound (175 mg) were added to a solution of intermediate 18 (120 mg) in DCM (1.35 mL) and glacial acetic acid (0.15 mL) and the resulting mixture was shaken at r.t. for 16 hours. Then the resin was filtered off and washed with DCM (1 mL). The filtrate was washed with a saturated sodium hydrogen carbonate solution (1 mL) and then filtered with a Whatman filter tube. The organic layer was diluted with DCM (5 mL) and aldehyde polymer bound (890 mg) was added and the suspension was shaken at r.t. for 10 hours. Then the resin was filtered off and washed with DCM (1 mL). The filtrate was concentrated in vacuo and the residue was purified by HPLC (column: X-Terra C-18 30×1.9 cm; mobile phase: 10 mM ammonium acetate solution/acetonitrile from 50:50 to 10:90 in 16 min.; flow rate=7 mL/min.; λ=225 nm) Thus, the title compound was obtained (44 mg).

NMR (d$_6$-DMSO): δ (ppm) 7.90 (s, 1H); 7.54 (bs, 2H); 7.05 (bt, 1H); 6.88 (bd, 1H); 6.71 (bt, 1H); 4.71 (bs, 1H); 4.21 (bs, 2H); 4.1 (bs, 1H); 3.08 (s, 3H); 2.63 (bs, 2H); 2.5-1.2 (m, 2H); 2.40 (m, 2H); 2.24 (s, 3H); 2.06 (bs, 1H); 1.83 (d, 1H); 1.39 (bd, 1H); 0.84 (m, 1H); 0.37 (m, 2H); 0.08 (m, 2H).

MS (ES/+) m/z=478 [M+H]$^+$.

HPLC: column: X-Terra C-18 25×0.46 cm; mobile phase: 10 mN ammonium acetate solution/acetonitrile from 50:50 to 10:90 in 12 min.; flow rate=0.8 mL/min.; λ=225 nm; retention time: 8.0 minutes.

EXAMPLE 43

4-Cyclopropylmethylamino-1-(4-fluoro-2-methyl-phenyl)-piperidine-2-carboxylic acid (3,5-ditrifluoromethyl-benzyl)-methylamide (43a—diastereoisomer 1) and 4-Cyclopropylmethylamino-1-(4-fluoro-2-methyl-phenyl)-piperidine-2-carboxylic acid (3,5-ditrifluoromethyl-benzyl)-methylamide (43b—diastereoisomer 2)

Example 42 (40 mg) was purified by HPLC (column: Chiralpack AD 25×2.0 cm; mobile phase: n-hexane/EtOH 85:15; flow rate=7 mL/min.; λ=225 nm) to give:
1. example 43a (16 mg—retention time 12.2 minutes)
2. example 43b (16 mg—retention time 15 minutes).

EXAMPLE 43a

NMR (d$_6$-DMSO): δ (ppm) 7.90 (s, 1H); 7.54 (bs, 2H); 7.05 (bt 1H); 6.88 (bd, 1H); 6.71 (bt, 1H); 4.71 (bs, 1H); 4.21 (bs, 2H); 4.1 (bs, 1H); 3.08 (s, 3H); 2.63 (bs, 2H); 2.5-1.2 (m, 2H); 2.40 (m, 2H); 2.24 (s, 3H); 2.06 (bs, 1H); 1.83 (d, 1H); 1.39 (bd, 1H); 0.84 (m, 1H); 0.37 (m, 2H); 0.08 (m, 2H).

MS (ES/+) m/z478 [M+H]$^+$.

HPLC: column: Chiralpack AD 25×0.46 cm; mobile phase: n-hexane/EtOH 90:10; flow rate=1 mL/min.; μ=225 nm; retention time: 5.4 minutes.

EXAMPLE 43b

NMR (d$_6$-DMSO): δ (ppm) 7.90 (s, 1H); 7.54 (bs, 2H); 7.05 (bt, 1H); 6.88 (bd, 1H); 6.71 (bt, 1H); 4.71 (bs, 1H); 4.21 (bs, 2H); 4.1 (bs, 1H); 3.08 (s, 3H); 2.63 (bs, 2H); 2.5-1.2 (m, 2H); 2.40 (m, 2H); 2.24 (s, 3H); 2.06 (bs, 1H); 1.83 (d, 1H); 1.39 (bd, 1H); 0.84 (m, 1H); 0.37 (m, 2H); 0.08 (m, 2H).

MS (ES/+) m/z=478 [M+H]$^+$.

HPLC: column: Chiralpack AD 25×0.46 cm; mobile phase: n-hexane/EtOH 90:10; flow rate-1 mL/min.; λ=225 nm; retention time: 7.0 minutes.

EXAMPLE 44

1-(4-Fluoro-2-methyl-phenyl)-4-morpholino-piperidine-2-carboxylic acid (3,5-bis-trifluoromethyl-benzyl)-methylamide (diastereoisomer B)

Morpholine (85 mg) and sodium cyanoborohydride polymer bound (175 mg, 4.2 mmol/g) were added to a solution of intermediate 18 (120 mg) in DCM (1.35 mL) and glacial acetic acid (0.15 mL) and the resulting mixture was shaken at r.t. for 16 hours. Then the resin was filtered off and washed with DCM (1 mL). The filtrate was washed with a saturated sodium hydrogen carbonate solution (1 mL) and then filtered with a Whatman filter tube. The organic layer was diluted with DCM (8 mL) and isocyanate polymer bound (1.22 mg 2.0 mmol/g) was added and the suspension was shaken at r.t. for 10 hours. Then the resin was filtered away and washed with DCM (1 mL). The filtrate was concentrated in vacuo and the residue (85 mg) was purified by HPLC (column: X-Terra C-18 30×1.9 cm; mobile phase: 10 mM ammonium acetate solution/acetonitrile from 50:50 to 10:90 in 14 min; flow rate=7 mL/min.; λ=225 nm) to give the title compound (42 mg).

NMR (d$_6$-DMSO): δ (ppm) 7.92 (s, 1H); 7.55 (s, 2H); 7.07 (dd, 1H); 6.91 (d, 1H); 6.74 (td, 1H); 4.74 (bm, 1H); 4.24 (bm, 2H); 4.1 (bs, 1H); 3.6 (m, 4H); 3.3 (m, 2H); 3.11 (s, 3H); 2.92 (bs, 1H); 2.5 (m, 4H); 2.27 (s, 3H); 2.00 (m, 1H); 1.80 (m, 1H); 1.56 (m, 2H).

MS (ES/+) m/z=494 [M+H]$^+$.

HPLC: column: X-Terra C-18 25×0.46 cm; mobile phase: 10 mM ammonium acetate solution/acetonitrile from 50/50 to 10/90 in 12 min; flow rate=0.8 mL/min; λ=225 nm; retention time: 11.9 minutes.

EXAMPLE 45

1-(4-Fluoro-2-methyl-phenyl)-4-morpholino-piperidine-2-carboxylic acid, (3,5-bis-trifluoromethyl-benzyl)-methylamide (45a—diastereoisomer 1) and 1-(4-Fluoro-2-methyl-phenyl)-4-morpholino-piperidine-2-carboxylic acid, (3,5-bis-trifluoromethyl-benzyl)-methylamide (45b—diastereoisomer 2)

Example 44 (38 mg) was purified by HPLC (column: Chiralpack AD 25×2.0 cm; mobile phase: n-hexane/EtOH 80:20; flow rate=7 mL/min.; λ=225 nm) to give:
1. example 45a (13 mg—retention time 13.5 minutes)
2. example 45b (13 mg—retention time 16.1 minutes).

EXAMPLE 45a

NMR (d$_6$-DMSO): δ (ppm) 7.92 (s, 1H); 7.55 (s, 2H); 7.07 (dd, 1H); 6.91 (d, 1H); 6.74 (td, 1H); 4.74 (bm, 1H); 4.24 (bm, 214); 4.1 (bs, 1H); 3.6 (m, 4H); 3.3 (m, 2H); 3.11 (s, 3H); 2.92 (bs, 1H); 2.5 (m, 4H); 2.27 (s, 3H); 2.00 (m, 1H); 1.80 (m, 1H); 1.56 (m, 2H).

MS (ES/+) m/z=494 [M+H]$^+$.

HPLC: column: Chiralpack AD 25×0.46 cm; mobile phase: n-hexane/EtOH 80/20; flow rate=1 mL/min.; λ=225 nm; retention time: 4.9 minutes.

EXAMPLE 45b

NMR (d$_6$-DMSO): δ (ppm) 7.92 (s, 1H); 7.55 (s, 2H); 7.07 (dd, 1H); 6.91 (d, 1H); 6.74 (td, 1H); 4.74 (bm, 1H); 4.24 (bm, 2H); 4.1 (bs, 1H); 3.6 (m, 4H); 3.3 (m, 2H); 3.11 (s, 3H); 2.92 (bs, 1H); 2.5 (m, 4H); 2.27 (s, 3H); 2.00 (m, 1H); 1.80 (m, 1H); 1.56 (m, 2H).

MS (ES/+) m/z=494 [M+H]$^+$.

HPLC: column: Chiralpack AD 25×0.46 cm; mobile phase: n-hexane/EtOH 80/20; flow rate: 1 mL/min.; λ=225 nm; retention time: 6.0 minutes.

EXAMPLE 46

4-(4-Acetylpiperazinyl)-1-(4-fluoro-2-methyl-phenyl)-piperidine-2-carboxylic acid, (3,5-bis-trifluoromethyl-benzyl)-methylamide (diastereoisomer B)

N-Acetylpiperazine (126 mg) and sodium cyanoborohydride polymer bound (175 mg) were added to a solution of intermediate 18 (120 mg) in DCM (1.35 mL) and glacial acetic acid (0.15 mL) and the resulting mixture was shaken at r.t. for 16 hours. Then the resin was filtered off and washed with DCM (1 mL). The filtrate was washed with a saturated sodium hydrogen carbonate solution (1 mL) and then filtered with a Whatman filter tube. The organic layer was diluted with DCM (8 mL) and isocyanate polymer bound (1.22 mg) was added and the suspension was shaken at r.t. for 10 hours. Then the resin was filtered off and washed with DCM (1 mL). The filtrate was concentrated in vacuo and the residue (92 mg) was purified by HPLC (column: X-Terra C-18 30×1.9 cm; mobile phase: 10 mM. ammonium. acetate solution/acetonitrile from 50/50 to 10/90 in 12 min.; flow rate=7 mL/min; λ=225 nm) to give the title compound (48 mg).

NMR (d$_6$-DMSO): δ (ppm) 7.92 (s, 1H); 7.55 (s, 2H); 7.07 (dd, 1H); 6.91 (d, 1H); 6.74 (td, 1H); 4.74 (bm, 1H); 4.24 (bm, 2H); 4.1 (bs, 1H); 3.6 (m, 4H); 3.5-3.2 (m, 4H); 3.3 (m, 2H); 3.11 (s, 3H); 2.92 (bs, 1H); 2.6-2.36 (m, 4H); 2.5 (m, 4H); 2.27 (s, 3H); 2.00 (m, 1H); 1.80 (m, 1H); 1.56 (m, 2H).

MS (ES/+) m/z=535 [M+H]$^+$.

HPLC: column: X-Terra C-18 25×0.46 cm; mobile phase: 10 mM ammonium acetate solution/acetonitrile from 50/50 to 10/90 in 12 min; flow rate=0.8 mL/min; λ=225 nm; retention time: 9.7 minutes.

EXAMPLE 47

4-(4-Acetylpiperazino)-1-(4-fluoro-2-methyl-phenyl)-piperidine-2-carboxylic acid (3,5-ditrifluoromethyl-benzyl)-methylamide (47a—diastereoisomer 1) and 4-(4-Acetylpiperazino)-1-(4-fluoro-2-methyl-phenyl)-piperidine-2-carboxylic acid (3,5-ditrifluoromethyl-benzyl)-methylamide (47a—diastereoisomer 2)

Example 46 (45 mg) was purified by chiral HPLC (column: Chiralcel OD 25×2.0 cm; mobile phase: n-hexane/EtOH 80/20; flow rate: 7 mL/min; λ=225 nm) to give:

1. example 47a (18 mg—retention time 19.7 minutes)
2. example 47b (17 mg—retention time 31.1 minutes)

EXAMPLE 47a

NMR (d$_6$-DMSO): δ (ppm) 7.92 (s, 1H); 7.55 (s, 2H); 7.07 (dd, 1H); 6.91 (d, 1H); 6.74 (td, 1H); 4.74 (bm, 1H); 4.24 (bm, 2H); 4.1 (bs, 1H); 3.6 (m, 4H); 3.5-3.2 (m, 4H); 3.3 (m, 2H); 3.11 (s, 3H); 2.92 (bs, 1H); 2.6-2.36 (m, 4H); 2.5 (m, 4H); 2.27 (s, 3H); 2.00 (m, 1H); 1.80 (m, 1H); 1.56 (m, 2H).

MS (ES/+) m/z=535 [M+H]$^+$.

HPLC: column Chiralcel OD 25×0.46 cm; mobile phase: n-hexane/EtOH 80/20; flow rate: 1 mL/min; 225 nm; retention time 7.2 minutes.

EXAMPLE 47b

NMR (d$_6$-DMSO): δ (ppm) 7.92 (s, 1H); 7.55 (s, 2H); 7.07 (dd, 1H); 6.91 (d, 1H); 6.74 (td, 1H); 4.74 (bm, 1H); 4.24 (bm, 2H); 4.1 (bs, 1H); 3.6 (m, 4H); 3.5-3.2 (m, 4H); 3.3 (m, 2H); 3.11 (s, 3H); 2.92 (bs, 1H); 2.6-2.36 (m, 4H); 2.5 (m, 4H); 2.27 (s, 3H); 2.00 (m, 1H); 1.80 (m, 1H); 1.56 (m, 2H).

MS (ES/+) m/z=535 [M+H]$^+$.

HPLC: column Chiralcel OD 25×0.46 cm; mobile phase: n-hexane/EtOH 80/20; flow rate: 1 mL/min; λ=225 nm; retention time 11.7 minutes.

PHARMACY EXAMPLES

A. Tablets

| | |
|---|---|
| Active ingredient | 10.0 mg |
| PVP | 9 mg |
| Microcrystalline Cellulose | 266 mg |
| Sodium Starch Glycolate | 12 mg |
| Magnesium Stearate | 3 mg |
| Active ingredient | 50 mg |
| PVP | 9 mg |
| Microcrystalline Cellulose | 226 mg |
| Sodium Starch Glycolate | 12 mg |
| Magnesium Stearate | 3 mg |

The active ingredient is blended with the other excipients. The blend can be compressed to form tablets using appropriate punches. The tablets can be coated using conventional techniques and coatings.

B. Capsules

| | |
|---|---|
| Active ingredient | 25.0 mg (1-100 mg) |
| Microcrystalline Cellulose | qs |

The active ingredient is blended with microcrystalline cellulose and then filled into suitable capsules.

C) Injection

| | |
|---|---|
| Active ingredient | 2-20 mg/mL |
| Buffer solution pH 3.5 (3.0-4.0) suitable for injection (e.g. citrate buffer in sterile water for injection or NaCl 0.9%) | qs to 10 mL |

The formulation may be packaged in glass or plastic vials or ampules. The formulation may be administered by bolus injection or infusion, e.g. after dilution with D5W or 0.9% NaCl.

The affinity of the compound of the invention for $NK_1$ receptor was determined using the $NK_1$ receptor binding affinity method measuring in vitro by the compounds' ability to displace [3H]—substance P (SP) from recombinant human $NK_1$ receptors expressed in Chinese Hamster Ovary (CHO) cell membranes. The affinity values are expressed as negative logarithm of the inhibition constant (Ki) of displacer ligands (pKi).

The pKi values obtained as the average of at least two determinations with representative compounds of the invention are within the range of 8.24 to 10.21.

The invention claimed is:
1. A compound selected from:
4-(2,2-Dimethyl-propylamino)-2-(4-fluoro-2-methyl-phenyl)-piperdine-1-carboxylic acid, [1-(R)-(3,5-bis-trifluoromethyl-phenyl)-ethyl]-methylamide;
4-Ethylamino-2-(4-fluoro-2-methyl-phenyl)-piperidine-1-carboxylic acid [1-(R)-(3,5-bis-trifluoromethyl-phenyl)-ethyl]-methylamide;
4-Dimethylamino-2-(4-fluoro-2-methyl-phenyl)piperidine-1-carboxylic acid [1-(R)-(3,5-bis-trifluoromethyl-phenyl )-ethyl]-methylamide;
4-Dimethylamino-2-(R)-(4-fluoro-2-methyl-phenyl)piperidine-1-carboxylic acid (3,5-bis-trifluoromethyl-benzyl)-methylamide;
4-(2-Fluoroethyl)-amino-2-(4-fluoro-2-methyl-phenyl)-piperidine-1-carboxylic acid [1-(R)-(3,5-bis)-trifluoromethyl-phenyl)-ethyl]-methylamide;
4-(2-Fluoro-ethylamino)-2-(4-fluoro-2-methyl-phenyl)-piperdine-1-carboxylic acid (3,5-bis-trifluoromethyl-benzyl)-methylamide;
4-(N-2-Fluoroethyl-N-methylamino)-2-(4-fluoro-2-methyl-phenyl)-piperidine-1-carboxylic acid, (3,5-bis-trifluoromethyl-benzyl)-methylamide;
2-(4-Fluoro-2-methyl-phenyl)-4-(2-methoxyethylamino)-piperidine-1-carboxylic acid [1-(R)-(3,5-bis-trifluoromethyl-phenyl)-ethyl]-methylamide;
2-(4-Fluoro-2-methyl-phenyl)-4-methylamino-piperidine-1-carboxylic acid [1-(R)-(3,5-bis-trifluoromethyl-phenyl)-ethyl]-methylamide;
2-(4-Fluoro-2-methyl-phenyl)-4-methylamino-piperidine-1-carboxylic acid (3,5-bis-trifluoromethyl-benzyl)-methylamide;
4-Amino-2-(4-fluoro-2-methyl-phenyl)-piperidine-1-carboxylic acid (3,5-bis-trifluoromethyl-benzyl)-methylamide;
4-Cyclobutylamino-2-(4-fluoro-2-methyl-phenyl)-piperidine-1-carboxylic acid [1-(R)-(3,5-bis)-trifluoromethyl-phenyl)-ethyl]-methylamide;
4-Cyclopropylamino-2-(4-fluoro-2-methyl-phenyl)-piperidine-1-carboxylic acid [1-(R)-(3,5-bis-trifluoromethyl-phenyl)-ethyl]-methylamide;
4-Benzylamino-2-(4-fluoro-2-methyl-phenyl)-piperidine-1-carboxylic acid (3,5-bis-trifluoromethyl-benzyl)-methylamide;
4-(-N-2-Fluoroethyl-N-methylamino)-2-(R)-(4-fluoro-2-methyl-phenyl)-piperidine-1-carboxylic acid (3,5-bis-trifluoromethyl-benzyl)-methylamide;
4-Cyclopropylamino-1-(4-fluoro-2-methyl-phenyl)-piperidine-2-carboxylic acid (3,5-dichloro-benzyl)-methylamide;
4-Cyclopropylamino-1-(4-fluoro-2-methyl-phenyl)-piperidine-2-carboxylic acid [1-(R)-3,5-bis-trifluoromethyl-phenyl)-ethyl]-methylamide; and 4-(R,S)-(2,2,2-Trifluoroethyl)-amino-2-(R)-(4-fluoro-2-methyl-phenyl)-piperidine-1-carboxylic acid [1-(R)-(3,5-bis-trifluoromethyl-phenyl)-ethyl]-methylamide hydrochloride; and
diastereoisomers and acceptable pharmaceutical salts thereof.
2. A compound selected from:
4-(S)-Dimethylamino-2-(R)-(4-fluoro-2-methyl-phenyl) piperidine-1-carboxylic acid [1-(R)-(3,5-bis-trifluoromethyl-phenyl)-ethyl]-methylamide hydrochloride;
4-(S)-Dimethylamino-2-(R)-(4-fluoro-2-methyl-phenyl)-piperidine-1-carboxylic acid (3,5-bis-trifluoromethyl-benzyl)-methylamide hydrochloride;
4(S)-(2-Fluoroethyl)-amino-2-(R)-(4-fluoro-2-methyl-phenyl)-piperdine-1-carboxylic acid [1-(R)-(3,5-bis)-trifluoromethyl-phenyl)-ethyl]-methylamide hydrochloride; and
4-(S)-(2-Fluoro-ethylamino)-2-(R)-(4-fluoro-2-methyl-phenyl )-piperidine-1-carboxylic acid (3,5-bis-trifluoromethyl-benzyl)-methylamide hydrochloride.
3. A pharmaceutical composition comprising a compound as claimed in claim 1 in a mixture with one or more pharmaceutically acceptable carriers or excipients.
4. A pharmaceutical composition comprising a compound as claimed in claim 2 in a mixture with one or more pharmaceutically acceptable carriers or excipients.
5. A process for the preparation of a compound as claimed in claim 1 by reductive N-alkylation of the compound of formula (II)

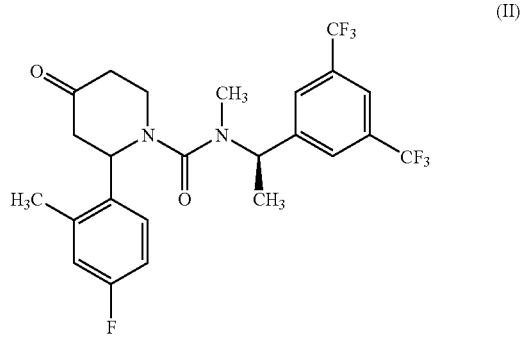

(II)

with an amine selected from 2,2,2-trifluoroethylamine, 2,2-dimethyl-propylamine, ethylamine, dimethylamine, 2-fluoroethylamine, 2-methoxyethylamine, methylamine, cyclopropylamine or cyclobutylamine or salts thereof or of the compound of formula (III)

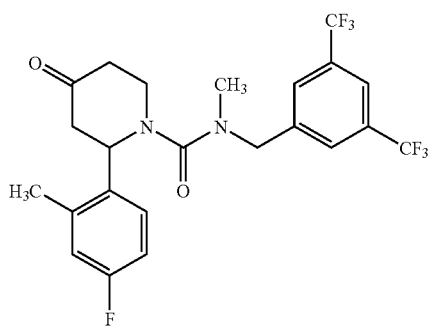
(III)

with an amine selected from dimethylamine, 2-fluoroethylamine, methylamine, benzylamine and salts thereof,
or of the compound of formula (IV)

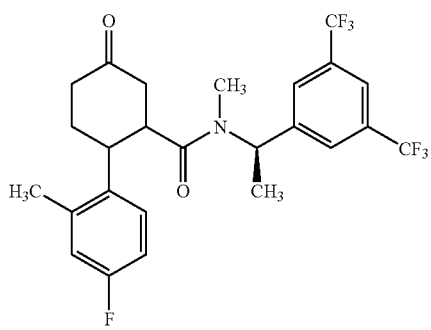
(IV)

with cyclopropylamine or a salt thereof, or
of the compound of formula (V)

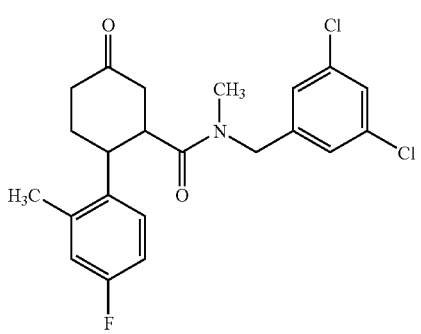
(V)

with cyclopropylamine or a salt thereof or by reaction of a compound of formula (VI)

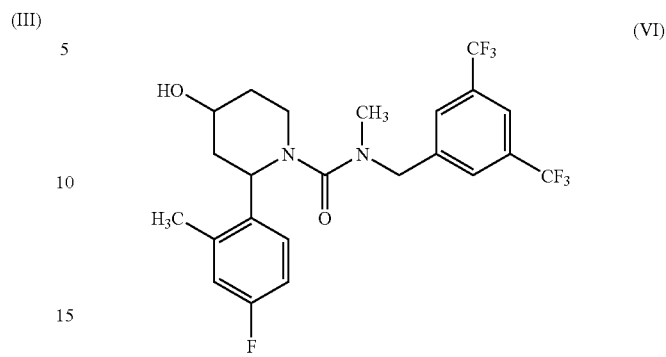
(VI)

with methanesulphonyl chloride in the presence of triethylamine followed by treatment with sodium azide and then with triphenylphosphine or
by reacting a compound of formula (VII)

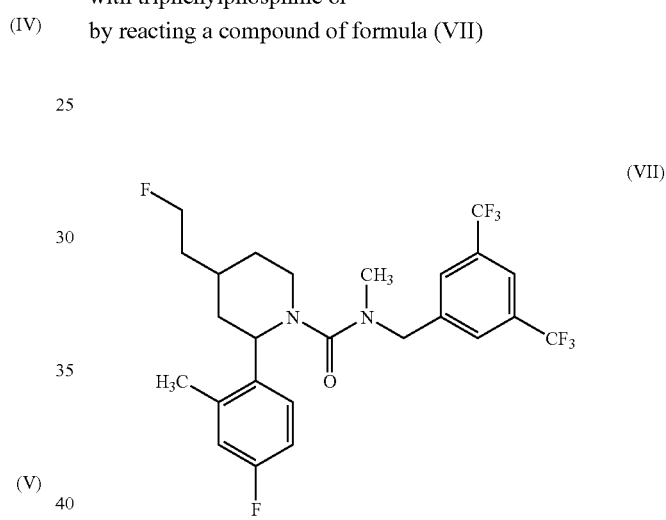
(VII)

with formaldehyde in the presence of 10% palladium over charcoal and acetic acid;
followed where necessary or desired by one or more of the following steps:
i) removal of any protecting group;
ii) isolation of the compound as a salt or a solvate thereof;
separation of a compound of formula (I) or salt or a solvate thereof into diasteroisomers thereof.

* * * * *